United States Patent
Skucas et al.

(10) Patent No.: US 11,479,533 B2
(45) Date of Patent: Oct. 25, 2022

(54) INHIBITORS OF RHO ASSOCIATED COILED-COIL CONTAINING PROTEIN KINASE

(71) Applicant: KADMON CORPORATION, LLC, New York, NY (US)

(72) Inventors: Eduardas Skucas, Medford, MA (US); Kevin G. Liu, West Windsor, NJ (US); Ji-In Kim, Princeton, NJ (US); Masha V. Poyurovsky, New York, NY (US); Rigen Mo, Livingston, NJ (US); Jingya Zhang, Great Neck, NY (US)

(73) Assignee: Kadmon Corporation, LLC, New York, NY (US)

( * ) Notice: Subject to any disclaimer, the term of this patent is extended or adjusted under 35 U.S.C. 154(b) by 0 days.

(21) Appl. No.: 16/632,662

(22) PCT Filed: Jul. 23, 2018

(86) PCT No.: PCT/US2018/043335
§ 371 (c)(1),
(2) Date: Jan. 21, 2020

(87) PCT Pub. No.: WO2019/018855
PCT Pub. Date: Jan. 24, 2019

(65) Prior Publication Data
US 2020/0165206 A1 May 28, 2020

Related U.S. Application Data

(60) Provisional application No. 62/535,611, filed on Jul. 21, 2017.

(51) Int. Cl.
| C07D 231/40 | (2006.01) |
| C07D 231/12 | (2006.01) |
| C07D 401/12 | (2006.01) |
| C07D 403/10 | (2006.01) |
| C07D 403/12 | (2006.01) |
| C07D 413/12 | (2006.01) |
| C07D 417/12 | (2006.01) |

(52) U.S. Cl.
CPC .......... *C07D 231/40* (2013.01); *C07D 231/12* (2013.01); *C07D 401/12* (2013.01); *C07D 403/10* (2013.01); *C07D 403/12* (2013.01); *C07D 413/12* (2013.01); *C07D 417/12* (2013.01)

(58) Field of Classification Search
CPC .............. C07D 231/40; C07D 231/12; C07D 401/12; C07D 403/10; C07D 403/12; C07D 413/12; C07D 417/12
See application file for complete search history.

(56) References Cited

U.S. PATENT DOCUMENTS

| 8,211,919 B2 | 7/2012 | Sawada et al. | |
| 2011/0038835 A1 | 2/2011 | Feng et al. | |
| 2016/0152621 A1* | 6/2016 | Hartz | C07D 213/56 514/210.2 |
| 2020/0199109 A1* | 6/2020 | Skucas | A61P 11/00 |
| 2021/0163421 A1* | 6/2021 | Skucas | A61P 25/28 |

FOREIGN PATENT DOCUMENTS

| WO | 2003053941 A2 | 7/2003 | |
| WO | 03064397 A1 | 8/2003 | |
| WO | 2014/134391 A1 | 9/2014 | |
| WO | WO-2015070170 A1 * | 5/2015 | .......... C07D 213/56 |
| WO | 2016022312 A1 | 2/2016 | |

OTHER PUBLICATIONS

Extended European Search Report in Application EP 18834641, 10 pages, dated Feb. 15, 2021. (Year: 2021).*
Fang; J. Med. Chem. 2010, 53, 15, 5727-573. DOI: 10.1021/jm100579r (Year: 2010).*
Feng; J. Med. Chem. 2016, 59, 6, 2269-2300. https://doi.org/10.1021/acs.jmedchem.5b00683 (Year: 2016).*

\* cited by examiner

*Primary Examiner* — Daniel R Carcanague
(74) *Attorney, Agent, or Firm* — McNeill Baur, PLLC

(57) ABSTRACT

The invention relates to inhibitors of ROCK1 and/or ROCK2. Also provided are methods of inhibiting ROCK1 and/or ROCK2 that are useful for the treatment of disease.

20 Claims, 21 Drawing Sheets

INHIBITORS OF RHO ASSOCIATED COILED-COIL CONTAINING PROTEIN KINASE

FIELD OF THE INVENTION

The invention relates to inhibitors of ROCK1 and/or ROCK2. Also provided are methods of inhibiting ROCK1 and/or ROCK2 that are useful for the treatment of disease.

BACKGROUND OF THE INVENTION

The Rho Associated Coiled-Coil Containing Protein Kinases (ROCK) are members of the serine/threonine kinase family. Two isoforms, ROCK1 and ROCK2, have been identified. Both isoforms are activated by GTP-bound forms of Rho GTPase and when activated phosphorylate a variety of downstream substrates. ROCKs play important roles in numerous cellular processes including smooth muscle cell contraction, cell proliferation, adhesion and migration. As such, ROCK inhibitors have potential therapeutic applicability in a wide variety of pathological conditions including, for example, asthma, cancer, erectile dysfunction, glaucoma, insulin resistance, kidney failure, pulmonary hypertension, neuronal degeneration, and osteoporosis.

ROCK is a key intracellular regulator of cytoskeletal dynamics and cell motility. Rho-kinase regulates a number of downstream targets of RhoA through phosphorylation, including, for example, myosin light chain, the myosin light chain phosphatase binding subunit and LIM-kinase 2. These substrates regulate actin filament organization and contractility. In smooth muscle cells, ROCK mediates calcium sensitization and smooth muscle contraction. Inhibition of ROCK blocks 5-HT and phenylephrine agonist induced muscle contraction. When introduced into non-smooth muscle cells, ROCK induces stress fiber formation and is required for the cellular transformation mediated by RhoA. ROCK participates in a variety of cellular processes, including but not limited to cell adhesion, cell motility and migration, growth control, cell contraction, and cytokinesis. ROCK is also involved in Na/H exchange transport system activation, stress fiber formation, adducin activation, and physiological processes such as vasoconstriction, bronchial smooth muscle constriction, vascular smooth muscle and endothelial cell proliferation, platelet aggregation, and others.

Inhibition of ROCK activity in animal models has demonstrated a number of benefits of Rho-kinase inhibition for the treatment of human diseases. These include models of cardiovascular diseases such as hypertension, atherosclerosis, restenosis, cardiac hypertrophy, ocular hypertension, cerebral ischemia, cerebral vasospasm, penile erectile dysfunction, central nervous system disorders such as neuronal degeneration and spinal cord injury, and in neoplasias. Inhibition of ROCK activity has been shown to inhibit tumor cell growth and metastasis, angiogenesis, arterial thrombotic disorders such as platelet aggregation and leukocyte aggregation, asthma, regulation of intraocular pressure, and bone resorption. The inhibition of ROCK activity in patients has benefits for controlling cerebral vasospasms and ischemia following subarachnoid hemorrhage, reduction of intraocular pressure, increase in ocular aqueous outflow by relaxation of trabecular meshwork tissue, improving blood flow to the optic nerve, and protection of healthy ganglion cells.

A substantial body of in vivo data has been generated focusing on the activity of ROCK in the CNS. Abnormal activation of the ROCK pathway has been documented in many disorders of the central nervous system. For example, axon growth and synaptic plasticity are dependent on the structural regulation of the actin cytoskeleton. The Rho-ROCK cascade has a central role in synaptic plasticity, both in dendrite morphogenesis and stability as well as in growth cone motility and collapse. In addition, multiple axon growth inhibitory molecules converge on RhoA/ROCK in neurons making this an attractive pathway for intervention in CNS disorders.

Nogo-receptors (NgR) (along with other complex members, including LINGO-1) and their ligands are perhaps the most well characterized and potent inhibitors of neurite outgrowth. Some of the earliest events downstream of receptor activation by the myelin-associated inhibitors are the upregulation of RhoA and ROCKs. These events lead to increased contractility and have strong inhibitory effects on axonal growth in mature neurons. Thus, the possibility of inhibiting this signal cascade provides a very promising therapeutic strategy in Spinal Cord and Optical Nerve injuries. Neurodegenerative conditions such as Huntington's and Alzheimer's (AD) disease are also being investigated as responsive to inhibition of the NgR signaling. Not only do NgR family members associate with APP processing but also subcellular localization of NgR and Nogo is altered in AD brain.

Alzheimer's disease (AD), the most common cause of dementia in the elderly, is a progressive neurodegenerative disorder, which involves a gradual decline of many cognitive functions including memory impairment (Selkoe, 2001). Synaptic loss is generally observed in AD pathology and is the hallmark of synaptic dysfunction in AD (Tanzi and Bertram, 2005). Oligomerized β-amyloid peptides have been implicated in the loss of synaptic plasticity and neural network dysfunction. Synaptic plasticity is dependent on the structural regulation of the actin cytoskeleton in dendritic spines. Rho-ROCK cascade has a central role in synaptic plasticity, both in dendrite morphogenesis and stability as well as in growth cone motility and collapse (Govek et al., 2005; Linseman and Loucks, 2008). Several studies have demonstrated that ROCK kinases can induce generation of toxic β-amyloid peptide and furthermore, inhibition of ROCKs, can inhibit toxic peptide processing. In a feed-forward mechanism, β-amyloid increases the Rho GTPase activity, which via ROCK activation inhibits neurite outgrowth and synapse formation (Petratos et al., 2008). Thus, ROCK inhibitors may hold the potential for preventing synaptic and neuronal degradation as well as for promoting regenerative processes in AD. A recent study by Herskowitz et al. showed that ROCK knockdown decreased aβ levels. These effects demonstrate that highly ROCK selective inhibitors are needed to provide an effective treatment of Alzheimer's disease (AD). A model compound, SR3677, was tested in a rodent model of AD, in an effort to demonstrate the use of ROCK inhibition for AD, by altering BACE-1 distribution and amyloid precursor protein (APP) trafficking to lysosomes. After a direct i.p. injection into hippocampus due to its poor oral PK properties (5% F and <1 hr half-life) and lack of brain penetration, SR3677 had the promising effect of lowering sAPPβ.

Huntington's disease (HD) is a devastating, untreatable, dominantly inherited neurodegenerative disease characterized by psychiatric disturbance, motor impairment, and dementia. Misfolding and aggregation of the Htt protein, a product of the huntingtin gene, causes the HD pathology (Shao and Diamond, 2007). Very few mechanism-based therapeutic leads for treatment of HD have been developed. While scientific investigations are still ongoing, multiple lines of evidence suggest that ROCK inhibition may constitute an effective treatment for HD. In mouse models of HD, ROCK inhibition significantly reduced soluble Htt levels, reversed aggregate formation, neurite retraction and was protective against neuronal cell death (Deyts et al., 2009; Li et al., 2009). Similar results were obtained in *Drosophila* studies, where inhibition of ROCK controlled Htt aggregation (Shao et al., 2008a; Shao et al., 2008b). The ROCK signaling pathway is a promising therapeutic target for HD.

ROCK signaling has also been implicated in Parkinson's disease and amyotrophic lateral sclerosis (ALD). See, e.g., Tönges, L. et al. (2012). "Inhibition of rho kinase enhances survival of dopaminergic neurons and attenuates axonal loss in a mouse model of Parkinson's disease." Brain. 135(11): 3355-70.

ROCKs phosphorylate multiple downstream substrates, including myosin-light-chain (MLC, at threonine 18 and serine 19) and myosin light-chain phosphatase (MYPT1, at threonine 853), to drive the polymerization of globular G-actin into filamentous F-actin and assemble actomyosin contractile machinery. It has been recognized that this pathway is may contribute to the pathogenesis of several CNS disorders such as spinal cord injuries, stroke, and AD. In the adult CNS, injured axons regenerate poorly due to the presence of myelin-associated axonal growth inhibitors. Myelin-associated inhibitors such as myelin-associated glycoprotein (MAG), Nogo, oligodendrocyte-myelin glycoprotein (OMgp) and repulsive guidance molecule (RGM) limit axonal regeneration in the injured brain and spinal cord. A common mechanism for various myelin-associated inhibitors is that they all activate Rho and its downstream effector kinase ROCKs to inhibit neurite outgrowth.

Blockade of Rho/ROCK pathway by small molecule is a desirable strategy in central nervous system (CNS) disorders. However, the blood-brain barrier (BBB) while serving a critical role in brain homeostasis, also significantly impedes the penetration of most small molecule inhibitors. With growing interest in developing selective and potent inhibitors for the treatment of CNS diseases, there is an urgent need for inhibitors of ROCK 1 and/or ROCK 2, in particular those that cross the blood-brain barrier.

SUMMARY OF THE INVENTION

In one aspect, the present invention provides compounds of Formula I:

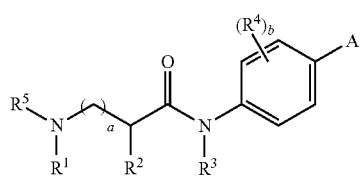

(I)

wherein:
A is selected from the group consisting of

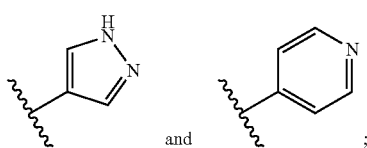 [SMILES: *c1cn[nH]c1 ; *c1ccncc1]

and ;

$R^1$ is selected from the group consisting of lower alkyl, substituted lower alkyl, $C_3$-$C_6$ cycloalkyl, substituted $C_3$-$C_6$ cycloalkyl, $R^{10}R^{11}N(CR^{12}R^{13})_c$—, $R^{10}O(CR^{12}R^{13})_c$—, $W(CR^{12}R^{13})_d$— and $R^{10}R^{11}N$—C(=O)—$(CR^{12}R^{13})_c$—;

each $R^{10}$ is independently selected from H, lower alkyl, and $C_3$-$C_6$ cycloalkyl;

each $R^{11}$ is independently selected from H, lower alkyl, and $C_3$-$C_6$ cycloalkyl;

each $R^{12}$ is independently selected from H and lower alkyl;

each $R^{13}$ is independently selected from H and lower alkyl;

additionally or alternatively, an $R^{12}$ and an $R^{13}$ attached to the same carbon atom may be taken together to form a $C_3$-$C_6$ cycloalkyl group;

W is a 3- to 7-membered heterocyclic ring having 1 to 3 ring heteroatoms;

c is 2 to 4;

d is 1 to 4;

$R^2$ is selected from the group consisting of aryl, heteroaryl, aralkyl, and heterocyclyl, each of which may be unsubstituted or optionally substituted with 1 to 3 substituents independently selected from the group consisting of halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, $RO_2C$—, aryl-O— and heteroaryl-O—;

alternatively, $R^1$ and $R^2$ taken together form a monocyclic group or a bicyclic group, wherein the monocyclic group has 4 to 7 ring atoms, including up to 2 ring heteroatoms, and the bicyclic group has 8 to 10 ring atoms, including up to 3 ring heteroatoms, and wherein the monocyclic group and bicyclic group are unsubstituted or are optionally substituted with 1 to 3 substituents independently selected from the group consisting of halo, hydroxy, lower alkyl, lower alkoxy, amino, nitro, cyano, $C_1$-$C_3$ perfluoro alkyl, $C_1$-$C_3$ perfluoro alkoxy, carboxyl, aryl and heteroaryl;

$R^3$ is selected from H, lower alkyl, substituted lower alkyl, and RR'N—($C_{2-4}$ alkyl)-;

$R^4$ is selected from the group consisting of H, halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, RR'N—($C_{2-4}$ alkyl)-, and RR'N—($C_{2-4}$ alkyl)-O—;

$R^5$ is selected from H, lower alkyl and $C_3$-$C_6$ cycloalkyl;

alternatively, $R^3$ and $R^5$ taken together form a cyclic group having 5 to 7 ring atoms, including 2-3 ring heteroatoms, wherein the cyclic group is unsubstituted or is optionally substituted with 1 to 3 substituents independently selected from the group consisting of halo, hydroxy, lower alkyl, lower alkoxy, amino, nitro, cyano, $C_1$-$C_3$ perfluoro alkyl, $C_1$-$C_3$ perfluoro alkoxy, carboxyl, aryl and heteroaryl;

a is 0 or 1;

b is 0 to 2;

and each R and R' is independently selected from H, lower alkyl, and $C_3$-$C_6$ cycloalkyl, or alternatively, R and R' taken together form a 5 to 6 membered heterocyclic ring.

The present invention includes pharmaceutical compositions comprising the compounds of the invention and a pharmaceutically acceptable carrier.

The present invention includes compositions comprising a substantially pure compound of the invention and a pharmaceutically acceptable salt, stereoisomer, or hydrate thereof, and a pharmaceutically acceptable carrier.

In one aspect, the invention provides a method of inhibiting a ROCK in a mammal comprising administering an effective amount of one or more compounds of Formula I. The invention provides a method of treating a patient suffering from a disease comprising administering to the patient in need of such treatment a therapeutically effective amount of a compound of Formula I. In certain such embodiments, the compound of Formula I inhibits ROCK2. In certain such embodiments, the compound of Formula I selectively inhibits ROCK2. Non-limiting diseases and conditions treated according to the instant invention include central nervous system disorders such as neuronal degeneration and spinal cord injury, cardiovascular diseases such as hypertension, atherosclerosis, restenosis, cardiac hypertrophy, ocular hypertension, cerebral ischemia, cerebral vasospasm, penile erectile dysfunction, arterial thrombotic disorders such as platelet aggregation and leukocyte aggregation, asthma, regulation of intraocular pressure, and bone resorption. In neoplasias, inhibition of ROCK inhibits tumor cell growth and metastasis, and angiogenesis.

The invention provides a method of treating a central nervous system disorder in a subject comprising administering to the subject a therapeutically effective amount of a compound of Formula I. Central nervous system disorders include, without limitation, neuronal degeneration or spinal cord injury, as well as Huntington's disease, Parkinson's disease, Alzheimer's disease, Amyotrophic lateral sclerosis (ALS), or multiple sclerosis.

The invention provides a method of treating an autoimmune disorder in a subject comprising administering to the subject a therapeutically effective amount of a compound of Formula I. Autoimmune disorders include, without limitation, rheumatoid arthritis, (multiple sclerosis), systemic lupus erythematosus (SLE; lupus), psoriasis, Crohn's disease, atopic dermatitis, eczema, or graft-versus-host disease (GVHD).

The invention provides a method of treating a cardiovascular disorder in a subject comprising administering to the subject a therapeutically effective amount of a compound of Formula I. Cardiovascular disorders include, without limitation, hypertension, atherosclerosis, angina, arterial obstruction, peripheral arterial disease, peripheral circulatory disorder, cerebral cavernous malformation, restenosis, cardiac hypertrophy, ocular hypertension, cerebral ischemia, cerebral vasospasm, acute respiratory distress syndrome (ARDS) or erectile dysfunction.

The invention provides a method of treating inflammation in a subject comprising administering to the subject a therapeutically effective amount of a compound of Formula I. Inflammation includes, without limitation, asthma, cardiovascular inflammation, renal inflammation or arteriosclerosis.

The invention provides a method of treating an arterial thrombotic disorder in a subject comprising administering to the subject a therapeutically effective amount of a compound of Formula I. Non-limiting examples of arterial thrombotic disorders are platelet aggregation, or leukocyte aggregation.

The invention provides a method of treating a fibrotic disorder in a subject comprising administering to the subject a therapeutically effective amount of a compound of Formula I. Non-limiting examples of fibrotic disorders are pulmonary fibrosis including cystic and idiopathic pulmonary fibrosis, radiation induced lung injury, liver fibrosis including cirrhosis, cardiac fibrosis including arterial fibrosis, endomyocardial fibrosis, old myocardial infraction, arterial stiffness, atherosclerosis, restenosis, arthrofibrosis, Crohn's disease, myelofibrosis, Peyronie's diseases, nephrogenic systemic fibrosis, progressive massive fibrosis, retroperitoneal cavity fibrosis, schleroderma/systemic sclerosis, mediastinal fibrosis, Keloids and hypertrophic scars, glial scaring, or renal fibrosis.

The invention provides a method of maintaining epithelial stability comprising administering to the subject a therapeutically effective amount of a compound of Formula I.

The invention provides a method of treating glaucoma or regulating intraocular pressure in a subject comprising administering to the subject a therapeutically effective amount of a compound of Formula I. Non-limiting examples of glaucoma include primary open-angle glaucoma, acute angle-closure glaucoma, pigmentary glaucoma, neovascular glaucoma, congenital glaucoma, normal tension glaucoma, or secondary glaucoma.

The invention provides a method of treating a neoplastic disease in a subject comprising administering to the subject a therapeutically effective amount of a compound of Formula I. Neoplastic diseases include, without limitation, a lymphoma, carcinoma, leukemia, sarcoma, or blastoma, such as squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, or head and neck cancer.

The invention also provides a method of treating metabolic syndrome, insulin resistance, hyperinsulinemia, type 2 diabetes, or glucose intolerance in a subject comprising administering to the subject a therapeutically effective amount of a compound of Formula I.

Further, the invention provides a method of treating osteoporosis or promoting bone formation a subject comprising administering to the subject a therapeutically effective amount of a compound of Formula I.

The invention provides a method of treating an ocular disorder having an angiogenic component comprising administering to the subject a therapeutically effective amount of a compound of Formula I and an angiogenesis inhibitor. Non-limiting examples of such ocular disorders include age related macular degeneration (AMD), choroidal neovascularization (CNV), diabetic macular edema (DME), iris neovascularization, uveitis, neovascular glaucoma, or retinitis of prematurity (ROP).

BRIEF DESCRIPTION OF THE FIGURES

FIG. 2c, representative images.

FIG. 2e, representative images.

FIG. 3a, representative images of human oligodendrocyte/neuron progenitor cells treated with Aβ1-42 in combination with or without compounds.

DETAILED DESCRIPTION OF THE INVENTION

ROCK Inhibitors

Figure 1A:
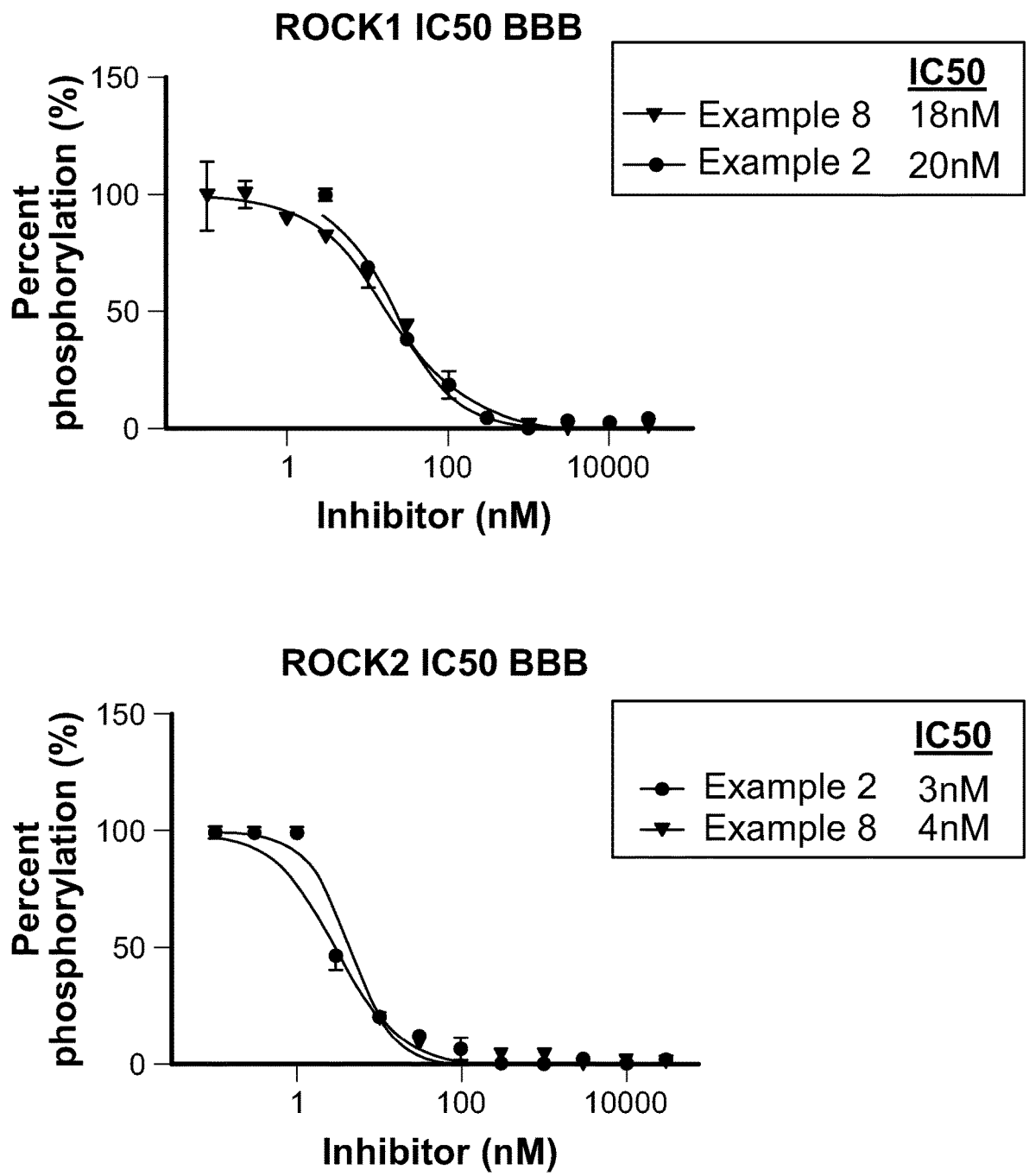
FIG. 1a. Representative Z'-Lyte assay results. The ROCK inhibitors of the present invention show as low as single digit nanomolar potencies towards both isoforms of ROCK.

Compounds according to the present invention include those having the Formula I:

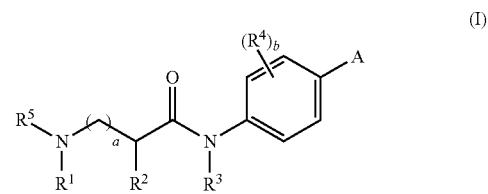

wherein:
A is selected from the group consisting of

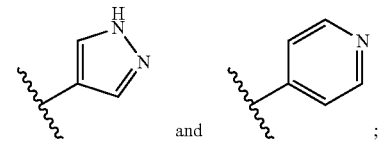 [SMILES: *c1cn[nH]c1 ; *c1ccncc1]

$R^1$ is selected from the group consisting of lower alkyl, substituted lower alkyl, $C_3$-$C_6$ cycloalkyl, substituted $C_3$-$C_6$ cycloalkyl, $R^{10}R^{11}N(CR^{12}R^{13})_c$—, $R^{10}O(CR^{12}R^{13})_c$—, $W(CR^{12}R^{13})_d$— and $R^{10}R^{11}N$—C(=O)—$(CR^{12}R^{13})_c$—;

each $R^{10}$ is independently selected from H, lower alkyl, and $C_3$-$C_6$ cycloalkyl;

each $R^{11}$ is independently selected from H, lower alkyl, and $C_3$-$C_6$ cycloalkyl;

each $R^{12}$ is independently selected from H and lower alkyl;

each $R^{13}$ is independently selected from H and lower alkyl;

additionally or alternatively, an $R^{12}$ and an $R^{13}$ attached to the same carbon atom may be taken together to form a $C_3$-$C_6$ cycloalkyl group;

W is a 3- to 7-membered heterocyclic ring having 1 to 3 ring heteroatoms;

c is 2 to 4;

d is 1 to 4;

$R^2$ is selected from the group consisting of aryl, heteroaryl, aralkyl, and heterocyclyl, each of which may be unsubstituted or optionally substituted with 1 to 3 substituents independently selected from the group consisting of halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, $RO_2C$—, aryl-O— and heteroaryl-O—;

alternatively, $R^1$ and $R^2$ taken together form a monocyclic group or a bicyclic group, wherein the monocyclic group has 4 to 7 ring atoms, including up to 2 ring heteroatoms, and the bicyclic group has 8 to 10 ring atoms, including up to 3 ring heteroatoms, and wherein the monocyclic group and bicyclic group are unsubstituted or are optionally substituted with 1 to 3 substituents independently selected from the group consisting of halo, hydroxy, lower alkyl, lower alkoxy, amino, nitro, cyano, $C_1$-$C_3$ perfluoro alkyl, $C_1$-$C_3$ perfluoro alkoxy, carboxyl, aryl and heteroaryl;

$R^3$ is selected from H, lower alkyl, substituted lower alkyl, and RR'N—($C_{2-4}$ alkyl)-;

$R^4$ is selected from the group consisting of H, halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, RR'N—($C_{2-4}$ alkyl)-, and RR'N—($C_{2-4}$ alkyl)-O—;

$R^5$ is selected from H, lower alkyl and $C_3$-$C_6$ cycloalkyl;

alternatively, $R^3$ and $R^5$ taken together form a cyclic group having 5 to 7 ring atoms, including 2-3 ring heteroatoms, wherein the cyclic group is unsubstituted or is optionally substituted with 1 to 3 substituents independently selected from the group consisting of halo, hydroxy, lower alkyl, lower alkoxy, amino, nitro, cyano, $C_1$-$C_3$ perfluoro alkyl, $C_1$-$C_3$ perfluoro alkoxy, carboxyl, aryl and heteroaryl;

a is 0 or 1;

b is 0 to 2;

and each R and R' is independently selected from H, lower alkyl, and $C_3$-$C_6$ cycloalkyl, or alternatively, R and R' taken together form a 5 to 6 membered heterocyclic ring.

In a certain embodiments of the present invention, there is provided a compound of the formula II:

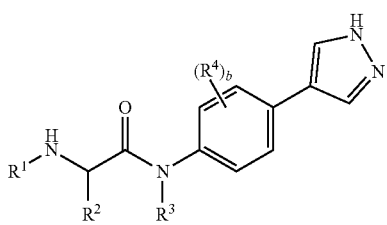

(II)

wherein:

$R^1$ is selected from the group consisting of lower alkyl, substituted lower alkyl, $C_3$-$C_6$ cycloalkyl, substituted $C_3$-$C_6$ cycloalkyl, $R^{10}R^{11}N(CR^{12}R^{13})_c$—, $R^{10}O(CR^{12}R^{13})_c$—, $W(CR^{12}R^{13})_d$— and $R^{10}R^{11}N$—C(=O)—$(CR^{12}R^{13})_c$—;

each $R^{10}$ is independently selected from H, lower alkyl, and $C_3$-$C_6$ cycloalkyl;

each $R^{11}$ is independently selected from H, lower alkyl, and $C_3$-$C_6$ cycloalkyl;

each $R^{12}$ is independently selected from H and lower alkyl;

each $R^{13}$ is independently selected from H and lower alkyl;

additionally or alternatively, an $R^{12}$ and an $R^{13}$ attached to the same carbon atom may be taken together to form a $C_3$-$C_6$ cycloalkyl group;

W is a 3- to 7-membered heterocyclic ring having 1 to 3 ring heteroatoms;

c is 2 to 4;

d is 1 to 4;

$R^2$ is selected from the group consisting of aryl, heteroaryl, aralkyl, and heterocyclyl, each of which may be unsubstituted or optionally substituted with 1 to 3 substituents independently selected from the group consisting of halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, $RO_2C$—, aryl-O— and heteroaryl-O—;

alternatively, $R^1$ and $R^2$ taken together form a monocyclic group or a bicyclic group, wherein the monocyclic group has 4 to 7 ring atoms, including up to 2 ring heteroatoms, and the bicyclic group has 8 to 10 ring atoms, including up to 3 ring heteroatoms, and wherein the monocyclic group and bicyclic group are unsubstituted or are optionally substituted with 1 to 3 substituents independently selected from the group consisting of halo, hydroxy, lower alkyl, lower alkoxy, amino, nitro, cyano, $C_1$-$C_3$ perfluoro alkyl, $C_1$-$C_3$ perfluoro alkoxy, carboxyl, aryl and heteroaryl;

$R^3$ is selected from H, lower alkyl, substituted lower alkyl, and RR'N—($C_{2-4}$ alkyl)-;

$R^4$ is selected from the group consisting of H, halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, RR'N—($C_{2-4}$ alkyl)-, and RR'N—($C_{2-4}$ alkyl)-O—;

b is 0 to 2;

and each R and R' is independently selected from H, lower alkyl, and $C_3$-$C_6$ cycloalkyl, or alternatively, R and R' taken together form a 5 to 6 membered heterocyclic ring.

In a certain embodiments of the present invention, there is provided a compound of the formula III:

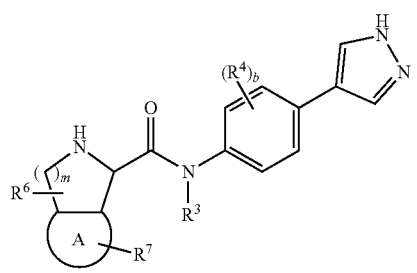

(III)

wherein

Ring A is a 5- or 6-membered aromatic ring which optionally contains 0 to 2 ring heteroatoms;

R³ is selected from H, lower alkyl, substituted lower alkyl, and RR'N—(C$_{2-4}$ alkyl)-;

R⁴ is selected from the group consisting of H, halo, hydroxy, lower alkyl, lower alkoxy, nitro, cyano, C$_1$-C$_3$ perfluoro alkyl, C$_1$-C$_3$ perfluoro alkoxy, carboxyl, RR'N—, RR'NCO—, RCONH—, RCONR'—, RR'N—(C$_{2-4}$ alkyl)-, and RR'N—(C$_{2-4}$ alkyl)-O—;

b is 0 to 2;

R⁶ is selected from the group consisting of H, halo, lower alkyl, substituted lower alkyl, lower alkoxy, amino, hydroxyl, and carboxyl;

R⁷ is selected from the group consisting of H, halo, hydroxy, lower alkyl, lower alkoxy, amino, nitro, cyano, C$_1$-C$_3$ perfluoro alkyl, C$_1$-C$_3$ perfluoro alkoxy, carboxyl, RR'NCO—, RCONH—, and RCONR'—;

each R and R' is independently selected from H, lower alkyl, and C$_3$-C$_6$ cycloalkyl, or alternatively, R and R' taken together form a 5 to 6 membered heterocyclic ring; and m is 1 or 2.

In a certain embodiments of the present invention, there is provided a compound of the formula IV:

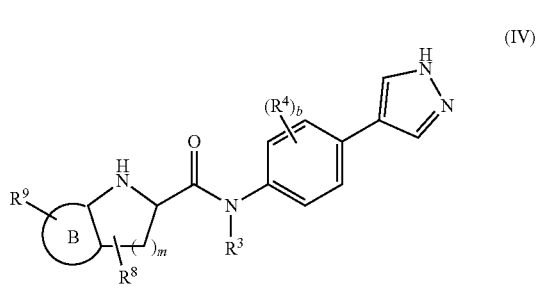

(IV)

wherein

Ring B is a 5- or 6-membered aromatic ring which optionally contains 0 to 2 ring heteroatoms;

R³ is selected from H, lower alkyl, substituted lower alkyl, and RR'N—(C$_{2-4}$ alkyl)-;

R⁴ is selected from the group consisting of H, halo, hydroxy, lower alkyl, lower alkoxy, nitro, cyano, C$_1$-C$_3$ perfluoro alkyl, C$_1$-C$_3$ perfluoro alkoxy, carboxyl, RR'N—, RR'NCO—, RCONH—, RCONR'—, RR'N—(C$_{2-4}$ alkyl)-, and RR'N—(C$_{2-4}$ alkyl)-O—;

b is 0 to 2;

R⁸ is selected from the group consisting of H, halo, lower alkyl, substituted lower alkyl, lower alkoxy, amino, hydroxyl and carboxyl;

R⁹ is selected from the group consisting of H, halo, hydroxy, lower alkyl, lower alkoxy, amino, nitro, cyano, C$_1$-C$_3$ perfluoro alkyl, C$_1$-C$_3$ perfluoro alkoxy and carboxyl, RR'NCO—, RCONH—, and RCONR'—;

each R and R' is independently selected from H, lower alkyl, and C$_3$-C$_6$ cycloalkyl, or alternatively, R and R' taken together form a 5 to 6 membered heterocyclic ring; and m is 1 to 3.

In a certain embodiments of the present invention, there is provided a compound of the formula V:

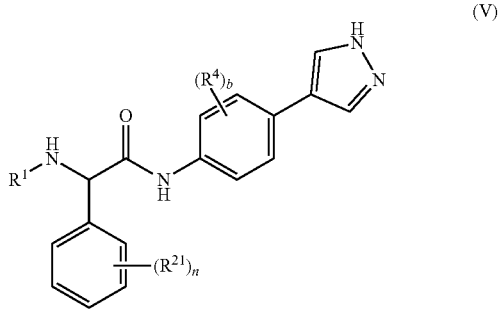

(V)

wherein:

R¹ is selected from the group consisting of lower alkyl, substituted lower alkyl, C$_3$-C$_6$ cycloalkyl, substituted C$_3$-C$_6$ cycloalkyl, R$^{10}$R$^{11}$N(CR$^{12}$R$^{13}$)$_c$—, R$^{10}$O(CR$^{12}$R$^{13}$)$_c$—, W(CR$^{12}$R$^{13}$)$_d$— and R$^{10}$R$^{11}$N—C(=O)—(CR$^{12}$R$^{13}$)$_c$—;

each R¹⁰ is independently selected from H, lower alkyl, and C$_3$-C$_6$ cycloalkyl;

each R¹¹ is independently selected from H, lower alkyl, and C$_3$-C$_6$ cycloalkyl;

each R¹² is independently selected from H and lower alkyl;

each R¹³ is independently selected from H and lower alkyl;

additionally or alternatively, an R¹² and an R¹³ attached to the same carbon atom may be taken together to form a C$_3$-C$_6$ cycloalkyl group;

W is a 3- to 7-membered heterocyclic ring having 1 to 3 ring heteroatoms;

c is 2 to 4;

d is 1 to 4;

R⁴ is selected from the group consisting of H, halo, hydroxy, lower alkyl, lower alkoxy, nitro, cyano, C$_1$-C$_3$ perfluoro alkyl, C$_1$-C$_3$ perfluoro alkoxy, carboxyl, RR'N—, RR'NCO—, RCONH—, RCONR'—, RR'N—(C$_{2-4}$ alkyl)-, and RR'N—(C$_{2-4}$ alkyl)-O—;

b is 0 to 2;

each R²¹ is independently selected from the group consisting of H, halo, hydroxy, lower alkyl, lower alkoxy, nitro, cyano, C$_1$-C$_3$ perfluoro alkyl, C$_1$-C$_3$ perfluoro alkoxy, carboxyl, RR'N—, RR'NCO—, RCONH—, RCONR'—, RO$_2$C—, aryl-O— and heteroaryl-O—;

each R and R' is independently selected from H, lower alkyl, and C$_3$-C$_6$ cycloalkyl, or alternatively, R and R' taken together form a 5 to 6 membered heterocyclic ring; and n is 0 to 3.

In a certain embodiments of the present invention, there is provided a compound of the formula VI:

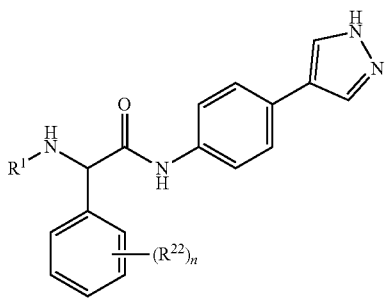

(VI)

wherein:
$R^1$ is selected from the group consisting of lower alkyl, substituted lower alkyl, $C_3$-$C_6$ cycloalkyl, substituted $C_3$-$C_6$ cycloalkyl, $R^{10}R^{11}N(CR^{12}R^{13})_c$—, $R^{10}O(CR^{12}R^{13})_c$—, $W(CR^{12}R^{13})_d$— and $R^{10}R^{11}N$—C(=O)—$(CR^{12}R^{13})_c$—;
each $R^{10}$ is independently selected from H, lower alkyl, and $C_3$-$C_6$ cycloalkyl;
each $R^{11}$ is independently selected from H, lower alkyl, and $C_3$-$C_6$ cycloalkyl;
each $R^{12}$ is independently selected from H and lower alkyl;
each $R^{13}$ is independently selected from H and lower alkyl;
additionally or alternatively, an $R^{12}$ and an $R^{13}$ attached to the same carbon atom may be taken together to form a $C_3$-$C_6$ cycloalkyl group;
W is a 3- to 7-membered heterocyclic ring having 1 to 3 ring heteroatoms;
c is 2 to 4;
d is 1 to 4;
each $R^{22}$ is independently selected from H, halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, $RO_2C$—, aryl-O— and heteroaryl-O—;
each R and R' is independently selected from H, lower alkyl, and $C_3$-$C_6$ cycloalkyl, or alternatively, R and R' taken together form a 5 to 6 membered heterocyclic ring.

In a certain embodiments of the present invention, there is provided a compound of the formula VII:

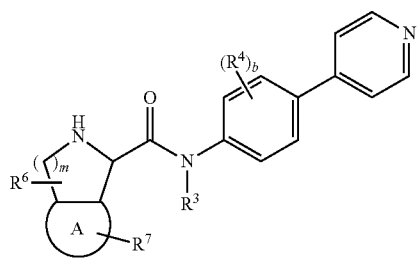

(VII)

wherein:
Ring A is a 5- or 6-membered aromatic ring which optionally contains 0 to 2 ring heteroatoms;
$R^3$ is selected from H, lower alkyl, substituted lower alkyl, and RR'N—($C_{2-4}$ alkyl)-;

$R^4$ is selected from the group consisting of H, halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, RR'N—($C_{2-4}$ alkyl)-, and RR'N—($C_{2-4}$ alkyl)-O—;
b is 0 to 2;
$R^6$ is selected from the group consisting of H, halo, lower alkyl, substituted lower alkyl, lower alkoxy, amino, hydroxyl, and carboxyl;
$R^7$ is selected from the group consisting of H, halo, hydroxy, lower alkyl, lower alkoxy, amino, nitro, cyano, $C_1$-$C_3$ perfluoro alkyl, $C_1$-$C_3$ perfluoro alkoxy, carboxyl, RR'NCO—, RCONH—, and RCONR'—;
each R and R' is independently selected from H, lower alkyl, and $C_3$-$C_6$ cycloalkyl, or alternatively, R and R' taken together form a 5 to 6 membered heterocyclic ring; and
m is 1 or 2.

In a certain embodiments of the present invention, there is provided a compound of the formula VIII:

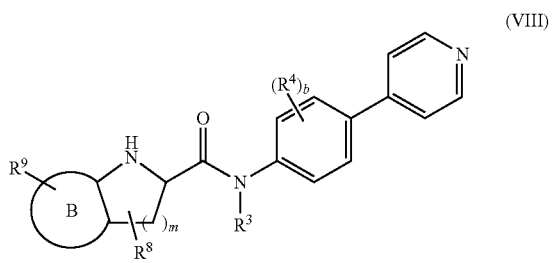

(VIII)

wherein
Ring B is a 5- or 6-membered aromatic ring which optionally contains 0 to 2 ring heteroatoms;
$R^3$ is selected from H, lower alkyl, substituted lower alkyl, and RR'N—($C_{2-4}$ alkyl)-;
$R^4$ is selected from the group consisting of H, halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, RR'N—($C_{2-4}$ alkyl)-, and RR'N—($C_{2-4}$ alkyl)-O—;
b is 0 to 2;
$R^8$ is selected from the group consisting of H, halo, lower alkyl, substituted lower alkyl, lower alkoxy, amino, hydroxyl and carboxyl;
$R^9$ is selected from the group consisting of H, halo, hydroxy, lower alkyl, lower alkoxy, amino, nitro, cyano, $C_1$-$C_3$ perfluoro alkyl, $C_1$-$C_3$ perfluoro alkoxy and carboxyl, RR'NCO—, RCONH—, and RCONR'—;
each R and R' is independently selected from H, lower alkyl, and C3-C6 cycloalkyl, or alternatively, R and R' taken together form a 5 to 6 membered heterocyclic ring; and
m is 1 to 3.

In a certain embodiments of the present invention, there is provided a compound of the formula IX:

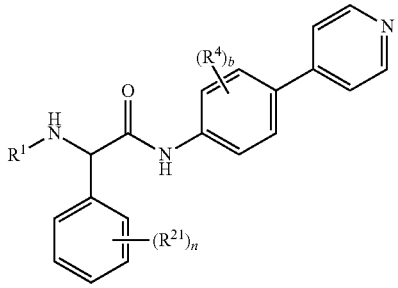

(IX)

wherein:
$R^1$ is selected from the group consisting of lower alkyl, substituted lower alkyl, $C_3$-$C_6$ cycloalkyl, substituted $C_3$-$C_6$ cycloalkyl, $R^{10}R^{11}N(CR^{12}R^{13})_c$—, $R^{10}O(CR^{12}R^{13})_c$—, $W(CR^{12}R^{13})_d$— and $R^{10}R^{11}N$—C(=O)—$(CR^{12}R^{13})_c$—;
each $R^{10}$ is independently selected from H, lower alkyl, and $C_3$-$C_6$ cycloalkyl;
each $R^{11}$ is independently selected from H, lower alkyl, and $C_3$-$C_6$ cycloalkyl;
each $R^{12}$ is independently selected from H and lower alkyl;
each $R^{13}$ is independently selected from H and lower alkyl;
additionally or alternatively, an $R^{12}$ and an $R^{13}$ attached to the same carbon atom may be taken together to form a $C_3$-$C_6$ cycloalkyl group;
W is a 3- to 7-membered heterocyclic ring having 1 to 3 ring heteroatoms;
c is 2 to 4;
d is 1 to 4;
$R^4$ is selected from the group consisting of H, halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, RR'N—($C_{2-4}$ alkyl)-, and RR'N—($C_{2-4}$ alkyl)-O—;
b is 0 to 2;
each $R^{21}$ is independently selected from the group consisting of H, halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, $RO_2C$—, aryl-O— and heteroaryl-O—;
each R and R' is independently selected from H, lower alkyl, and $C_3$-$C_6$ cycloalkyl, or alternatively, R and R' taken together form a 5 to 6 membered heterocyclic ring; and
n is 0 to 3.

In a certain embodiments of the present invention, there is provided a compound of the formula X:

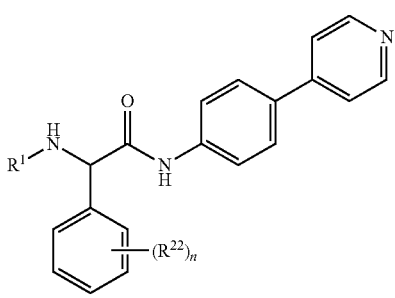

(X)

wherein:
$R^1$ is selected from the group consisting of lower alkyl, substituted lower alkyl, $C_3$-$C_6$ cycloalkyl, substituted $C_3$-$C_6$ cycloalkyl, $R^{10}R^{11}N(CR^{12}R^{13})_c$—, $R^{10}O(CR^{12}R^{13})_c$—, $W(CR^{12}R^{13})_d$— and $R^{10}R^{11}N$—C(=O)—$(CR^{12}R^{13})_c$—;
each $R^{10}$ is independently selected from H, lower alkyl, and $C_3$-$C_6$ cycloalkyl;
each $R^{11}$ is independently selected from H, lower alkyl, and $C_3$-$C_6$ cycloalkyl;
each $R^{12}$ is independently selected from H and lower alkyl;
each $R^{13}$ is independently selected from H and lower alkyl;
additionally or alternatively, an $R^{12}$ and an $R^{13}$ attached to the same carbon atom may be taken together to form a $C_3$-$C_6$ cycloalkyl group;
W is a 3- to 7-membered heterocyclic ring having 1 to 3 ring heteroatoms;
c is 2 to 4;
d is 1 to 4;
each $R^{22}$ is independently selected from the group consisting of halo, hydroxy, lower alkyl, lower alkoxy, amino, $C_1$-$C_3$ perfluoro alkyl, and $C_1$-$C_3$ perfluoro alkoxy; and
n is 0 to 3.

In preferred embodiments for the Formulas I to X, $R^1$ is selected to be lower alkyl or substituted lower alkyl. In certain embodiments, $R^1$ is $C_1$ to $C_3$ alkyl, and still more preferably, $R^1$ is methyl or ethyl.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 8 or fewer carbon atoms in its backbone (e.g., C1-C8 for straight chain, C3-C8 for branched chain), and more preferably 6 or fewer. Likewise, preferred cycloalkyls have from 3-8 carbon atoms in their ring structure, and more preferably have 3 to 6 carbons in the ring structure.

Unless the number of carbons is otherwise specified, "lower alkyl" as used herein means an alkyl group, as defined above, but having from one to four carbons, and more preferably from one to three carbon atoms. In preferred embodiments, a substituent designated herein as alkyl is a lower alkyl. Lower alkyl groups include methyl, ethyl, propyl, isopropyl, n-butyl, iso-butyl, tert-butyl, cyclopropyl and cyclobutyl.

The term "cycloalkyl" refers to saturated, carbocyclic groups having from 3 to 8 carbons in the ring. Cycloalkyl groups include cyclopropyl, cyclobutyl, cyclopentyl and cyclohexyl.

The term "substituted alkyl" refers to an alkyl group as defined above, and having one to three substituents. The substituents are selected from the group consisting of halo, hydroxy, lower alkoxy, amino, lower alkyl amino, nitro, cyano, perfluoro lower alkyl, perfluoro lower alkoxy and carboxyl.

"Substituted lower alkyl" refers to a lower alkyl group as defined above, and having one to three substituents. The substituents are selected from the group consisting of halo, hydroxy, lower alkoxy, amino, nitro, cyano, perfluoro lower alkyl, perfluoro lower alkoxy and carboxyl.

"Substituted cycloalkyl," such as "substituted $C_3$-$C_6$ cycloalkyl" refers to a cycloalkyl group as defined above, and having one to three substituents. The substituents are selected from the group consisting of halo, hydroxy, lower alkyl, lower alkoxy, amino, nitro, cyano, perfluoro lower alkyl, perfluoro lower alkoxy and carboxyl.

As used herein, the term "halogen" or "halo" designates —F, —Cl, —Br or —I, and preferably F, Cl or Br.

The terms "alkoxyl" or "alkoxy" as used herein refers to an alkyl group, as defined above, that is attached through an oxygen atom. Representative alkoxyl groups include methoxy, ethoxy, propyloxy, tert-butoxy and the like. The term "lower alkoxy" refers to an alkoxy substituent in which a lower alkyl is bonded through an oxygen atom, wherein the "lower alkyl" portion is as defined above.

The terms "amine" and "amino" refer to both unsubstituted and substituted amines, e.g., a moiety that can be represented by the general formula:

wherein R and R' are each independently selected from H and lower alkyl.

The term "aryl" as used herein includes 5- and 6-membered single-ring aromatic groups that may include from zero to four heteroatoms, for example, benzene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaryl" groups. The aromatic ring can be substituted at one or more ring positions with such substituents as described above. The term "aryl" also includes polycyclic ring systems having two or more cyclic rings in which two or more carbons are common to two adjoining rings (the rings are "fused rings") wherein at least one of the rings is aromatic.

The term "aralkyl", as used herein, refers to an alkyl group substituted with an aryl group. Preferably, the alkyl group is a lower alkyl, as described above.

The term "heterocycle" of "heterocyclyl" refer to non-aromatic heterocycles having from 4 to 7 ring atoms and including from 1 to 3 ring heteroatoms.

The term "heteroatom" as used herein means an atom of any element other than carbon or hydrogen. Preferred heteroatoms are nitrogen, oxygen, and sulfur. Most preferred are nitrogen and oxygen.

As used herein, the definition of each expression, e.g. alkyl, m, n, $R^1$, $R^2$, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T.W.; Wuts, P.G.M. Protective Groups in Organic Synthesis, 2nd ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are included in this invention. The invention also contemplates the substitution of isotopes of the atoms for the compounds, for example deuterium for hydrogen, etc.

In one aspect, the present invention provides compounds of Formulas I-X that are inhibitors of ROCK. ROCK is found in two forms, ROCK 1 (ROCKβ; p160-ROCK) and ROCK 2 (ROCKα). In some embodiments, the compound of Formulas I-X selectively inhibits ROCK1. In some embodiments, the compound of Formulas I-X selectively inhibits ROCK2. In some embodiments, the compound of Formulas I-X is non-selective with respect to inhibition of ROCK1 and ROCK2. In the context of this invention, selective means the inhibitor demonstrates an $IC_{50}$ that is at least 2-fold, at least 5-fold, at least 10-fold, or at least 25-fold lower for one kinase as compared to the $IC_{50}$ for the other kinase.

Methods of determining kinase inhibition are known in the art. For example, kinase activity of an enzyme and the inhibitory capacity of a test compound can be determined by measuring enzyme specific phosphorylation of a substrate. Commercial assays and kits are available and can be employed. For example, kinase inhibition can be determined using an IMAP® assay (Molecular Devices). This assay method involves the use of a fluorescently tagged peptide substrate. Phosphorylation of the tagged peptide by a kinase of interest promotes binding of the peptide to a trivalent metal-based nanoparticle via the specific, high affinity interaction between the phospho-group and the trivalent metal. Proximity to the nanoparticle results in increased fluorescence polarization. Inhibition of the kinase by a kinase inhibitor prevents phosphorylation of the substrate and thereby limits binding of the fluorescently-tagged substrate to the nanoparticle. Such an assay can be compatible with a microwell assay format, allowing simultaneous determination of $IC_{50}$ of multiple compounds.

Methods of Treating Disease

In one aspect of the present invention there is provided a method of treating a patient suffering from a disease comprising administering to a patient in need of such treatment a therapeutically effective amount of a compound of the present invention. The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment, e.g. reasonable side effects applicable to any medical treatment.

CNS Disorders

Compounds of Formulas I-X demonstrate effective blood brain barrier (BBB) penetration, and distribution to tissues of the central nervous system. Thus, the compounds of the invention are useful for treatment of central nervous system disorders, as well as disorders, such as certain ocular disorders, that benefit from the ability to cross the BBB. Such disorders may involve neuronal degeneration or physical injury to neural tissue, including without limitation, Huntington's disease, Parkinson's Disease, Alzheimer's, Amyotrophic lateral sclerosis (ALS), Batten disease, dementia, spinal muscular atrophy, motor neurone diseases, spinocerebellar ataxia, acute or chronic pain, dementia, neuronal degeneration, spinal cord injury, cerebral vasospasm or multiple sclerosis.

Cardiovascular

Compounds of the invention that inhibit ROCK and/or ROCK mediated phosphorylation are useful for treatment of patients suffering from cardiovascular and non-cardiovascular diseases involving ROCK function, such as hypertension, pulmonary hypertension, atherosclerosis, restenosis, coronary heart disease, cardiac hypertrophy, ocular hypertension, retinopathy, ischemic diseases, cerebral ischemia, cerebral vasospasm, penile erectile dysfunction, peripheral circulatory disorder, peripheral artery occlusive disease, glaucoma, (e.g., regulating intraocular pressure), fibroid lung, fibroid liver, fibroid kidney, chronic obstructive pulmonary disease (COPD), adult respiratory distress syndrome, central nervous system disorders such as neuronal degeneration and spinal cord injury. Further, ROCK inhibiters of the invention can be used to treat arterial thrombotic disorders such as platelet aggregation and leukocyte aggregation, and bone resorption.

In an embodiment of the invention, compounds are used to treat cerebral cavernous malformation (CCM). CCMs are vascular lesions consisting of clusters of leaky, dilated capillaries and are associated with central nervous system (CNS) disorders, including seizures and stroke. The loss of vascular integrity is thought to involve activation of RhoA and activation of ROCK, leading to changes in cytoskeletal stability and increased vascular permeability. The compounds of the invention inhibit ROCK activation and restore vascular endothelial function.

Glaucoma

In an embodiment of the invention, a compound of Formulas I-X is used to treat glaucoma. The two most common, primary open-angle glaucoma and acute angle-closure glaucoma, are characterized by high ocular pressure. Pigmentary glaucoma and congenital glaucoma also are characterized by reduced fluid outflow and high intraocular pressure (TOP). Normal tension glaucoma is thought to be due to another mechanism, in particular poor blood flow to the optic nerve. Secondary glaucoma can result from injury, infection, inflammation, tumor or cataracts, and is also associated with prolonged use of steroids, systemic hypertension, diabetic retinopathy, and central retinal vein occlusion. Glaucomas having a neovascular component can benefit from administration of a angiogenesis inhibitor in addition to a ROCK inhibitor.

Inflammation

The invention provides a method of treating inflammation in a subject comprising administering to the subject a therapeutically effective amount of a compound of Formulas I-X. Inflammation includes, without limitation, asthma, cardiovascular inflammation, renal inflammation, atherosclerosis and arteriosclerosis, and sepsis. Other inflammatory conditions that can be treated by methods of the invention include fibrotic conditions (including, e.g., idiopathic pulmonary fibrosis, NASH, scleroderma, systemic sclerosis, and cirrhosis).

Autoimmune Disorders

The invention provides a method of treating an autoimmune disorder in a subject comprising administering to the subject a therapeutically effective amount of a compound of Formulas I-X. Autoimmune disorders include, without limitation, rheumatoid arthritis, multiple sclerosis, systemic lupus erythematosus (SLE; lupus), psoriasis, Crohn's disease, atopic dermatitis, eczema, or graft-versus-host disease (GVHD), Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis *nodosa*, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, and Vitiligo.

According to the invention, targeting Th17 (IL-17-secreting) cells by ROCK inhibition provides a method for treating Th17 cell-mediated diseases, including but not limited to autoimmune disorders such as RA, MS, SLE, Psoriasis, and Crohn's disease, and GVHD in humans. In an embodiment of the invention, the ROCK inhibitor is a compound of Formulas I-X.

Neoplastic Disease

ROCK inhibitors of the invention inhibit tumor cell growth and metastasis, and angiogenesis, and are useful for treating neoplastic diseases. Neoplastic diseases include any malignant growth or tumor caused by abnormal or uncontrolled cell division, and may spread to other parts of the body through the lymphatic system or the blood stream. Neoplastic disease includes, without limitation, lymphoma (a neoplasm of lymph tissue that is usually malignant), carcinoma (any malignant tumor derived from epithelial tissue), leukemia (malignant neoplasm of blood-forming tissues; characterized by abnormal proliferation of leukocytes), sarcoma (a usually malignant tumor arising from connective tissue (bone or muscle etc.), and blastoma (malignancy in precursor cells). Nonlimiting examples include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer.

Insulin Resistance

In an embodiment of the invention, a ROCK inhibitor is used to reduce or prevent insulin resistance or restore insulin sensitivity. Accordingly, in one embodiment, the compounds of the invention are used to promote or restore insulin-dependent glucose uptake. In another embodiment of the invention, a ROCK-inhibitors of the invention is used to promote or restore glucose tolerance. In another embodiment of the invention, a ROCK inhibitor of the invention is used to treat metabolic syndrome. In another embodiment, a ROCK-inhibitors of the invention is used to reduce or prevent hyperinsulinemia. In an embodiment of the invention, a ROCK inhibitor is used to treat diabetes (particularly type 2 diabetes). ROCK inhibitors of the invention may also be used to promote or restore insulin-mediated relaxation of vascular smooth muscle cells (VSMCs).

Angiogenesis

The invention provides methods and compounds for treating diseases and disorders with an angiogenic component. According to the invention, in certain embodiments, such diseases and disorders are treated by administering to a subject an effective amount of a ROCK inhibitor. According to the invention, such diseases and disorders can also be treated by administering an effective amount of a rho kinase inhibitor and an effective amount of an angiogenesis inhibitor. According to the invention, ocular diseases and disorders having an angiogenic component are treated in this manner. In one embodiment, the invention provides a method of treating age related macular degeneration (AMD), which occurs in "dry" and "wet" forms. The "wet" form of AMD causes vision loss due to abnormal blood vessel growth (neovascularization). Bleeding, leaking, and scarring from these retinal blood vessels eventually causes irreversible damage to the photoreceptors. The dry form results from atrophy of the retinal pigment epithelial layer, which causes vision loss through loss of photoreceptors (rods and cones) in the central part of the eye. In another embodiment, the invention provides a method of treating choroidal neovascularization (CNV). Choroidal neovascularization is a process in which new blood vessels grow in the choroid, through the Bruch membrane and invade the subretinal space, and is a symptom of, among other causes, age-related macular degeneration, myopia and ocular trauma. In another embodiment, the invention provides a method of treating diabetic macular edema (DME). In another embodiment, the invention provides a method of treating macular edema that is secondary to branch retinal vein occlusion (BRVO) or central retinal vein occlusion (CRVO). In other embodiments, the diseases to be treated include, without limitation, retinal neovascularization, infectious and non-infectious, corneal neovascularization infectious and non-infectious, iris neovascularization, uveitis, neovascular glaucoma, and retinitis of prematurity (ROP). The method of treatment can be prophylactic, such as to stave off corneal neovascularization after corneal transplant, or to modulate the wound healing process in trabeculectomy surgery. These diseases and disorders may be characterized as having an angiogenic component. According to the invention, such disorders are treated by administering a ROCK inhibitor, and an angiogenesis inhibitor.

Accordingly, in one such embodiment, the disease or disorder is AMD, and a subject in need of treatment for AMD is administered an amount of a ROCK inhibitor effective to treat AMD. In another embodiment, the subject is administered a ROCK inhibitor and an angiogenesis inhibitor in amounts effective to treat AMD. In some embodiments, the angiogenesis inhibitor is a VEGFR2 antagonist. In certain such embodiments, the VEGFR2 antagonist binds to VEGF. In other such embodiments, the VEGFR2 antagonist binds to VEGFR2. Such VEGFR2-binding inhibitors include agents that bind to the extracellular domain of VEGFR2, including but not limited to antibodies and VEGFR2-binding fragments thereof, and agents that interact with the intracellular domain of VEGFR2 and block activation of VEGFR2-dependent signal transduction. VEGFR2 antagonists further include agents that interact with other cellular components to block VEGFR2-dependent signal transduction. In other embodiments of the invention, other ocular diseases and disorders having an angiogenic component, such as are indicated above, are similarly treated.

According to the invention, a ROCK inhibitor and an angiogenesis inhibitor are administered to a subject in amounts effective amount to treat or preventing a pathologic condition characterized by excessive angiogenesis. Such conditions, involving for example, vascularization and/or inflammation, include atherosclerosis, rheumatoid arthritis (RA), hemangiomas, angiofibromas, and psoriasis. Other non-limiting examples of angiogenic disease are retinopathy of prematurity (retrolental fibroplastic), corneal graft rejection, corneal neovascularization related to complications of refractive surgery, corneal neovascularization related to contact lens complications, corneal neovascularization related to pterygium and recurrent pterygium, corneal ulcer disease, and non-specific ocular surface disease, insulin-dependent diabetes mellitus, multiple sclerosis, myasthenia gravis, Chron's disease, autoimmune nephritis, primary biliary cirrhosis, acute pancreatitis, allograph rejection, allergic inflammation, contact dermatitis and delayed hypersensitivity reactions, inflammatory bowel disease, septic shock, osteoporosis, osteoarthritis, cognition defects induced by neuronal inflammation, Osler-Weber syndrome, restinosis, and fungal, parasitic and viral infections, including cytomegaloviral infections.

The invention provides pan-ROCK inhibitors (i.e., compounds that inhibit ROCK1 and ROCK2). One study observed that ROCK2 is frequently over expressed in hepatocellular cancer compared to non-timorous livers while ROCK1 expression is unaltered. Other cancers that may benefit from treatment with a ROCK2 selective inhibitor include, but are not limited to, colon and bladder cancer. In contrast, ROCK1 expression levels have been observed to be higher in mammary tumors. Any cancer may be tested to determine whether there is overexpression of ROCK1 and/or ROCK2 and treated accordingly. In certain circumstances, ROCK 1 and ROCK2 isoforms show similarity in regulating certain downstream targets and neither isoform seems to be predominant. In such cases, a pan-ROCK inhibitor may be preferred.

Combinations with Other Agents

Compounds of the invention can be advantageously administered with second agents to patients in need thereof. When ROCK inhibitor is administered with a second agent, the ROCK inhibitor and the second agent can be administered sequentially or concomitantly. Sequentially means that one agent is administered for a time followed by administration of the other agent, which may be followed by administration of the first agent. When agents are administered sequentially, the level of one agent may not be maintained at a therapeutically effective level when the second agent is administered, and vice versa. Concomitantly means that the first and second agents are administered according to a schedule that maintains both agents at a substantially therapeutically effective level, even though the agents are not administered simultaneously. Each agent can be administered in single or multiple doses, and the doses can be administered on any schedule, including, without limitation, twice daily, daily, weekly, every two weeks, and monthly.

The invention also includes adjunctive administration. Adjunctive administration means that a second agent is administered to a patient in addition to a first agent that is already being administered to treat a disease or disease symptom. In some embodiments, adjunctive administration involves administering a second agent to a patient in which administration of the first agent did not sufficiently treat a disease or disease symptom. In other embodiments, adjunctive administration involves administration of the second agent to a patient whose disease has been effectively treated by administration of the first agent, with the expectation that the adjunctive treatment improves the outcome of the treatment. In some embodiments, the effect of administering the first and second agents is synergistic. In some embodiments, administration of the first and second agents prevents or lengthens the time until relapse, compared to administration of either of the agents alone. In some embodiments, administration of the first and second agents allows for reduced dosage and/or frequency of administration of the first and second agent.

Anti-inflammatories and immunosuppressants that can be administered in combination with the compounds of the present invention include steroid drugs such as glucocorticoids (e.g., dexamethasone), FK506 (tacrolimus), ciclosporin, fingolimod, interferon, such as IFNβ or IFNγ, a tumor necrosis factor-alpha (TNF-α) binding protein such as infliximab (Remicade), etanercept (Enbrel), or adalimumab (Humira), mycophenolic acid, MMF, Methotrexate, NSAID, Statins, Sirolimus/temsirolimus/everolimus, abatacept (Orencia), anakinra (Kineret), certolizumab (Cimzia). golimumab (Simponi), ixekizumab (Taltz), natalizumab (Tysabri), rituximab (Rituxan), secukinumab (Cosentyx), tocilizumab (Actemra), ustekinumab (Stelara), vedolizumab (Entyvio), basiliximab (Simulect), daclizumab (Zinbryta), muromonab (Orthoclone OKT3), Jakafi (Ruxolitinib), Xeljanz (Tofacitnib), and Otezla (Apremilast).

In an embodiment of the invention, a ROCK inhibitor of the invention and an anti-neoplastic agent are administered to a subject in need thereof. In another embodiment, a ROCK inhibitor of the invention and an angiogenesis inhibitor are administered to a subject in need thereof. In another embodiment, a ROCK inhibitor of the invention and an anti-inflammatory agent are administered to a subject in need thereof. In yet another embodiment, a ROCK inhibitor of the invention and an immunosuppressant are administered. The second agent can be, without limitation, a small molecule, an antibody or antigen binding fragment thereof, or radiation.

Antineoplastic agents include, without limitation, cytotoxic chemotherapeutic agents, targeted small molecules and biological molecules, and radiation. Compounds and agents that can be administered for oncological treatment, in addition to a ROCK inhibitor of the invention, include the following: irinotecan, etoposide, camptothecin, 5-fluorouracil, hydroxyurea, tamoxifen, paclitaxel, capcitabine, carboplatin, cisplatin, bleomycin, dactomycin, gemcitabine, doxorubicin, danorubicin, cyclophosphamide, and radiotherapy, which can be external (e.g., external beam radiation therapy (EBRT)) or internal (e.g., brachytherapy (BT)).

Targeted small molecules and biological molecules include, without limitation, inhibitors of components of signal transduction pathways, such as modulators of tyrosine kinases and inhibitors of receptor tyrosine kinases, and agents that bind to tumor-specific antigens. Examples include inhibitors of epidermal growth factor receptor (EGFR), including gefitinib, erlotinib, and cetuximab, inhibitors of HER2 (e.g., trastuzumab, trastuzumab emtansine (trastuzumab-DM1; T-DM1) and pertuzumab), anti-VEGF antibodies and fragments (e.g., bevacizumab), antibodies that inhibit CD20 (e.g., rituximab, ibritumomab), anti-VEGFR antibodies (e.g., ramucirumab (IMC-1121B), IMC-1C11, and CDP791), anti-PDGFR antibodies, and imatinib. Small molecule kinase inhibitors can be specific for a particular tyrosine kinase or be inhibitors of two or more kinases. For example, the compound N-(3,4-dichloro-2-fluorophenyl)-7-({[(3aR,6aS)-2-methyloctahydrocyclopenta[c] pyrrol-5-yl]methyl}oxy)-6-(methyloxy)quinazolin-4-amine (also known as XL647, EXEL-7647 and KD-019) is an in vitro inhibitor of several receptor tyrosine kinases (RTKs), including EGFR, EphB4, KDR (VEGFR), Flt4 (VEGFR3) and ErbB2, and is also an inhibitor of the SRC kinase, which is involved in pathways that result in nonresponsiveness of tumors to certain TKIs.

Dasatinib (BMS-354825; Bristol-Myers Squibb, New York) is another orally bioavailable, ATP-site competitive Src inhibitor. Dasatanib also targets Bcr-Abl (FDA-approved for use in patients with chronic myelogenous leukemia (CML) or Philadelphia chromosome positive (Ph+) acute lymphoblastic leukemia (ALL)) as well as c-Kit, PDGFR, c-FMS, EphA2, and Src family kinases. Two other oral tyrosine kinase inhibitor of Src and Bcr-Abl are bosutinib (SKI-606) and saracatinib (AZD0530).

According to the invention, angiogenesis inhibitors can be administered to a subject in conjunction with compounds of the invention. Angiogenesis inhibitors include any substance that inhibits the growth of new blood vessels. For example, angiogenesis inhibitors include antagonists of VEGF, P1GF, and VEGF receptors, including the antibodies disclosed herein. A VEGF antagonist reduces or blocks a function in a cell that is associated with VEGF. A VEGF antagonist may act on VEGF, by binding to VEGF and blocking binding to its receptors and/or may act on another cellular component involved in VEGF-mediated signal transduction. Similarly, a VEGFR2 antagonist is an agent that reduces or blocks VEGFR2-mediated signal transduction by binding to VEGFR2 and blocking ligand binding or interaction with a VEGFR2 substrate, or acts on another cellular component to reduce or block VEGFR2-mediated signal transduction. Thus, angiogenesis inhibitors include anti-VEGFR2 antibodies, and antagonists of, without limitation, VEGF, VEGFR1, VEGFR2, PDGF, PDGFR-β, neuropilin-1 (NRP1), and complement.

Angiogenesis inhibitors include intracellular agents that block signal transduction mediated by, for example, VEGF, PDGF, ligands of VEGF or PDGF receptors, or complement. Intracellular agents that inhibit angiogenesis inhibitors include the following, without limitation. Sunitinib (Sutent; SU11248) is a panspecific small-molecule inhibitor of VEGFR1-VEGFR3, PDGFRα and PDGFRβ, stem cell factor receptor (cKIT), Flt-3, and colony-stimulating factor-1 receptor (CSF-1R). Axitinib (AG013736; Inlyta) is another small molecule tyrosine kinase inhibitor that inhibits VEGFR-1-VEGFR-3, PDGFR, and cKIT. Cediranib (AZD2171) is an inhibitor of VEGFR-1-VEGFR-3, PDGFRβ, and cKIT. Sorafenib (Nexavar) is another small molecular inhibitor of several tyrosine protein kinases, including VEGFR, PDGFR, and Raf kinases. Pazopanib (Votrient; (GW786034) inhibits VEGFR-1, -2 and -3, cKIT and PDGFR. Foretinib (GSK1363089; XL880) inhibits VEGFR2 and MET. CP-547632 is as a potent inhibitor of the VEGFR-2 and basic fibroblast growth factor (FGF) kinases. E-3810 ((6-(7-((1-aminocyclopropyl) methoxy)-6-methoxyquinolin-4-yloxy)-N-methyl-1-naphthamide) inhibits VEGFR-1, -2, and -3 and FGFR-1 and -2 kinases in the nanomolar range. Brivanib (BMS-582664) is a VEGFR-2 inhibitor that also inhibits FGF receptor signaling. CT-322 (Adnectin) is a small protein based on a human fibronectin domain and binds to and inhibits activation of VEGFR2. Vandetanib (Caprelas; Zactima; ZD6474) is an inhibitor of VEGFR2, EGFR, and RET tyrosine kinases. X-82 (Xcovery) is a small molecule indolinone inhibitor of signaling through the growth factor receptors VEGFR and PDGFR Pharmaceutical Compositions In one aspect, the present invention provides pharmaceutically acceptable compositions which comprise a therapeutically-effective amount of one or more of the compounds of Formulas I-X, formulated together with one or more pharmaceutically excipients. As described below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals with toxicity, irritation, allergic response, or other problems or complications, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5)

malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, e.g., Berge et al. (1977) "Pharmaceutical Salts", J. Pharm. Sci. 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, e.g., Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable excipients including a pharmaceutically-acceptable carrier, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides diluents, the oral compositions can also include additional excipients such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain additional excipients such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Routes of Administration and Dose

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

In certain embodiments, a dose of a compound or a composition is administered to a subject every day, every other day, every couple of days, every third day, once a week, twice a week, three times a week, or once every two weeks. If desired, the effective daily dose of the active compound may be administered as two, three, four, five, six or more sub-doses administered separately at appropriate intervals throughout the day, optionally, in unit dosage forms. In some embodiments, a dose(s) of a compound or a composition is administered for 2 days, 3 days, 5 days, 7 days, 14 days, or 21 days. In certain embodiments, a dose of a compound or a composition is administered for 1 month, 1.5 months, 2 months, 2.5 months, 3 months, 4 months, 5 months, 6 months or more.

The above-described administration schedules are provided for illustrative purposes only and should not be considered limiting. A person of ordinary skill in the art will readily understand that all doses are within the scope of the invention.

The patient receiving this treatment is any animal in need, including primates, in particular humans, and other mammals such as equines, cattle, swine and sheep; and poultry and pets in general.

The compounds for use in the methods of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutic effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

Microemulsification technology may be employed to improve bioavailability of lipophilic (water insoluble) pharmaceutical agents. Examples include Trimetrine (Dordunoo, S. K., et al., Drug Development and Industrial Pharmacy, 17(12), 1685-1713, 1991) and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

Controlled Release

The release characteristics of a formulation of the present invention depend on the encapsulating material, the concentration of encapsulated drug, and the presence of release modifiers. Release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients that modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

It is to be understood and expected that variations in the principles of invention herein disclosed can be made by one skilled in the art and it is intended that such modifications are to be included within the scope of the present invention. The following Examples further illustrate the invention, but should not be construed to limit the scope of the invention in any way. All references cited herein are hereby incorporated by reference in their entirety.

EXAMPLES

Example 1

All solvents and reagents were obtained commercially and used as received. $^1$H NMR spectra were recorded on a Bruker instrument (300 MHz or 400 MHz) in the cited deuterated solvents. Chemical shifts are given in ppm, and coupling constants are in hertz. All final compounds were purified by flash chromatography using 220-400 mesh silica gel or reverse-phase HPLC with $CH_3CN$/water as the solvents. Thin-layer chromatography was done on silica gel 60 F-254 (0.25-nm thickness) plates. Visualization was accomplished with UV light and/or 10% phosphomolybdic acid in ethanol. Nominal (low resolution) mass spectra were acquired on either a Waters LCT or an Applied Biosystems API 3000 mass spectrometer. High resolution mass spectra (FIRMS) were acquired on either a Waters LCT or an Agilent TOF mass spectrometer. All other LC-MS experiments were done on an Agilent 1100 HPLC coupled with an Agilent single quadrupole mass spectrometer. Compound purity was determined by a LC-MS with 230 nM and 254 nM wavelengths. All final compounds reported here have purity ≥95%.

General Procedure A

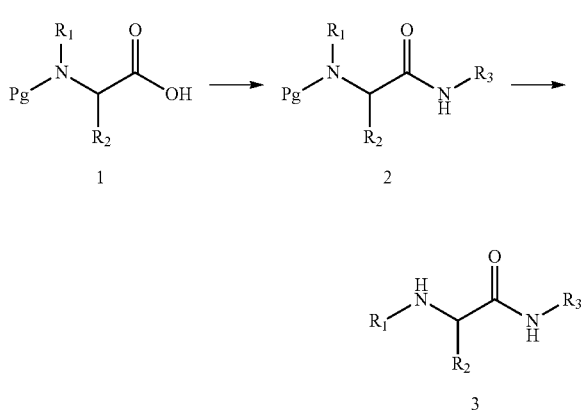

EDCI coupling: compound of general structure 1 (1 equiv), EDCI (1 equiv), HOBt (0.2 equiv) and DIEA (2 equiv) were dissolved in DMF stirred at 25° C. for 5 min. Then to the mixture was added amine (1 equiv). The mixture was stirred at 25° C. for 16 hr. The mixture was poured into water and extracted with EtOAc. Combined organic phases were washed with brine, dried over $Na_2SO_4$, filtered and concentrated under reduced pressure to give a residue. The residue was purified by column chromatography to afford compound of general structure 2.

HATU coupling: compound of general structure 1 (1 equiv), HATU (1.25 equiv) and DIPEA (1.5 equiv) were dissolved in DMF stirred at 23° C. for 15 minutes. 1H-indazol-5-amine (1 equiv) was introduced to the reaction mixture and solution continued to stir at 23° C. for another 16 hours. Reaction mixture was diluted with water and extracted with EtOAc. Combined organic layers were washed with brine, dried over $Na_2SO_4$, filtered and concentrated under reduced pressure to give crude material, which was purified on silica gel to afford the desired compound of general structure 2.

Boc-deprotection: compound of general structure 2 was dissolved in DCM and 4N HCl in dioxane was introduced to the solution. Reaction mixture was stirred at 23° C. for 1 hour. Reaction mixture was concentrated under reduced pressure to give a crude reaction mixture, which was purified via reverse phase preparative HPLC to afford the desired compound of general structure 3.

Benzyl group removal: compound of general structure 2 (1 equiv) and conc. HCl (1.2 equiv) were dissolved in MeOH and 10% dry Pd/C added. Reaction mixture was stirred under an atmosphere of $H_2$ (1 atm) at 50° C. for 5 hours. The reaction mixture was filtered and the filtrate concentrated under reduced pressure to give the crude product which was purified via reverse phase preparative HPLC to afford the desired compound of general structure 3.

General Procedure B

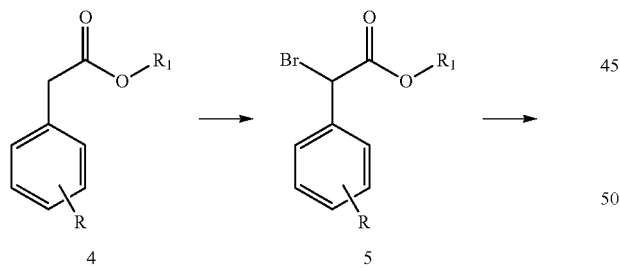

4

5

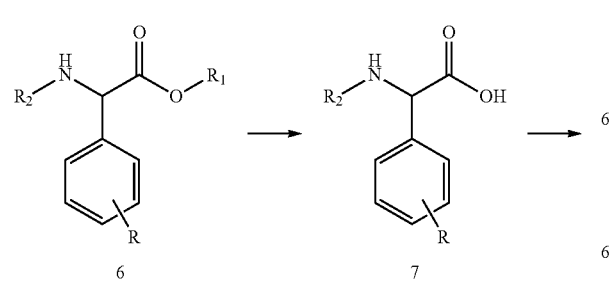

6

7

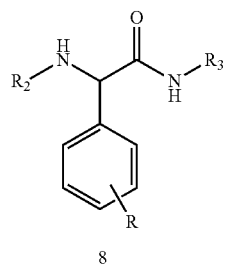

8

Compound of general structure 4 (1 equiv) was dissolved in $CCl_4$ and AIBN (0.1 equiv) followed by NBS (1.2 equiv) were added at room temperature. The reaction temperature was raised to 60° C. and stirring continued for 16 hours. Reaction mixture was filtered off and solvent removed under reduced pressure. Crude material 5 was used in the next step without additional purification.

Compound of general structure 5 (1 equiv) and alkyl amine (2 equiv) in THF was stirred at 70° C. for 16 hours. The reaction mixture was concentrated to under reduced pressure and material purified via silica gel chromatography to afford a compound of general structure 6.

NaOH (2 equiv) was introduced to a reaction vessel containing compound of general structure 6 (1 equiv) dissolved in $MeOH/H_2O$ mixture. Reaction was stirred at 20° C. for 16 hours. Solvent was removed under reduce pressure. The crude residue was dissolved in water (10 mL) and neutralized with 6 N HCl carefully until pH=8. The suspension was filtered and solids were collected and dried to afford compound of general structure 7.

Compound general of structure 7 (1 equiv), HATU (1.25 equiv) and DIPEA (2 equiv) were dissolved in DMF and stirred at 20° C. for 15 minutes. 1H-indazol-5-amine (1 equiv) was introduced to the reaction mixture and stirred at 20° C. for 15.8 hours. Reaction diluted with water and extracted with EtOAc. Combined organic layers were washed with brine (15 mL), dried over $Na_2SO_4$, filtered and concentrated under reduced pressure. Crude reaction mixture purified via reverse phase preparative HPLC to afford compound of general structure 8.

Example 2

N-(4-(1H-pyrazol-4-yl)phenyl)-2-(3-methoxyphenyl)-2-(methylamino)acetamide

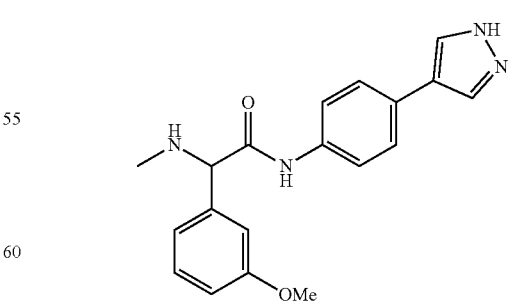

The reaction was conducted following general protocol A. The final residue was purified by reverse phase preparative HPLC to afford N-(4-(1H-pyrazol-4-yl)phenyl)-2-(3-methoxyphenyl)-2-(methylamino)acetamide as a white solid (77%). ¹H NMR (400 MHz, DMSO-d₆) δ 10.09 (brs, 1H), 8.20 (s, 1H), 7.99 (s, 2H), 7.62 (d, J=8.8 Hz, 2H), 7.53 (d, J=8.4 Hz, 2H), 7.27 (t, J=8.0 Hz, 1H), 7.08-7.04 (m, 2H), 6.86 (dd, J=8.0, 2.4 Hz, 1H), 4.23 (s, 1H), 3.76 (s, 3H), 2.30 (s, 3H). MS (ES+) m/e 337.0 (M+H)⁺. [α]D=−97.2 (c=0.5, CH₃OH, 25° C.).

Example 3

(R)—N-(4-(1H-pyrazol-4-yl)phenyl)-2-(3-methoxyphenyl)-2-(methylamino)acetamide

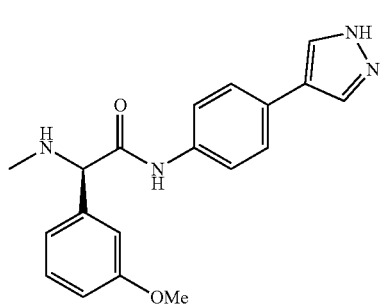 [SMILES: CN[C@@H](C(=O)Nc1ccc(-c2cn[nH]c2)cc1)c1cccc(OC)c1]

The reaction was conducted following general protocol A. The final residue was purified by reverse phase preparative HPLC to afford N-(4-(1H-pyrazol-4-yl)phenyl)-2-(3-methoxyphenyl)-2-(methylamino)acetamide as a white solid (77%). Enantiomers were separated by SFC (Chiralpak AD-H column). Mobile phase: 55% EtOH with 0.1% NH₄OH in CO₂, flow rate 70 g/min. ¹H NMR (400 MHz, DMSO-d₆) δ 10.09 (brs, 1H), 8.20 (s, 1H), 7.99 (s, 2H), 7.62 (d, J=8.8 Hz, 2H), 7.53 (d, J=8.4 Hz, 2H), 7.27 (t, J=8.0 Hz, 1H), 7.08-7.04 (m, 2H), 6.86 (dd, J=8.0, 2.4 Hz, 1H), 4.23 (s, 1H), 3.76 (s, 3H), 2.30 (s, 3H). MS (ES+) m/e 337.0 (M+H)⁺. [α]$_D$=+102.3 (c=0.5, CH₃OH, 25° C.).

Example 4

(S)—N-(4-(1H-pyrazol-4-yl)phenyl)-2-(3-methoxyphenyl)-2-(methylamino)acetamide

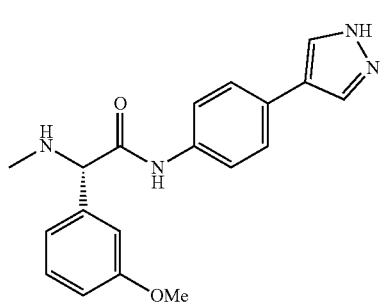 [SMILES: CN[C@H](C(=O)Nc1ccc(-c2cn[nH]c2)cc1)c1cccc(OC)c1]

The reaction was conducted following general protocol A. The final residue was purified by reverse phase preparative HPLC to afford N-(4-(1H-pyrazol-4-yl)phenyl)-2-(3-methoxyphenyl)-2-(methylamino)acetamide as a white solid (77%). Enantiomers were separated by SFC (Chiralpak AD-H column). Mobile phase: 55% EtOH with 0.1% NH₄OH in CO₂, flow rate 70 g/min. ¹H NMR (400 MHz, DMSO-d₆) δ 10.09 (brs, 1H), 8.20 (s, 1H), 7.99 (s, 2H), 7.62 (d, J=8.8 Hz, 2H), 7.53 (d, J=8.4 Hz, 2H), 7.27 (t, J=8.0 Hz, 1H), 7.08-7.04 (m, 2H), 6.86 (dd, J=8.0, 2.4 Hz, 1H), 4.23 (s, 1H), 3.76 (s, 3H), 2.30 (s, 3H). MS (ES+) m/e 337.0 (M+H)⁺. [α]D=−97.2 (c=0.5, CH₃OH, 25° C.).

Example 5

2-(4-chlorophenyl)-2-(methylamino)-N-(4-(pyridin-4-yl)phenyl)acetamide

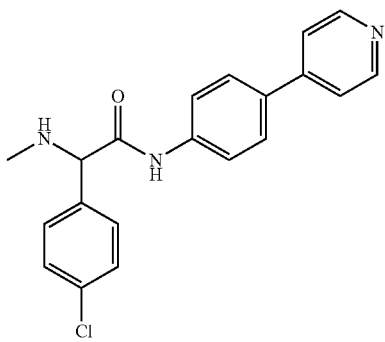 [SMILES: CNC(C(=O)Nc1ccc(-c2ccncc2)cc1)c1ccc(Cl)cc1]

The reaction was conducted following general protocol B. The final residue was purified by reverse phase preparative HPLC to afford 2-(4-chlorophenyl)-2-(methylamino)-N-(4-(pyridin-4-yl)phenyl)acetamide acetamide as a yellow solid (24%). ¹H NMR (400 MHz, DMSO-d₆) δ 11.06 (s, 1H), 9.62 (brs, 2H), 8.78 (d, J=6.4 Hz, 2H), 8.02 (d, J=7.2 Hz, 2H), 7.96 (d, J=8.8 Hz, 2H), 7.77 (d, J=8.8 Hz, 2H), 7.62 (s, 4H), 5.16 (s, 1H), 2.55 (s, 3H). MS (ES+) m/e 352.0 (M+H)⁺.

Example 6

2-(4-methoxyphenyl)-2-(methylamino)-N-(4-(pyridin-4-yl)phenyl)acetamide

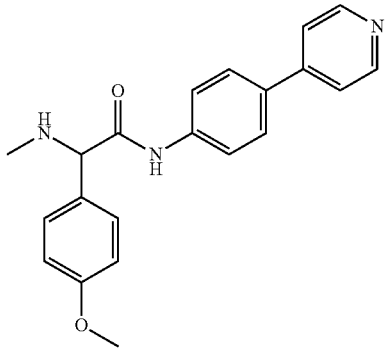 [SMILES: CNC(C(=O)Nc1ccc(-c2ccncc2)cc1)c1ccc(OC)cc1]

The reaction was conducted following general protocol B. The final residue was purified by reverse phase preparative HPLC to afford 2-(4-methoxyphenyl)-2-(methylamino)-N-(4-(pyridin-4-yl)phenyl)acetamide as an off-white solid (16%). ¹H NMR (400 MHz, DMSO-d₆) δ 10.93 (s, 1H), 9.66-9.27 (m, 2H), 8.77 (d, J=6.4 Hz, 2H), 8.02 (d, J=6.4 Hz, 2H), 7.96 (d, J=8.7 Hz, 2H), 7.78 (d, J=8.7 Hz, 2H), 7.52 (d, J=8.8 Hz, 2H), 7.08 (d, J=8.8 Hz, 2H), 5.03 (s, 1H), 3.79 (s, 3H), 2.67 (s, 3H). MS (ES+) m/e 348.0 (M+H)⁺.

Example 7

2-(methyl amino)-N-(4-(pyridin-4-yl)phenyl)-2-(p-tolyl)acetamide

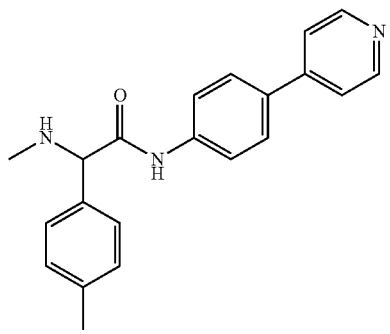 [SMILES: CNC(C(=O)Nc1ccc(-c2ccncc2)cc1)c1ccc(C)cc1]

The reaction was conducted following general protocol B. The final residue was purified by reverse phase preparative HPLC to afford 2-(methylamino)-N-(4-(pyridin-4-yl)phenyl)-2-(p-tolyl)acetamide as a white solid (28%). $^1$H NMR (400 MHz, DMSO-$d_6$) δ 10.25 (brs, 1H), 8.59 (dd, J=4.4, 1.6 Hz, 2H), 8.32 (s, 1H), 7.81-7.76 (m, 4H), 7.68 (dd, J=4.4, 1.6 Hz, 2H), 7.37 (d, J=8.0 Hz, 2H), 7.16 (d, J=8.0 Hz, 2H), 4.21 (s, 1H), 2.29 (s, 3H), 2.28 (s, 3H). MS (ES+) m/e 332.1 (M+H)$^+$.

Example 8

N-(4-(1H-pyrazol-4-yl)phenyl)-2-(2-methoxyphenyl)-2-(methylamino)acetamide

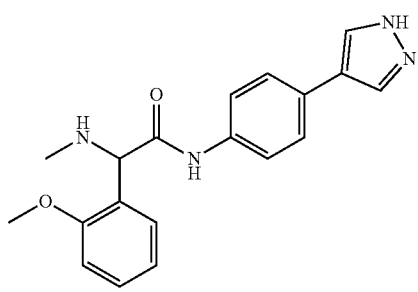 [SMILES: CNC(C(=O)Nc1ccc(-c2cn[nH]c2)cc1)c1ccccc1OC]

The reaction was conducted following general protocol B. The final residue was purified by reverse phase preparative HPLC to afford N-(4-(1H-pyrazol-4-yl)phenyl)-2-(2-methoxyphenyl)-2-(methylamino)acetamide as a white solid (32%). $^1$H NMR (400 MHz, DMSO-$d_6$) δ 9.98 (brs, 1H), 8.21 (s, 1H), 7.99 (s, 2H), 7.64 (d, J=8.4 Hz, 2H), 7.54 (d, J=8.4 Hz, 2H), 7.38 (d, J=7.6 Hz, 1H), 7.30 (t, J=8.0 Hz, 1H), 7.03 (d, J=8.4 Hz, 1H), 6.96 (t, J=7.2 Hz, 1H), 4.58 (s, 1H), 3.82 (s, 3H), 2.33 (s, 3H). MS (ES+) m/e 337.1 (M+H)$^+$.

Example 9

N-(4-(1H-pyrazol-4-yl)phenyl)-2-(4-methoxyphenyl)-2-(methylamino)acetamide

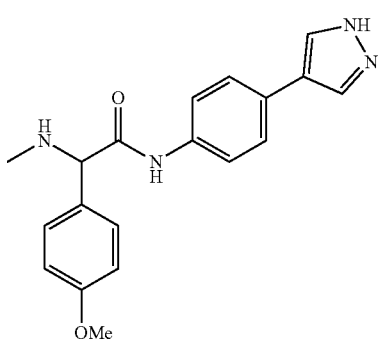 [SMILES: CNC(C(=O)Nc1ccc(-c2cn[nH]c2)cc1)c1ccc(OC)cc1]

The reaction was conducted following general protocol B. The final residue was purified by reverse phase preparative HPLC to afford N-(4-(1H-pyrazol-4-yl)phenyl)-2-(4-methoxyphenyl)-2-(methylamino)acetamide as a white solid (32%). $^1$H NMR (400 MHz, DMSO-$d_6$) δ 10.60 (s, 1H), 9.46-9.30 (m, 2H), 8.01 (s, 2H), 7.59-7.50 (m, 6H), 7.07 (d, J=8.8 Hz, 2H), 4.95-4.94 (m, 1H), 3.79 (s, 3H), 2.54 (s, 3H). MS (ES+) m/e 337.1 (M+H)$^+$.

Example 10

N-(4-(1H-pyrazol-4-yl)phenyl)-2-(ethylamino)-2-(4-methoxyphenyl)acetamide

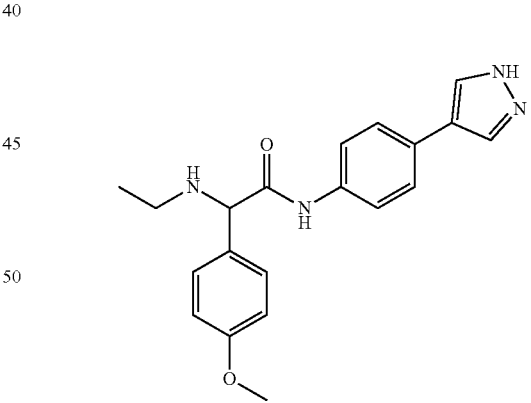

The reaction was conducted following general procedure A. The final residue was purified by reverse phase preparative HPLC to afford N-(4-(1H-pyrazol-4-yl)phenyl)-2-(ethylamino)-2-(4-methoxyphenyl)acetamide as a white solid (16%). $^1$H NMR (400 MHz, CD$_3$OD) δ 8.55 (s, 1H), 7.93 (s, 2H), 7.59-7.51 (m, 6H), 7.04 (d, J=8.8 Hz, 2H), 4.77 (s, 1H), 3.83 (s, 3H), 2.98-2.83 (m, 2H), 1.30 (t, J=7.2 Hz, 3H). MS (ES+) m/e 351.1 (M+H)$^+$.

Example 11

N-(4-(1H-pyrazol-4-yl)phenyl)-2-(ethylamino)-2-(p-tolyl)acetamide

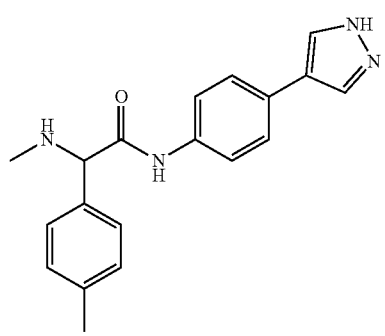 [SMILES: CNC(C(=O)Nc1ccc(-c2cn[nH]c2)cc1)c1ccc(C)cc1]

The reaction was conducted following general procedure A. The final residue was purified by reverse phase preparative HPLC to afford N-(4-(1H-pyrazol-4-yl)phenyl)-2-(ethylamino)-2-(p-tolyl)acetamide as a white solid (8%). $^1$H NMR (400 MHz, DMSO-d$_6$) δ 10.19 (s, 1H), 8.18 (s, 1H), 7.99 (s, 2H), 7.59 (d, J=8.0 Hz, 2H), 7.53 (d, J=8.0 Hz, 2H), 7.38 (d, J=7.6 Hz, 2H), 7.17 (d, J=8.0 Hz, 2H), 4.44 (s, 1H), 2.62-2.54 (m, 2H), 2.28 (s, 3H), 1.09 (t, J=7.2 Hz, 3H). MS (ES+) m/e 335.1 (M+H)$^+$.

Example 12

N-(4-(1H-pyrazol-4-yl)phenyl)-2-(ethylamino)-2-(4-fluorophenyl)acetamide

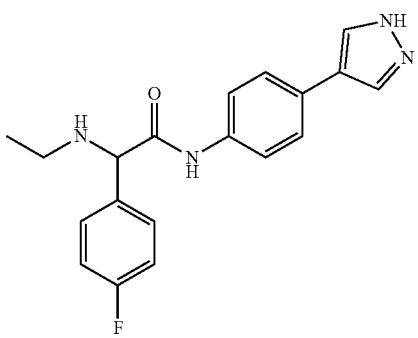 [SMILES: CCNC(C(=O)Nc1ccc(-c2cn[nH]c2)cc1)c1ccc(F)cc1]

The reaction was conducted following general procedure A. The final residue was purified by reverse phase preparative HPLC to afford N-(4-(1H-pyrazol-4-yl)phenyl)-2-(ethylamino)-2-(p-tolyl)acetamide as a white solid (20%). $^1$H NMR (400 MHz, DMSO-d$_6$) δ 10.76 (s, 1H), 9.53-9.47 (m, 2H), 8.01 (s, 2H), 7.69-7.60 (m, 2H), 7.59-7.53 (m, 4H), 7.37 (dd, J=8.8, 8.8 Hz, 2H), 5.14 (s, 1H), 2.96-2.83 (m, 2H), 1.22 (t, J=7.2 Hz, 3H). MS (ES+) m/e 339.0 (M+H)$^+$.

Example 13

N-(4-(1H-pyrazol-4-yl)phenyl)-2-(ethylamino)-2-(3-methoxyphenyl)acetamide

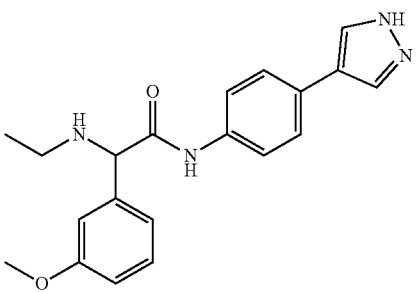 [SMILES: CCNC(C(=O)Nc1ccc(-c2cn[nH]c2)cc1)c1cccc(OC)c1]

The reaction was conducted following general procedure A. The final residue was purified by reverse phase preparative HPLC to afford N-(4-(1H-pyrazol-4-yl)phenyl)-2-(ethylamino)-2-(3-methoxyphenyl)acetamide as a pink solid (20%). $^1$H NMR (400 MHz, DMSO-d$_6$) δ 10.09 (s, 1H), 8.26 (s, 1H), 7.99 (s, 2H), 7.61 (d, J=8.4 Hz, 2H), 7.53 (d, J=8.4 Hz, 2H), 7.26 (t, J=8.0 Hz, 1H), 7.08-7.04 (m, 2H), 6.86-6.84 (m, 1H), 4.33 (s, 1H), 3.76 (s, 3H), 2.56-2.53 (m, 2H), 1.08 (t, J=7.2 Hz, 3H). MS (ES+) m/e 351.1 (M+H)$^+$.

Example 14

N-(4-(1H-pyrazol-4-yl)phenyl)-2-(methylamino)-2-(m-tolyl)acetamide

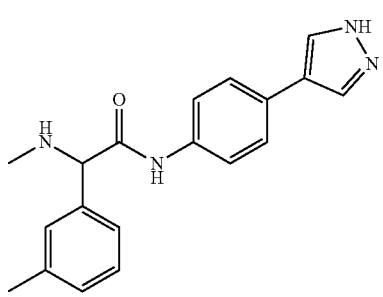 [SMILES: CNC(C(=O)Nc1ccc(-c2cn[nH]c2)cc1)c1cccc(C)c1]

The reaction was conducted following general procedure A. The final residue was purified by reverse phase preparative HPLC to afford N-(4-(1H-pyrazol-4-yl)phenyl)-2-(methylamino)-2-(m-tolyl)acetamide as a white solid (14%). $^1$H NMR (400 MHz, DMSO-d$_6$) δ 10.05 (s, 1H), 8.20 (s, 1H), 7.99 (s, 2H), 7.63-7.61 (m, 2H), 7.54-7.52 (m, 2H), 7.29-7.09 (m, 3H), 7.10 (d, J=6.8 Hz, 1H), 4.18 (s, 1H), 2.31 (s, 3H), 2.28 (s, 3H). MS (ES+) m/e 321.1 (M+H)$^+$.

Example 15

N-(4-(1H-pyrazol-4-yl)phenyl)-2-(ethylamino)-2-(3-fluorophenyl)acetamide

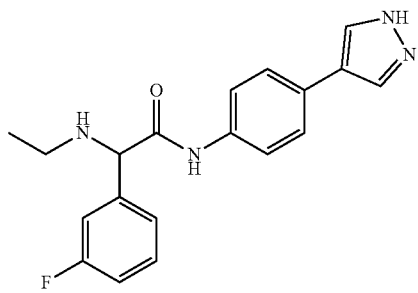 [SMILES: CCNC(C(=O)Nc1ccc(-c2cn[nH]c2)cc1)c1cccc(F)c1]

The reaction was conducted following general procedure A. The final residue was purified by reverse phase preparative HPLC to afford N-(4-(1H-pyrazol-4-yl)phenyl)-2-(ethylamino)-2-(3-fluorophenyl)acetamide as a white solid (20%). $^1$H NMR (400 MHz, DMSO-$d_6$) δ 10.14 (s, 1H), 8.17 (s, 1H), 8.00 (s, 2H), 7.61-7.59 (m, 2H), 7.55-7.53 (m, 2H), 7.43-7.31 (m, 3H), 7.14-7.09 (m, 1H), 4.40 (s, 1H), 2.56-2.53 (m, 2H), 1.07 (t, J=7.2 Hz, 3H). MS (ES+) m/e 339.1 (M+H)$^+$.

Example 16

N-(4-(1H-pyrazol-4-yl)phenyl)-2-(3-chlorophenyl)-2-(ethylamino)acetamide

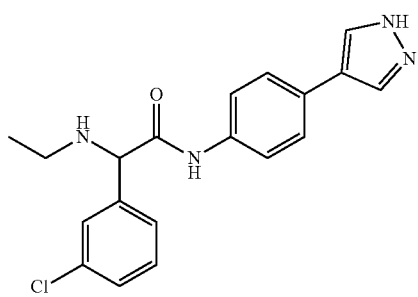 [SMILES: CCNC(C(=O)Nc1ccc(-c2cn[nH]c2)cc1)c1cccc(Cl)c1]

The reaction was conducted following general procedure A. The final residue was purified by reverse phase preparative HPLC to afford N-(4-(1H-pyrazol-4-yl)phenyl)-2-(3-chlorophenyl)-2-(ethylamino)acetamide as a white solid (6%). $^1$H NMR (400 MHz, DMSO-$d_6$) δ 10.14 (s, 1H), 8.19 (s, 1H), 8.00 (s, 2H), 7.62-7.53 (m, 5H), 7.45-7.34 (m, 3H), 4.39 (s, 1H), 2.53 (m, 2H), 1.07 (t, J=7.2 Hz, 3H). MS (ES+) m/e 355.1 (M+H)$^+$.

Example 17

N-(4-(1H-pyrazol-4-yl)phenyl)-2-(4-chlorophenyl)-2-(methylamino)acetamide

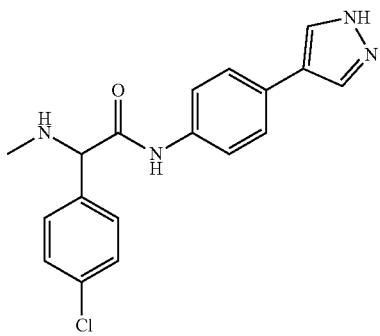 [SMILES: CNC(C(=O)Nc1ccc(-c2cn[nH]c2)cc1)c1ccc(Cl)cc1]

The reaction was conducted following general procedure A. The final residue was purified by reverse phase preparative HPLC to afford N-(4-(1H-pyrazol-4-yl)phenyl)-2-(4-chlorophenyl)-2-(methylamino)acetamide as a white solid (8%). $^1$H NMR (400 MHz, DMSO-$d_6$) δ 10.11 (s, 1H), 8.21 (s, 1H), 7.99 (s, 2H), 7.62-7.60 (m, 2H), 7.54-7.49 (m, 4H), 7.43-7.41 (m, 2H), 4.25 (s, 1H), 2.28 (s, 3H). MS (ES+) m/e 341.0 (M+H)$^+$.

Example 18

N-(4-(1H-pyrazol-4-yl)phenyl)-2-(3-fluorophenyl)-2-(methylamino)acetamide

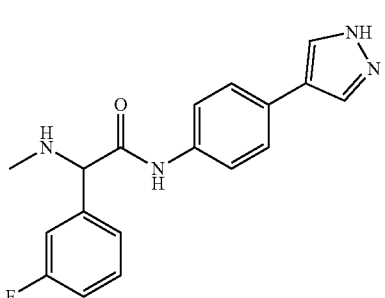

The reaction was conducted following general procedure A. The final residue was purified by reverse phase preparative HPLC to afford N-(4-(1H-pyrazol-4-yl)phenyl)-2-(3-fluorophenyl)-2-(methylamino)acetamide as a white solid (23%). $^1$H NMR (400 MHz, DMSO-$d_6$) δ 10.14 (s, 1H), 8.18 (s, 1H), 7.99 (s, 2H), 7.63-7.60 (m, 2H), 7.55-7.53 (m, 2H), 7.43-7.31 (m, 3H), 7.15-7.10 (m, 1H), 4.30 (s, 1H), 2.29 (s, 3H). MS (ES+) m/e 325.1 (M+H)$^+$.

Example 19

N-(4-(1H-pyrazol-4-yl)phenyl)-2-(4-fluorophenyl)-2-(methylamino)acetamide

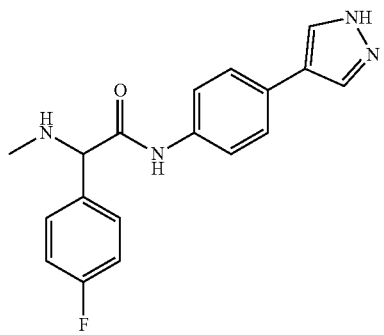 [SMILES: CNC(C(=O)Nc1ccc(-c2cn[nH]c2)cc1)c1ccc(F)cc1]

The reaction was conducted following general procedure A. The final residue was purified by reverse phase preparative HPLC to afford N-(4-(1H-pyrazol-4-yl)phenyl)-2-(4-fluorophenyl)-2-(methylamino)acetamide as an off-white solid (25%). $^1$H NMR (400 MHz, DMSO-d$_6$) δ 10.11 (s, 1H), 8.20 (s, 2H), 7.99 (s, 2H), 7.62-7.50 (m, 6H), 7.21-7.17 (m, 2H), 4.27 (s, 1H), 2.29 (s, 3H). MS (ES+) m/e 325.1 (M+H)$^+$.

Example 20

N-(4-(1H-pyrazol-4-yl)phenyl)-2-(3-chlorophenyl)-2-(methylamino)acetamide

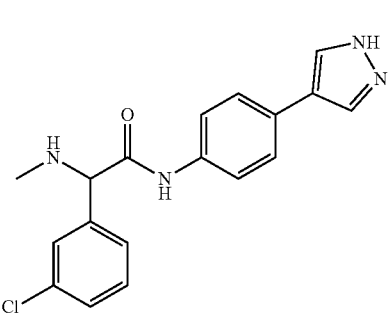 [SMILES: CNC(C(=O)Nc1ccc(-c2cn[nH]c2)cc1)c1cccc(Cl)c1]

The reaction was conducted following general procedure A. The final residue was purified by reverse phase preparative HPLC to afford N-(4-(1H-pyrazol-4-yl)phenyl)-2-(3-chlorophenyl)-2-(methylamino)acetamide as an off-white solid (3%). $^1$H NMR (400 MHz, DMSO-d$_6$) δ 10.13 (s, 1H), 8.33 (s, 2H), 7.99 (s, 2H), 7.63-7.61 (m, 2H), 7.56-7.53 (m, 3H), 7.45-7.34 (m, 3H), 4.26 (s, 1H), 2.28 (s, 3H). MS (ES+) m/e 341.0 (M+H)$^+$.

Example 21

N-(4-(1H-pyrazol-4-yl)phenyl)-2-(methylamino)-2-(p-tolyl)acetamide

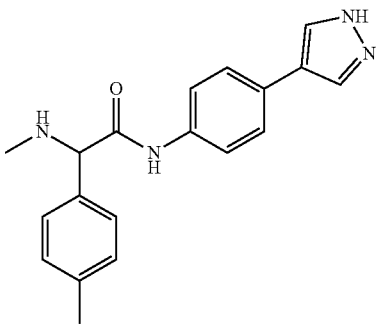 [SMILES: CNC(C(=O)Nc1ccc(-c2cn[nH]c2)cc1)c1ccc(C)cc1]

The reaction was conducted following general procedure A. The final residue was purified by reverse phase preparative HPLC to afford N-(4-(1H-pyrazol-4-yl)phenyl)-2-(methylamino)-2-(p-tolyl)acetamide as a yellow oil (12%). $^1$H NMR (400 MHz, DMSO-d$_6$) δ 12.88 (s, 1H), 10.01 (s, 1H), 8.11 (s, 1H), 7.86 (s, 1H), 7.63-7.61 (m, 2H), 7.54-7.52 (m, 2H), 7.35 (d, J=8.0 Hz, 2H), 7.15 (d, J=8.0 Hz, 2H), 4.16 (s, 1H), 2.28 (s, 6H). MS (ES+) m/e 321.1 (M+H)$^+$.

Example 22

N-(4-(1H-pyrazol-4-yl)phenyl)-2-(4-chlorophenyl)-2-(ethylamino)acetamide

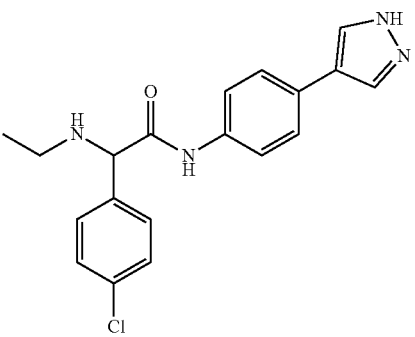 [SMILES: CCNC(C(=O)Nc1ccc(-c2cn[nH]c2)cc1)c1ccc(Cl)cc1]

The reaction was conducted following general procedure A. The final residue was purified by reverse phase preparative HPLC to afford N-(4-(1H-pyrazol-4-yl)phenyl)-2-(4-chlorophenyl)-2-(ethylamino)acetamide as a white solid (6%). $^1$H NMR (400 MHz, DMSO-d$_6$) δ 10.13 (s, 1H), 8.23 (s, 1H), 7.99 (s, 2H), 7.61-7.50 (m, 6H), 7.43-7.41 (m, 2H), 4.38 (s, 1H), 2.57-2.54 (m, 2H), 1.07 (t, J=7.2 Hz, 3H). MS (ES+) m/e 355.1 (M+H)$^+$.

Example 23

N-(4-(1H-pyrazol-4-yl)phenyl)-2-(3-fluoro-4-methoxyphenyl)-2-(methylamino)acetamide

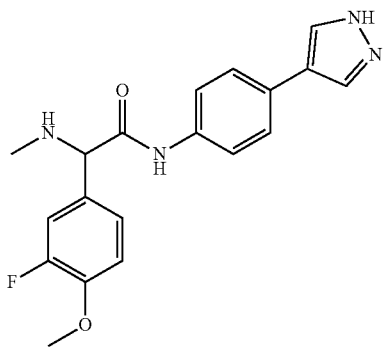 [SMILES: CNC(C(=O)Nc1ccc(-c2cn[nH]c2)cc1)c1ccc(OC)c(F)c1]

The reaction was conducted following general procedure A. The final residue was purified by reverse phase preparative HPLC to afford N-(4-(1H-pyrazol-4-yl)phenyl)-2-(3-fluoro-4-methoxyphenyl)-2-(methylamino)acetamide as a white solid (5%). $^1$H NMR (400 MHz, DMSO-$d_6$) δ 12.86 (s, 1H), 10.03 (s, 1H), 7.99 (s, 2H), 7.60 (d, J=8.8 Hz, 2H), 7.52 (d, J=8.8 Hz, 2H), 7.32 (d, J=12.8 Hz, 1H), 7.23 (d, J=8.8 Hz, 1H), 7.12 (t, J=8.8 Hz, 1H), 4.15 (s, 1H), 3.80 (s, 3H), 2.67 (s, 1H), 2.25 (s, 3H). MS (ES+) m/e 353.2 (M+H)$^+$.

Example 24

N-(4-(1H-pyrazol-4-yl)phenyl)-2-(3-(difluoromethoxy)phenyl)-2-(methylamino)acetamide

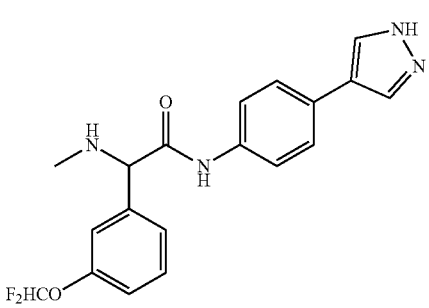 [SMILES: CNC(C(=O)Nc1ccc(-c2cn[nH]c2)cc1)c1cccc(OC(F)F)c1]

The reaction was conducted following general procedure A. The final residue was purified by reverse phase preparative HPLC to afford N-(4-(1H-pyrazol-4-yl)phenyl)-2-(3-(difluoromethoxy)phenyl)-2-(methylamino)acetamide as an off-white solid (18%). $^1$H NMR (400 MHz, DMSO-$d_6$) δ 10.12 (s, 1H), 8.16 (s, 1H), 7.99 (s, 2H), 7.62-7.60 (m, 2H), 7.55-7.53 (m, 2H), 7.44-7.05 (m, 5H), 4.28 (s, 1H), 2.29 (s, 3H). MS (ES+) m/e 373.3 (M+H)$^+$.

Example 25

N-(4-(1H-pyrazol-4-yl)phenyl)-2-((2-methoxyethyl)amino)-2-(3-methoxyphenyl)acetamide

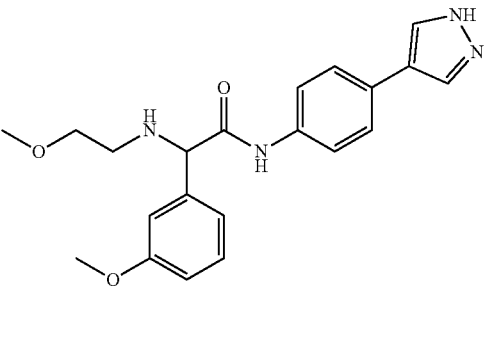 [SMILES: COCCNC(C(=O)Nc1ccc(-c2cn[nH]c2)cc1)c1cccc(OC)c1]

The reaction was conducted following general procedure B. The final residue was purified by reverse phase preparative HPLC to afford N-(4-(1H-pyrazol-4-yl)phenyl)-2-(3-(difluoromethoxy)phenyl)-2-(methylamino)acetamide as a white solid (12%). $^1$H NMR (400 MHz, DMSO-$d_6$) δ 10.18 (s, 1H), 8.16 (s, 1H), 7.99 (s, 2H), 7.61-7.53 (m, 4H), 7.27 (t, J=4.6 Hz, 1H), 7.06-7.03 (m, 2H), 6.87-6.84 (m, 1H), 4.40 (s, 1H), 3.75 (s, 3H), 3.44 (t, J=5.2 Hz, 2H), 3.24 (s, 3H), 2.67 (t, J=5.2 Hz, 2H). MS (ES+) m/e 381.3 (M+H)$^+$.

Example 26

N-(4-(1H-pyrazol-4-yl)phenyl)-2-(3-methoxyphenyl)-2-((2-(methylamino)ethyl)amino)acetamide

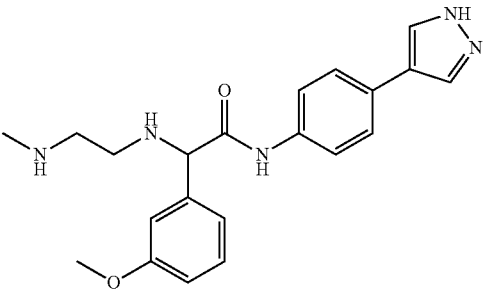 [SMILES: CNCCNC(C(=O)Nc1ccc(-c2cn[nH]c2)cc1)c1cccc(OC)c1]

The reaction was conducted following general procedure B. The final residue was purified by reverse phase preparative HPLC to afford N-(4-(1H-pyrazol-4-yl)phenyl)-2-(3-methoxyphenyl)-2-((2-(methylamino)ethyl)amino)acetamide as a white solid (29%). $^1$H NMR (400 MHz, CD$_3$OD) δ 8.49 (s, 1H), 7.91 (s, 2H), 7.58-7.52 (m, 4H), 7.31 (t, J=8.0 Hz, 1H), 7.10-7.08 (m, 2H), 6.92-6.89 (m, 1H), 4.43 (s, 1H), 3.81 (s, 3H), 3.14-3.04 (m, 2H), 2.92-2.81 (m, 2H), 2.71 (s, 3H). MS (ES+) m/e 380.3 (M+H)$^+$.

Example 27

N-(4-(1H-pyrazol-4-yl)phenyl)-2-(methylamino)-2-(2-methylbenzo[d]thiazol-6-yl)acetamide

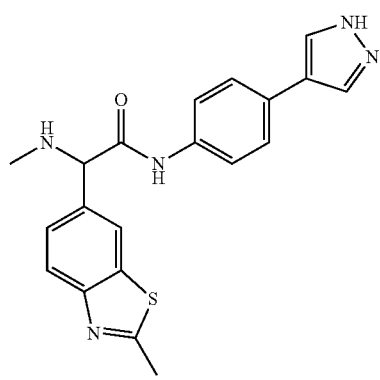 [SMILES: CNC(C(=O)Nc1ccc(-c2cn[nH]c2)cc1)c1ccc2nc(C)sc2c1]

The reaction was conducted following general procedure A. The final residue was purified by reverse phase preparative HPLC to afford N-(4-(1H-pyrazol-4-yl)phenyl)-2-(methylamino)-2-(2-methylbenzo[d]thiazol-6-yl)acetamide as an white solid (6%). ¹H NMR (400 MHz, DMSO-d₆) δ 10.34 (s, 1H), 8.16 (d, J=6.4 Hz, 2H), 8.00-7.94 (m, 3H), 7.63-7.54 (m, 5H), 4.67 (s, 1H), 2.81 (s, 3H), 2.40 (s, 3H). MS (ES+) m/e 378.3 (M+H)⁺.

Example 28

N-(4-(1H-pyrazol-4-yl)phenyl)-2-(3-(dimethylamino)phenyl)-2-(methylamino)acetamide

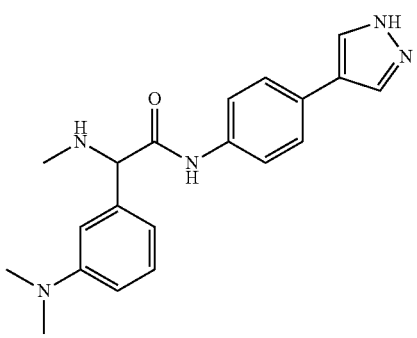 [SMILES: CNC(C(=O)Nc1ccc(-c2cn[nH]c2)cc1)c1cccc(N(C)C)c1]

The reaction was conducted following general procedure A. The final residue was purified by reverse phase preparative HPLC to afford N-(4-(1H-pyrazol-4-yl)phenyl)-2-(3-(dimethylamino)phenyl)-2-(methylamino)acetamide as a yellow solid (17%). ¹H NMR (400 MHz, DMSO-d₆) δ 10.11 (s, 1H), 8.19 (s, 1H), 7.98 (s, 2H), 7.62-7.51 (m, 4H), 7.15 (t, J=8.0 Hz, 1H), 6.87 (s, 1H), 6.76 (d, J=7.2 Hz, 1H), 6.66-6.63 (m, 1H), 4.25 (s, 1H), 2.89 (s, 6H), 2.32 (s, 3H). MS (ES+) m/e 350.3 (M+H)⁺.

Example 29

N-(4-(1H-pyrazol-4-yl)phenyl)-2-(2-methoxypyridin-4-yl)-2-(methylamino)acetamide

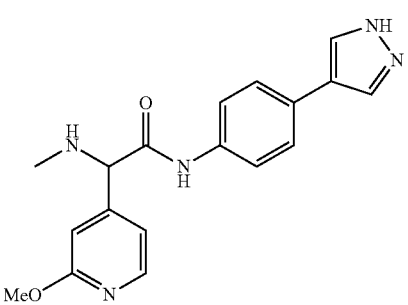 [SMILES: CNC(C(=O)Nc1ccc(-c2cn[nH]c2)cc1)c1ccnc(OC)c1]

The reaction was conducted following general procedure B. The final residue was purified by reverse phase preparative HPLC to afford N-(4-(1H-pyrazol-4-yl)phenyl)-2-(2-methoxypyridin-4-yl)-2-(methylamino)acetamide as a white solid (2%). ¹H NMR (400 MHz, DMSO-d₆) δ 10.12 (s, 1H), 8.15 (s, 1H), 8.12 (d, J=5.6 Hz, 1H), 7.98 (s, 2H), 7.61-7.52 (m, 4H), 7.07 (d, J=4.4 Hz, 1H), 6.91 (s, 1H), 4.24 (s, 1H), 3.83 (s, 3H), 2.28 (s, 3H). MS (ES+) m/e 338.2 (M+H)⁺.

Example 30

Methyl 3-(2-((4-(1H-pyrazol-4-yl)phenyl)amino)-1-(methylamino)-2-oxoethyl)benzoate

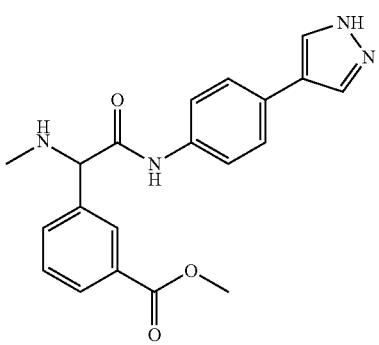 [SMILES: CNC(C(=O)Nc1ccc(-c2cn[nH]c2)cc1)c1cccc(C(=O)OC)c1]

The reaction was conducted following general procedure A. The final residue was purified by reverse phase preparative HPLC to afford methyl 3-(2-((4-(1H-pyrazol-4-yl)phenyl)amino)-1-(methylamino)-2-oxoethyl)benzoate as a white solid (15%). ¹H NMR (400 MHz, DMSO-d₆) δ 10.71 (s, 1H), 9.65-9.51 (m, 2H), 8.25 (s, 1H), 8.07 (d, J=8.0 Hz, 1H), 8.00 (s, 2H), 7.86 (d, J=8.0 Hz, 1H), 7.69 (t, J=7.6 Hz, 1H), 7.59-7.52 (m, 4H), 5.15 (s, 1H), 3.89 (s, 3H), 2.54 (s, 3H). MS (ES+) m/e 365.3 (M+H)⁺.

Example 31

N-(4-(1H-pyrazol-4-yl)phenyl)-2-(4-(dimethylamino)phenyl)-2-(methylamino)acetamide

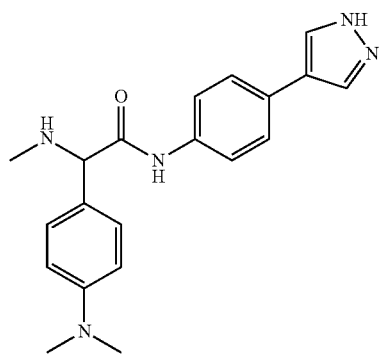 [SMILES: CNC(C(=O)Nc1ccc(-c2cn[nH]c2)cc1)c1ccc(N(C)C)cc1]

The reaction was conducted following general procedure A. The final residue was purified by reverse phase preparative HPLC to afford methyl N-(4-(1H-pyrazol-4-yl)phenyl)-2-(4-(dimethylamino)phenyl)-2-(methylamino)acetamide as a white solid (4%). $^1$H NMR (400 MHz, CD$_3$OD) δ 7.90 (s, 2H), 7.57-7.50 (m, 4H), 7.30 (d, J=8.8 Hz, 2H), 6.76 (d, J=8.8 Hz, 2H), 4.15 (s, 1H), 2.91 (s, 6H), 2.37 (s, 3H). MS (ES+) m/e 350.3 (M+H)$^+$.

Example 32

3-(2-((4-(1H-pyrazol-4-yl)phenyl)amino)-1-(methylamino)-2-oxoethyl)benzoic acid

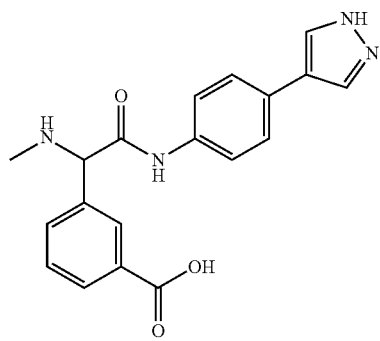 [SMILES: CNC(C(=O)Nc1ccc(-c2cn[nH]c2)cc1)c1cccc(C(=O)O)c1]

The reaction was conducted following general procedure A. The final residue was purified by reverse phase preparative HPLC to afford 3-(2-((4-(1H-pyrazol-4-yl)phenyl)amino)-1-(methylamino)-2-oxoethyl)benzoic acid as a white solid (15%). $^1$H NMR (400 MHz, DMSO-d$_6$) δ 10.15 (s, 1H), 8.23 (s, 1H), 8.07 (s, 1H), 7.98 (s, 2H), 7.86 (d, J=7.6 Hz, 1H), 7.70 (d, J=8.4 Hz, 1H), 7.61 (d, J=8.8 Hz, 2H), 7.53 (d, J=8.4 Hz, 2H), 7.47 (t, J=7.6 Hz, 1H), 4.33 (s, 1H), 2.29 (s, 3H). MS (ES+) m/e 351.3 (M+H)$^+$.

Example 33

N-(4-(1H-pyrazol-4-yl)phenyl)-2-(3-methyl-1H-indazol-6-yl)-2-(methylamino)acetamide

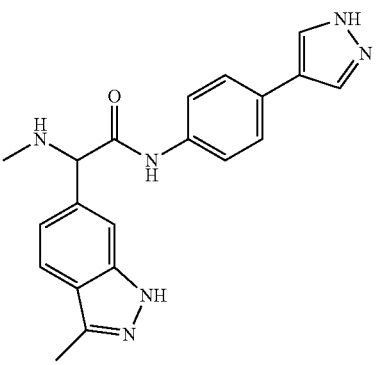 [SMILES: CNC(C(=O)Nc1ccc(-c2cn[nH]c2)cc1)c1ccc2c(C)n[nH]c2c1]

The reaction was conducted following general procedure A. The final residue was purified by reverse phase preparative HPLC to afford N-(4-(1H-pyrazol-4-yl)phenyl)-2-(3-methyl-1H-indazol-6-yl)-2-(methylamino)acetamide as a white solid (8%). $^1$H NMR (400 MHz, CD$_3$OD) δ 7.93 (s, 2H), 7.89 (d, J=8.4 Hz, 1H), 7.78 (s, 1H), 7.58-7.54 (m, 4H), 7.33 (d, J=8.8 Hz, 1H), 5.12 (s, 1H), 2.69 (s, 3H), 2.57 (s, 3H). MS (ES+) m/e 361.3 (M+H)$^+$.

Example 34 methyl 4-(2-((4-(1H-pyrazol-4-yl)phenyl)amino)-1-(methylamino)-2-oxoethyl)benzoate

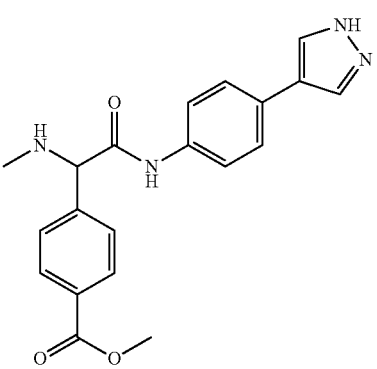 [SMILES: CNC(C(=O)Nc1ccc(-c2cn[nH]c2)cc1)c1ccc(C(=O)OC)cc1]

The reaction was conducted following general procedure A. The final residue was purified by reverse phase preparative HPLC to afford methyl 4-(2-((4-(1H-pyrazol-4-yl)phenyl)amino)-1-(methylamino)-2-oxoethyl)benzoate as an off-white solid (11%). $^1$H NMR (400 MHz, CD$_3$OD) δ 8.17 (dd, J=6.8, 2.0 Hz, 2H), 7.92 (s, 2H), 7.74 (d, J=8.4 Hz, 2H), 7.58-7.53 (m, 4H), 5.07 (s, 1H), 3.92 (s, 3H), 2.70 (s, 3H). MS (ES+) m/e 365.1 (M+H)$^+$.

Example 35

N-(4-(1H-pyrazol-4-yl)phenyl)-2-(2-methyl-1H-benzo[d]imidazol-6-yl)-2-(methylamino)acetamide

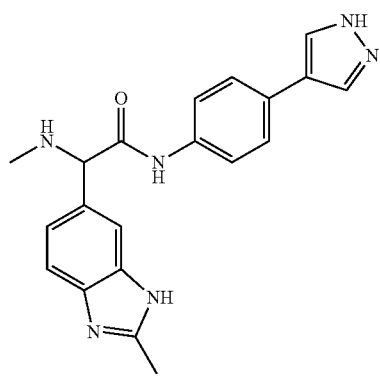 [SMILES: CNC(C(=O)Nc1ccc(-c2cn[nH]c2)cc1)c1ccc2nc(C)[nH]c2c1]

The reaction was conducted following general procedure A. The final residue was purified by reverse phase preparative HPLC to afford N-(4-(1H-pyrazol-4-yl)phenyl)-2-(2-methyl-1H-benzo[d]imidazol-6-yl)-2-(methylamino)acetamide as a yellow oil (4%). $^1$H NMR (400 MHz, CD$_3$OD) δ 8.02 (d, J=1.2 Hz, 1H), 7.92 (s, 2H), 7.86 (d, J=8.4 Hz, 1H), 7.75 (dd, J=8.0, 1.6 Hz, 1H), 7.59-7.52 (m, 4H), 5.21 (s, 1H), 2.84 (s, 3H), 2.71 (s, 3H). MS (ES+) m/e 361.2 (M+H)$^+$.

Example 36

N-(4-(1H-pyrazol-4-yl)phenyl)-2-(3-methoxyphenyl)-2-((3-methoxypropyl)amino)acetamide

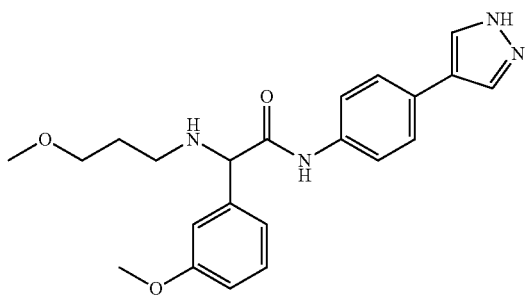 [SMILES: COCCCNC(C(=O)Nc1ccc(-c2cn[nH]c2)cc1)c1cccc(OC)c1]

The reaction was conducted following general procedure B. The final residue was purified by reverse phase preparative HPLC to afford N-(4-(1H-pyrazol-4-yl)phenyl)-2-(3-methoxyphenyl)-2-((3-methoxypropyl)amino)acetamide as an off-white solid (21%). $^1$H NMR (400 MHz, CD$_3$OD) δ 8.55 (s, 2H), 7.72-7.65 (m, 4H), 7.44 (t, J=7.6 Hz, 1H), 7.26-7.25 (m, 2H), 7.09 (dd, J=8.0, 2.0 Hz, 1H), 5.15 (s, 1H), 3.85 (s, 3H), 3.51 (t, J=5.6 Hz, 2H), 3.35 (s, 3H), 3.30-3.08 (m, 2H), 2.03-1.98 (m, 2H). MS (ES+) m/e 395.3 (M+H)$^+$.

Example 37

N-(4-(1H-pyrazol-4-yl)phenyl)-2-((2-ethoxyethyl)amino)-2-(3-methoxyphenyl)acetamide

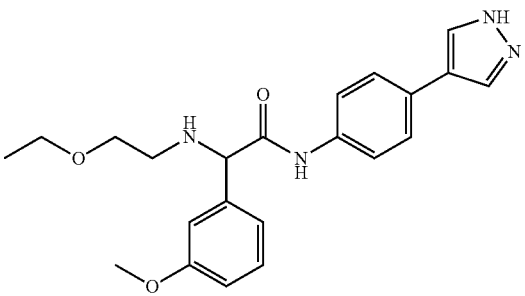 [SMILES: CCOCCNC(C(=O)Nc1ccc(-c2cn[nH]c2)cc1)c1cccc(OC)c1]

The reaction was conducted following general procedure B. The final residue was purified by reverse phase preparative HPLC to afford N-(4-(1H-pyrazol-4-yl)phenyl)-2-((2-ethoxyethyl)amino)-2-(3-methoxyphenyl)acetamide as a white solid (8%). $^1$H NMR (400 MHz, DMSO-d$_6$) δ 12.89 (s, 1H), 10.09 (s, 1H), 8.12 (s, 1H), 7.87 (s, 1H), 7.60 (d, J=8.4 Hz, 2H), 7.54 (d, J=8.8 Hz, 2H), 7.27 (t, J=8.0 Hz, 1H), 7.04-7.02 (m, 2H), 6.85 (dd, J=8.0, 2.0 Hz, 1H), 4.33 (s, 1H), 3.75 (s, 3H), 3.48-3.41 (m, 4H), 2.66-2.63 (m, 2H), 1.11 (t, J=7.2 Hz, 3H). MS (ES+) m/e 395.3 (M+H)$^+$.

Example 38

N-(4-(1H-pyrazol-4-yl)phenyl)-2-((3-(dimethylamino)propyl)amino)-2-(3-methoxyphenyl)acetamide

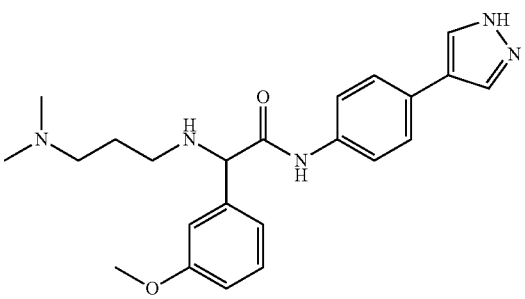 [SMILES: COc1cccc(C(NCCCN(C)C)C(=O)Nc2ccc(-c3cn[nH]c3)cc2)c1]

The reaction was conducted following general procedure B. The final residue was purified by reverse phase preparative HPLC to afford N-(4-(1H-pyrazol-4-yl)phenyl)-2-((3-(dimethylamino)propyl)amino)-2-(3-methoxyphenyl)acetamide as an off-white solid (4%). $^1$H NMR (400 MHz, CD$_3$OD) δ 7.93 (s, 2H), 7.60-7.53 (m, 4H), 7.30 (t, J=8.0 Hz, 1H), 7.09-7.08 (m, 2H), 6.90 (dd, J=8.4, 1.6 Hz, 1H), 4.34 (s, 1H), 3.82 (s, 3H), 2.68-2.61 (m, 2H), 2.48-2.42 (m, 2H), 2.30 (s, 6H), 1.83-1.74 (m, 2H). MS (ES+) m/e 408.3 (M+H)$^+$.

Example 39

N-(4-(1H-pyrazol-4-yl)phenyl)-2-((2-(dimethylamino)-2-oxoethyl)amino)-2-(3-methoxyphenyl)acetamide

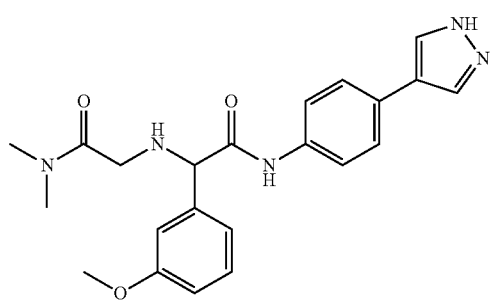 [SMILES: COc1cccc(C(NCC(=O)N(C)C)C(=O)Nc2ccc(-c3cn[nH]c3)cc2)c1]

The reaction was conducted following general procedure B. The final residue was purified by reverse phase preparative HPLC to afford N-(4-(1H-pyrazol-4-yl)phenyl)-2-((2-(dimethylamino)-2-oxoethyl)amino)-2-(3-methoxyphenyl)acetamide as a white solid (7%). $^1$H NMR (400 MHz, DMSO-$d_6$) δ 12.87 (brs, 1H), 10.18 (s, 1H), 8.16 (s, 1H), 7.99 (s, 2H), 7.62 (d, J=8.8 Hz, 2H), 7.53 (d, J=8.4 Hz, 2H), 7.28 (t, J=8.0 Hz, 1H), 7.06-7.03 (m, 2H), 6.87 (dd, J=8.0, 2.4 Hz, 1H), 4.38 (s, 1H), 3.75 (s, 3H), 3.38 (m, 2H), 2.87 (s, 3H), 2.84 (s, 3H). MS (ES+) m/e 408.3 (M+H)$^+$.

Example 40

N-(4-(1H-pyrazol-4-yl)phenyl)-2-((2-isopropoxyethyl)amino)-2-(3-methoxyphenyl)acetamide

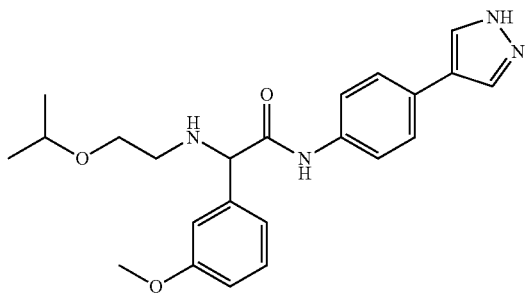 [SMILES: COc1cccc(C(NCCOC(C)C)C(=O)Nc2ccc(-c3cn[nH]c3)cc2)c1]

The reaction was conducted following general procedure B. The final residue was purified by reverse phase preparative HPLC to afford N-(4-(1H-pyrazol-4-yl)phenyl)-2-((2-isopropoxyethyl)amino)-2-(3-methoxyphenyl)acetamide as a white solid (28%). $^1$H NMR (400 MHz, CD$_3$OD) δ 8.03 (s, 2H), 7.61-7.55 (m, 4H), 7.44 (t, J=8.0 Hz, 1H), 7.23-7.20 (m, 2H), 7.10-7.07 (m, 1H), 5.13 (s, 1H), 3.85 (s, 3H), 3.74-3.70 (m, 3H), 3.21-3.13 (m, 2H), 1.22 (dd, J=6.4, 3.2 Hz, 6H). MS (ES+) m/e 409.3 (M+H)$^+$.

Example 41

N-(4-(1H-pyrazol-4-yl)phenyl)-2-((2-amino-2-oxoethyl)amino)-2-(3-methoxyphenyl)acetamide

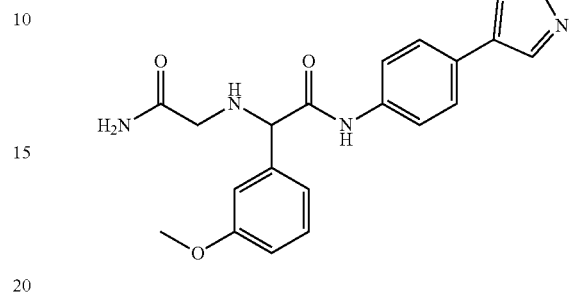

The reaction was conducted following general procedure B. The final residue was purified by reverse phase preparative HPLC to afford N-(4-(1H-pyrazol-4-yl)phenyl)-2-((2-amino-2-oxoethyl)amino)-2-(3-methoxyphenyl)acetamide as a white solid (6%). $^1$H NMR (400 MHz, DMSO-$d_6$) δ 10.13 (s, 1H), 8.22 (s, 1H), 7.99 (s, 2H), 7.62-7.53 (m, 4H), 7.45 (s, 1H), 7.28 (t, J=8.0 Hz, 1H), 7.12-7.01 (m, 3H), 6.87 (dd, J=8.0, 2.0 Hz, 1H), 4.34 (s, 1H), 3.76 (s, 3H), 3.04 (s, 2H). MS (ES+) m/e 380.2 (M+H)$^+$.

Example 42

N-(4-(1H-pyrazol-4-yl)phenyl)-2-(3-methoxyphenyl)-2-((3-(methylamino)-propyl)amino)acetamide

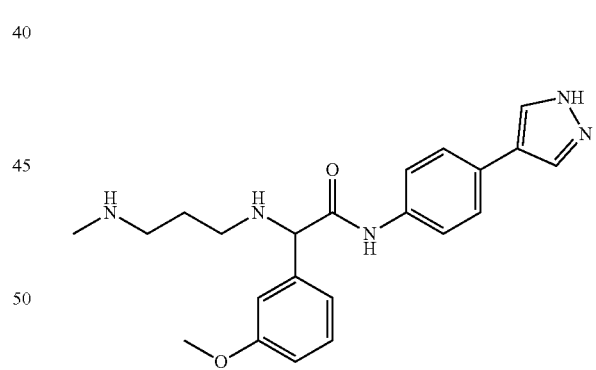

The reaction was conducted following general procedure B. The final residue was purified by reverse phase preparative HPLC to afford N-(4-(1H-pyrazol-4-yl)phenyl)-2-((2-amino-2-oxoethyl)amino)-2-(3-methoxyphenyl)acetamide as a white solid (6%). $^1$H NMR (400 MHz, DMSO-$d_6$) δ 10.81 (s, 1H), 9.70 (s, 2H), 8.65 (s, 2H), 8.00 (s, 2H), 7.56 (s, 4H), 7.43 (t, J=8.0 Hz, 1H), 7.22-7.19 (m, 2H), 7.06 (dd, J=8.0, 1.6 Hz, 1H), 5.11 (s, 1H), 3.79 (s, 3H), 2.96-2.90 (m, 4H), 2.54 (s, 3H), 2.03-1.96 (m, 2H). MS (ES+) m/e 394.3 (M+H)$^+$.

Example 43

N-(4-(1H-pyrazol-4-yl)phenyl)-2-((1-methoxy-2-methylpropan-2-yl)amino)-2-(3-methoxyphenyl)acetamide

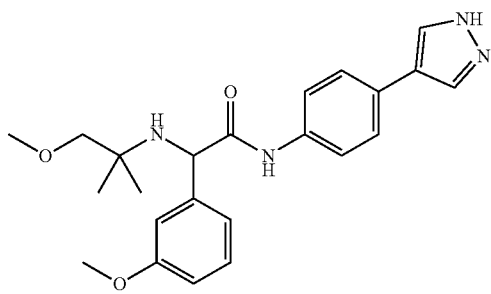 [SMILES: COCC(C)(C)NC(C(=O)Nc1ccc(-c2cn[nH]c2)cc1)c1cccc(OC)c1]

The reaction was conducted following general procedure B. The final residue was purified by reverse phase preparative HPLC to afford N-(4-(1H-pyrazol-4-yl)phenyl)-2-((1-methoxy-2-methylpropan-2-yl)amino)-2-(3-methoxyphenyl)acetamide as a white solid (17%). $^1$H NMR (400 MHz, DMSO-d$_6$) δ 10.60 (s, 1H), 9.23-9.19 (m, 2H), 7.99 (s, 2H), 7.58-7.52 (m, 4H), 7.41 (t, J=8.0 Hz, 1H), 7.21-7.19 (m, 2H), 7.04 (dd, J=8.8, 2.8 Hz, 1H), 5.22 (s, 1H), 3.79 (s, 3H), 3.42-3.35 (m, 2H), 3.17 (s, 3H), 1.33 (s, 3H), 1.31 (s, 3H). MS (ES+) m/e 409.3 (M+H)$^+$.

Example 44

N-(4-(1H-pyrazol-4-yl)phenyl)-2-(3-methoxyphenyl)-2-((2-(methylamino)-2-oxoethyl)amino)acetamide

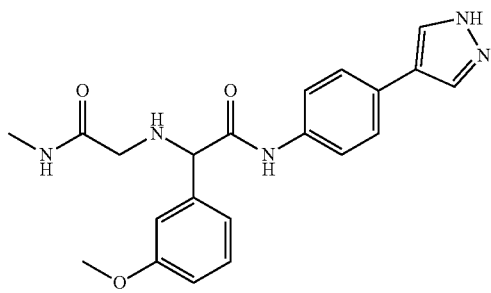 [SMILES: CNC(=O)CNC(C(=O)Nc1ccc(-c2cn[nH]c2)cc1)c1cccc(OC)c1]

The reaction was conducted following general procedure B. The final residue was purified by reverse phase preparative HPLC to afford N-(4-(1H-pyrazol-4-yl)phenyl)-2-(3-methoxyphenyl)-2-((2-(methylamino)-2-oxoethyl)amino)acetamide as a yellow solid (3%). $^1$H NMR (400 MHz, CD$_3$OD) δ 7.95 (s, 2H), 7.59-7.53 (m, 4H), 7.44 (t, J=8.4 Hz, 1H), 7.18-7.17 (m, 2H), 7.16-7.10 (m, 1H), 5.12 (s, 1H), 3.84 (s, 3H), 3.68 (s, 2H), 2.79 (s, 3H). MS (ES+) m/e 394.3 (M+H)$^+$.

Example 45

2-(((1H-pyrazol-4-yl)methyl)amino)-N-(4-(1H-pyrazol-4-yl)phenyl)-2-(3-methoxyphenyl)acetamide

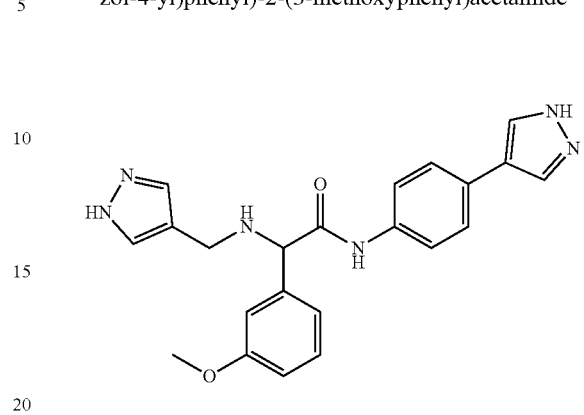

The reaction was conducted following general procedure B. The final residue was purified by reverse phase preparative HPLC to afford 2-(((1H-pyrazol-4-yl)methyl)amino)-N-(4-(1H-pyrazol-4-yl)phenyl)-2-(3-methoxyphenyl)acetamide as a white solid (1%). $^1$H NMR (400 MHz, DMSO-d$_6$) δ 10.58 (s, 1H), 9.77 (s, 2H), 7.99 (s, 2H), 7.70 (s, 2H), 7.57 (d, J=8.8 Hz, 2H), 7.51 (d, J=8.8 Hz, 2H), 7.43 (t, J=8.0 Hz, 1H), 7.20-7.17 (m, 2H), 7.06 (dd, J=8.0, 2.0 Hz, 1H), 4.91 (s, 1H), 4.01 (s, 2H), 3.79 (s, 3H). MS (ES+) m/e 403.3 (M+H)$^+$.

Example 46

N-(4-(1H-pyrazol-4-yl)phenyl)-2-(ethyl(2-methoxyethyl)amino)-2-(3-methoxyphenyl)acetamide

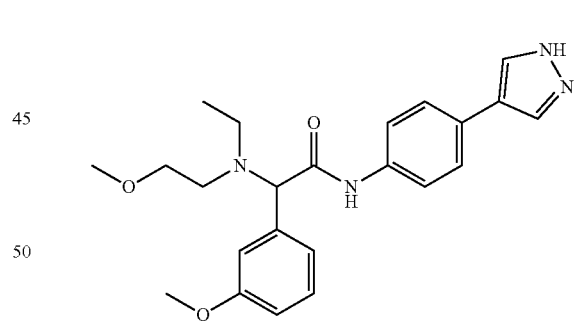

The reaction was conducted following general procedure B. The final residue was purified by reverse phase preparative HPLC to afford N-(4-(1H-pyrazol-4-yl)phenyl)-2-(ethyl(2-methoxyethyl)amino)-2-(3-methoxyphenyl)acetamide as a white solid (19%). $^1$H NMR (400 MHz, Acetone-d$_6$) δ 11.21 (s, 1H), 8.01 (s, 2H), 7.73 (d, J=8.8 Hz, 2H), 7.60 (d, J=8.8 Hz, 2H), 7.47-7.43 (m, 2H), 7.37 (d, J=8.0 Hz, 1H), 7.11-7.09 (m, 1H), 6.03-6.01 (m, 1H), 3.93-3.80 (m, 5H), 3.74-3.53 (m, 3H), 3.42 (m, 4H), 1.44 (t, J=7.2 Hz, 3H). MS (ES+) m/e 409.3 (M+H)$^+$.

Example 47

N-(4-(1H-pyrazol-4-yl)phenyl)-2-((2-methoxyethyl)(methyl)amino)-2-(3-methoxyphenyl)acetamide

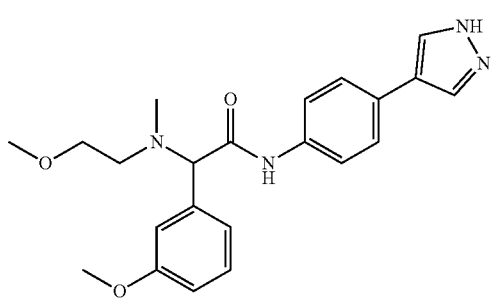 [SMILES: COCCN(C)C(C(=O)Nc1ccc(-c2cn[nH]c2)cc1)c1cccc(OC)c1]

The reaction was conducted following general procedure B. The final residue was purified by reverse phase preparative HPLC to afford N-(4-(1H-pyrazol-4-yl)phenyl)-2-((2-methoxyethyl)(methyl)amino)-2-(3-methoxyphenyl)acetamide as an off-white solid (24%). $^1$H NMR (400 MHz, Acetone-$d_6$) δ 10.85 (s, 1H), 8.01 (s, 2H), 7.71 (d, J=8.8 Hz, 2H), 7.61 (d, J=8.4 Hz, 2H), 7.46 (t, J=8.0 Hz, 1H), 7.41 (s, 1H), 7.33 (d, J=7.6 Hz, 1H), 7.11 (dd, J=8.0, 2 Hz, 1H), 5.80 (d, J=4.4 Hz, 1H), 3.95-3.92 (m, 2H), 3.87 (s, 3H), 3.72-3.60 (m, 2H), 3.42 (s, 3H), 3.06 (s, 3H). MS (ES+) m/e 395.3 (M+H)$^+$.

Example 48

N-(2-(2-(dimethylamino)ethoxy)-5-fluoro-4-(1H-pyrazol-4-yl)phenyl)-2-((2-methoxyethyl)amino)-2-(3-methoxyphenyl)acetamide

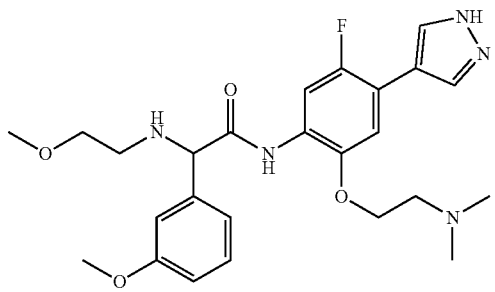

The reaction was conducted following general procedure B. The final residue was purified by reverse phase preparative HPLC to afford N-(2-(2-(dimethylamino)ethoxy)-5-fluoro-4-(1H-pyrazol-4-yl)phenyl)-2-(2-methoxyethyl)amino)-2-(3-methoxyphenyl)acetamide as an off-white solid (13%). $^1$H NMR (400 MHz, DMSO-$d_6$) δ 9.94 (s, 1H), 9.92 (s, 1H), 9.66 (s, 2H), 8.07 (s, 2H), 7.87 (d, J=12.4 Hz, 1H), 7.46-7.39 (m, 2H), 7.23-7.19 (m, 2H), 7.07 (dd, J=8.0, 6.0 Hz, 1H), 5.36 (s, 1H), 4.44-4.35 (m, 2H), 3.80 (s, 3H), 3.66-3.64 (m, 2H), 3.63-3.49 (m, 2H), 3.31 (s, 3H), 3.07-3.00 (m, 2H), 2.76 (s, 6H). MS (ES+) m/e 486.3 (M+H)$^+$.

Example 49

N-(4-(1H-pyrazol-4-yl)phenyl)-2-((2-methoxyethyl)amino)-2-(3-methoxyphenyl)-N-methylacetamide

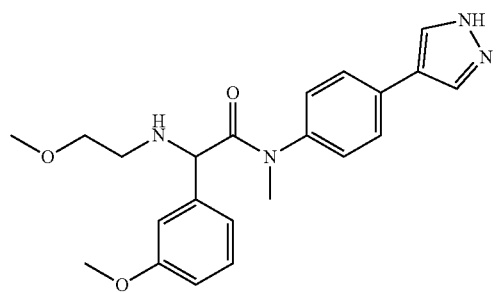 [SMILES: COCCNC(C(=O)N(C)c1ccc(-c2cn[nH]c2)cc1)c1cccc(OC)c1]

The reaction was conducted following general procedure B. The final residue was purified by reverse phase preparative HPLC to afford N-(4-(1H-pyrazol-4-yl)phenyl)-2-((2-methoxyethyl)amino)-2-(3-methoxyphenyl)-N-methylacetamide as a yellow solid (15%). $^1$H NMR (400 MHz, D$_2$O) δ 8.07 (s, 2H), 7.48 (m, 2H), 7.27-7.23 (m, 2H), 6.95 (m, 2H), 6.68 (d, J=6.8 Hz, 1H), 6.28 (s, 1H), 5.02 (s, 1H), 3.61 (m, 2H), 3.52 (s, 3H), 3.30 (s, 3H), 3.24 (s, 3H), 3.15-3.11 (m, 1H), 3.02-2.97 (m, 1H). MS (ES+) m/e 395.3 (M+H)$^+$.

Example 50

N-(4-(1H-pyrazol-4-yl)phenyl)-2-(3-methoxyphenyl)-2-((2-morpholinoethyl)amino)acetamide

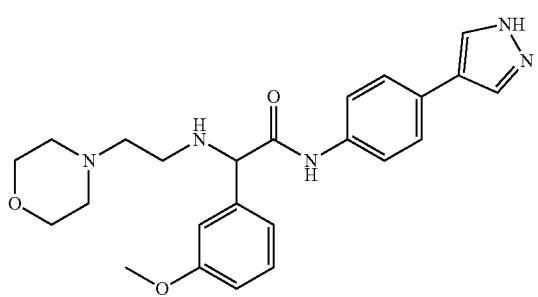 [SMILES: COc1cccc(C(NCCN2CCOCC2)C(=O)Nc2ccc(-c3cn[nH]c3)cc2)c1]

The reaction was conducted following general procedure B. The final residue was purified by reverse phase preparative HPLC to afford N-(4-(1H-pyrazol-4-yl)phenyl)-2-(3-methoxyphenyl)-2-((2-morpholinoethyl)amino)acetamide as a white solid (38%). $^1$H NMR (400 MHz, DMSO-$d_6$) δ 10.72 (s, 1H), 8.00 (s, 2H), 7.59-7.57 (m, 4H), 7.42 (t, J=7.6 Hz, 1H), 7.21-7.17 (m, 2H), 7.07-7.04 (m, 1H), 5.09 (s, 1H), 3.79 (m, 7H), 3.31-3.12 (m, 8H). MS (ES+) m/e 436.3 (M+H)$^+$.

Example 51

N-(2-(2-(dimethylamino)ethoxy)-5-fluoro-4-(1H-pyrazol-4-yl)phenyl)-2-((2-methoxyethyl)(methyl)amino)-2-(3-methoxyphenyl)acetamide

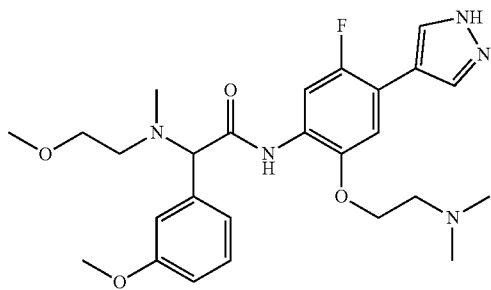

The reaction was conducted following general procedure B. The final residue was purified by reverse phase preparative HPLC to afford N-(2-(2-(dimethylamino)ethoxy)-5-fluoro-4-(1H-pyrazol-4-yl)phenyl)-2-((2-methoxyethyl)(methyl)amino)-2-(3-methoxyphenyl)acetamide as a yellow solid (31%). $^1$H NMR (400 MHz, D$_2$O) δ 8.04 (s, 2H), 7.56-7.48 (m, 2H), 7.19-7.14 (m, 4H), 5.27 (s, 1H), 4.23-4.21 (m, 1H), 4.11-4.10 (m, 1H), 3.80 (m, 5H), 3.50 (m, 2H), 3.33 (m, 4H), 3.19-3.16 (m, 1H), 2.82-2.62 (m, 9H). MS (ES+) m/e 500.3 (M+H)$^+$.

Example 52

N-(4-(1H-pyrazol-4-yl)phenyl)-2-(3-methoxyphenyl)-2-((2-(pyrrolidin-1-yl)ethyl)amino)acetamide

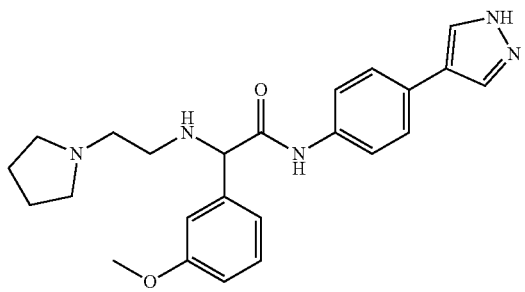 [SMILES: COc1cccc(C(NCCN2CCCC2)C(=O)Nc2ccc(-c3cn[nH]c3)cc2)c1]

The reaction was conducted following general procedure B. The final residue was purified by reverse phase preparative HPLC to afford N-(4-(1H-pyrazol-4-yl)phenyl)-2-(3-methoxyphenyl)-2-((2-(pyrrolidin-1-yl)ethyl)amino)acetamide as a white solid (35%). $^1$H NMR (400 MHz, DMOS-d$_6$) δ 10.64 (s, 1H), 8.00 (s, 2H), 7.57 (m, 4H), 7.41 (t, J=8.0, 1H), 7.19-7.16 (m, 2H), 7.05-7.03 (m, 1H), 5.01 (s, 1H), 3.79 (s, 3H), 3.44-3.27 (m, 8H), 1.94 (m, 4H). MS (ES+) m/e 420.3 (M+H)$^+$.

Example 53

N-(4-(1H-pyrazol-4-yl)phenyl)-2-((1-(methoxymethyl)cyclopropyl)amino)-2-(3-methoxyphenyl)acetamide

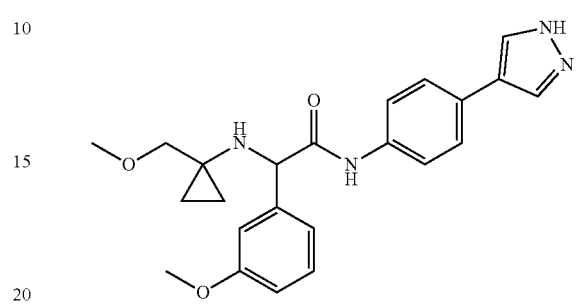

The reaction was conducted following general procedure B. The final residue was purified by reverse phase preparative HPLC to afford N-(4-(1H-pyrazol-4-yl)phenyl)-2-((1-(methoxymethyl)cyclopropyl)amino)-2-(3-methoxyphenyl)acetamide as an off-white solid (27%). $^1$H NMR (400 MHz, DMOS-d$_6$) δ 10.65 (brs, 1H), 9.58 (brs, 1H), 8.00 (s, 2H), 7.62-7.52 (m, 4H), 7.42 (t, J=7.6 Hz, 1H), 7.24-7.15 (m, 2H), 7.08-7.02 (m, 1H), 5.25 (s, 1H), 3.80 (s, 3H), 3.64 (d, J=11.6 Hz, 1H), 3.37 (d, J=11.6 Hz, 1H), 3.23 (s, 3H), 1.23-2.21 (m, 1H), 1.02-0.91 (m, 1H), 0.89-0.76 (m, 2H). MS (ES+) m/e 407.3 (M+H)$^+$.

Example 54

N-(4-(1H-pyrazol-4-yl)phenyl)-2-(3-methoxyphenyl)-2-((2-(2,2,2-trifluoroethoxy)ethyl)amino)acetamide

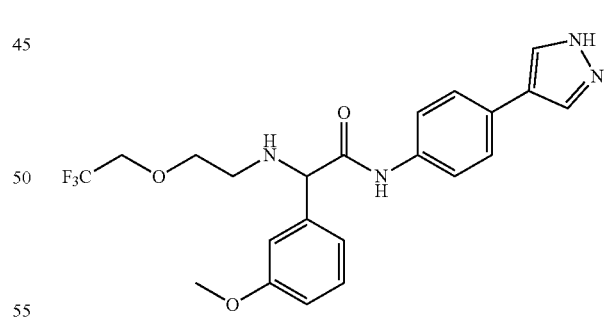

The reaction was conducted following general procedure B. The final residue was purified by reverse phase preparative HPLC to afford N-(4-(1H-pyrazol-4-yl)phenyl)-2-(3-methoxyphenyl)-2-((2-(2,2,2-trifluoroethoxy)ethyl)amino)acetamide as an off-white solid (6%). $^1$H NMR (400 MHz, DMOS-d$_6$) δ 12.86 (s, 1H), 10.06 (s, 1H), 8.11 (s, 1H), 7.86 (s, 1H), 7.60-7.52 (m, 4H), 7.26 (t, J=7.9 Hz, 1H), 7.05-7.02 (m, 2H), 6.85 (dd, J=8.2, 1.8 Hz, 1H), 4.34 (d, J=7.6 Hz, 1H), 4.10-4.03 (m, 2H), 3.75 (s, 3H), 3.69 (t, J=5.6 Hz, 2H), 2.68 (s, 3H). MS (ES+) m/e 449.2 (M+H)$^+$.

Example 55

N-(3-fluoro-4-(1H-pyrazol-4-yl)phenyl)-2-((2-methoxyethyl)amino)-2-(3-methoxyphenyl)acetamide

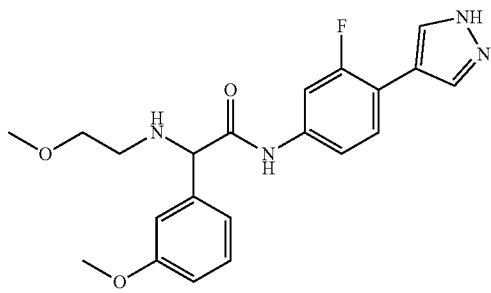 [SMILES: COCCNC(C(=O)Nc1ccc(-c2cn[nH]c2)c(F)c1)c1cccc(OC)c1]

The reaction was conducted following general procedure B. The final residue was purified by reverse phase preparative HPLC to afford N-(3-fluoro-4-(1H-pyrazol-4-yl)phenyl)-2-((2-methoxyethyl)amino)-2-(3-methoxyphenyl)acetamide as a yellow solid (21%). $^1$H NMR (400 MHz, DMOS-d$_6$) δ 10.97 (s, 1H), 9.64 (s, 2H), 8.00 (d, J=1.6 Hz, 2H), 7.70 (t, J=8.0 Hz, 1H), 7.62 (dd, J=13.2, 2.0 Hz, 1H), 7.41 (t, J=8.0 Hz, 1H), 7.32 (dd, J=8.4, 2.0 Hz, 1H), 7.24-7.19 (m, 2H), 7.06-7.03 (m, 1H), 5.14 (s, 1H), 3.79 (s, 3H), 3.64-3.57 (m, 2H), 3.29 (s, 3H), 3.09-3.00 (m, 2H). MS (ES+) m/e 399.2 (M+H)$^+$.

Example 56

N-(3-methoxy-4-(1H-pyrazol-4-yl)phenyl)-2-((2-methoxyethyl)amino)-2-(3-methoxyphenyl)acetamide

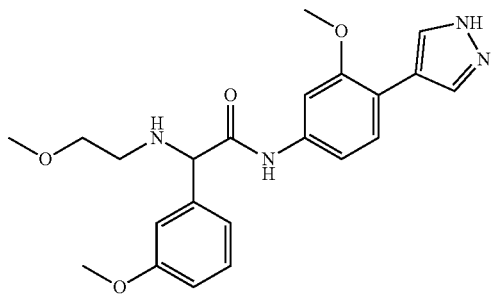 [SMILES: COCCNC(C(=O)Nc1ccc(-c2cn[nH]c2)c(OC)c1)c1cccc(OC)c1]

The reaction was conducted following general procedure B. The final residue was purified by reverse phase preparative HPLC to afford N-(3-methoxy-4-(1H-pyrazol-4-yl)phenyl)-2-((2-methoxyethyl)amino)-2-(3-methoxyphenyl)acetamide as a yellow solid (17%). $^1$H NMR (400 MHz, DMOS-d$_6$) δ 10.79 (s, 1H), 9.62 (s, 2H), 8.00 (s, 2H), 7.58 (d, J=8.4 Hz, 1H), 7.41 (t, J=8.0 Hz, 1H), 7.32 (d, J=1.6 Hz, 1H), 7.26-7.21 (m, 3H), 7.06-7.02 (m, 1H), 5.13 (s, 1H), 3.84 (s, 3H), 3.79 (s, 3H), 3.64-3.59 (m, 2H), 3.30 (s, 3H), 3.09-3.00 (m, 2H). MS (ES+) m/e 411.3 (M+H)$^+$.

Example 57

N-(4-(1H-pyrazol-4-yl)phenyl)-2-((2-(dimethylamino)ethyl)amino)-2-(3-methoxyphenyl)acetamide

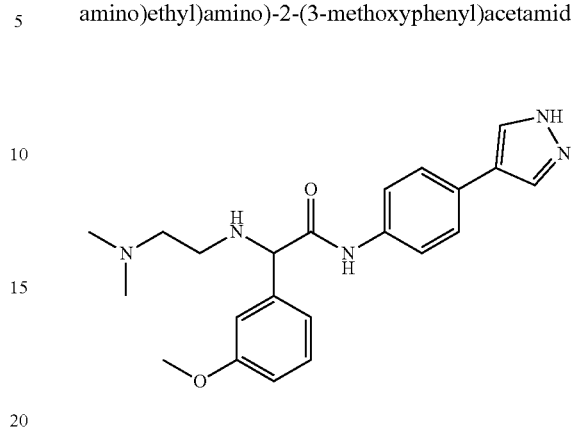

The reaction was conducted following general procedure B. The final residue was purified by reverse phase preparative HPLC to afford N-(4-(1H-pyrazol-4-yl)phenyl)-2-((2-(dimethylamino)ethyl)amino)-2-(3-methoxyphenyl)acetamide as a white solid (41%). $^1$H NMR (400 MHz, DMOS-d$_6$) δ 10.18 (s, 1H), 8.25 (s, 1H), 7.99 (s, 2H), 7.60 (d, J=8.4 Hz, 2H), 7.53 (d, J=8.8 Hz, 2H), 7.27 (t, J=8.0 Hz, 1H), 7.05-7.02 (m, 2H), 6.86 (dd, J=8.4, 2.4 Hz, 1H), 4.34 (s, 1H), 3.75 (s, 3H), 2.65-2.51 (m, 4H), 2.30 (s, 6H). MS (ES+) m/e 394.3 (M+H)$^+$.

Example 58

(R)—N-(4-(1H-pyrazol-4-yl)phenyl)-2-((2-methoxyethyl)amino)-2-(3-methoxyphenyl)acetamide

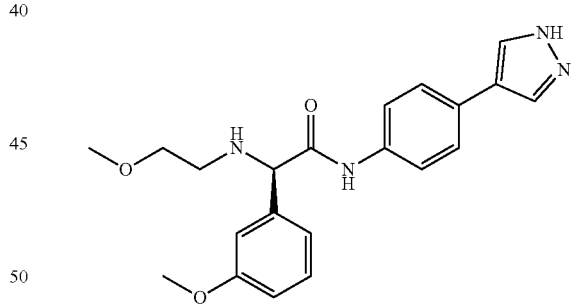

The reaction was conducted following general procedure B. The final residue was purified by reverse phase preparative HPLC to afford (R)—N-(4-(1H-pyrazol-4-yl)phenyl)-2-((2-methoxyethyl)amino)-2-(3-methoxyphenyl)acetamide as a white solid (12%). Enantiomers were separated by SFC (DAICEL CHIRALPAK AS column). Mobile phase: 40% EtOH with 0.1% NH$_4$OH in CO$_2$, flow rate 70 g/min to afford the desired compound with 99% enantiomeric purity. $^1$H NMR (400 MHz, DMSO-d$_6$) δ 10.18 (s, 1H), 8.16 (s, 1H), 7.99 (s, 2H), 7.61-7.53 (m, 4H), 7.27 (t, J=4.6 Hz, 1H), 7.06-7.03 (m, 2H), 6.87-6.84 (m, 1H), 4.40 (s, 1H), 3.75 (s, 3H), 3.44 (t, J=5.2 Hz, 2H), 3.24 (s, 3H), 2.67 (t, J=5.2 Hz, 2H). MS (ES+) m/e 381.3 (M+H)$^+$. [α]$^{25\,°C}_D$=+114 (c=0.2 in MeOH).

Example 59

(S)—N-(4-(1H-pyrazol-4-yl)phenyl)-2-((2-methoxyethyl)amino)-2-(3-methoxyphenyl)acetamide

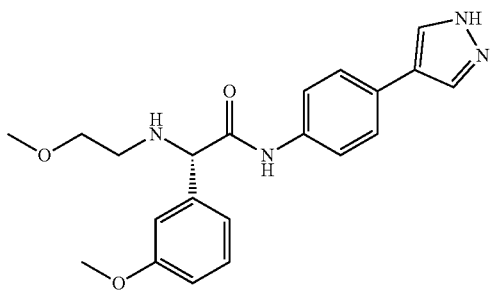

The reaction was conducted following general procedure B. The final residue was purified by reverse phase preparative HPLC to afford (S)—N-(4-(1H-pyrazol-4-yl)phenyl)-2-((2-methoxyethyl)amino)-2-(3-methoxyphenyl)acetamide as a white solid (12%). Enantiomers were separated by SFC (DAICEL CHIRALPAK AS column). Mobile phase: 40% EtOH with 0.1% NH$_4$OH in CO$_2$, flow rate 70 g/min to afford the desired compound with 99% enantiomeric purity. $^1$H NMR (400 MHz, DMSO-d$_6$) δ 10.18 (s, 1H), 8.16 (s, 1H), 7.99 (s, 2H), 7.61-7.53 (m, 4H), 7.27 (t, J=4.6 Hz, 1H), 7.06-7.03 (m, 2H), 6.87-6.84 (m, 1H), 4.40 (s, 1H), 3.75 (s, 3H), 3.44 (t, J=5.2 Hz, 2H), 3.24 (s, 3H), 2.67 (t, J=5.2 Hz, 2H). MS (ES+) m/e 381.3 (M+H)$^+$. (S)—N-(4-(1H-pyrazol-4-yl)phenyl)-2-((2-methoxyethyl)amino)-2-(3-methoxyphenyl)acetamide. [α]$^{25°\ C.}_D$=−103.5 (c=0.2 in MeOH).

Example 60

(S)—N-(4-(1H-pyrazol-4-yl)phenyl)-2-((2-(dimethylamino)ethyl)amino)-2-(3-methoxyphenyl)acetamide

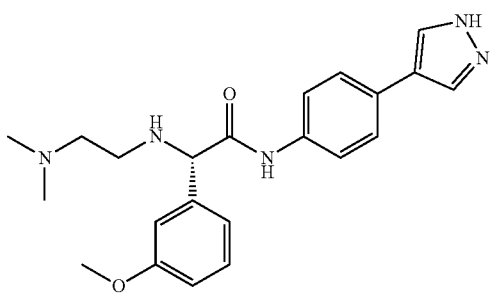

The reaction was conducted following general procedure B. The final residue was purified by reverse phase preparative HPLC to afford (S)—N-(4-(1H-pyrazol-4-yl)phenyl)-2-((2-(dimethylamino)ethyl)amino)-2-(3-methoxyphenyl)acetamide as a white solid (41%). Enantiomers were separated by SFC (DAICEL CHIRALPAK AS column). Mobile phase: 50% EtOH with 0.1% NH$_4$OH in CO$_2$, flow rate 70 g/min to afford the desired compound with 99% enantiomeric purity. $^1$H NMR (400 MHz, DMOS-d$_6$) δ 10.18 (s, 1H), 8.25 (s, 1H), 7.99 (s, 2H), 7.60 (d, J=8.4 Hz, 2H), 7.53 (d, J=8.8 Hz, 2H), 7.27 (t, J=8.0 Hz, 1H), 7.05-7.02 (m, 2H), 6.86 (dd, J=8.4, 2.4 Hz, 1H), 4.34 (s, 1H), 3.75 (s, 3H), 2.65-2.51 (m, 4H), 2.30 (s, 6H). MS (ES+) m/e 394.3 (M+H)$^+$. [α]$^{25°\ C.}_D$=+95.7 (c=0.2 in MeOH).

Example 61

(R)—N-(4-(1H-pyrazol-4-yl)phenyl)-2-((2-(dimethylamino)ethyl)amino)-2-(3-methoxyphenyl)acetamide

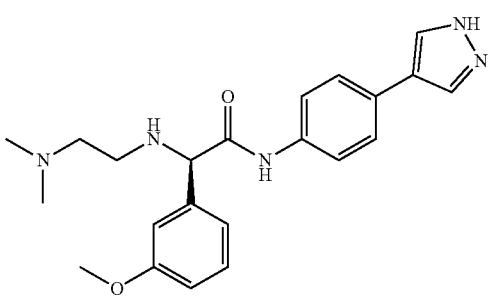 [SMILES: COc1cccc([C@@H](NCCN(C)C)C(=O)Nc2ccc(-c3cn[nH]c3)cc2)c1]

The reaction was conducted following general procedure B. The final residue was purified by reverse phase preparative HPLC to afford (R)—N-(4-(1H-pyrazol-4-yl)phenyl)-2-((2-(dimethylamino)ethyl)amino)-2-(3-methoxyphenyl)acetamide as a white solid (41%). Enantiomers were separated by SFC (DAICEL CHIRALPAK AS column). Mobile phase: 50% EtOH with 0.1% NH$_4$OH in CO$_2$, flow rate 70 g/min to afford the desired compound with 99% enantiomeric purity. $^1$H NMR (400 MHz, DMOS-d$_6$) δ 10.18 (s, 1H), 8.25 (s, 1H), 7.99 (s, 2H), 7.60 (d, J=8.4 Hz, 2H), 7.53 (d, J=8.8 Hz, 2H), 7.27 (t, J=8.0 Hz, 1H), 7.05-7.02 (m, 2H), 6.86 (dd, J=8.4, 2.4 Hz, 1H), 4.34 (s, 1H), 3.75 (s, 3H), 2.65-2.51 (m, 4H), 2.30 (s, 6H). MS (ES+) m/e 394.3 (M+H)$^+$. [α]$^{25°\ C.}_D$=−92.8 (c=0.2 in MeOH).

Example 62

(R)—N-(4-(1H-pyrazol-4-yl)phenyl)-2-(3-methoxyphenyl)-2-((2-(methylamino)ethyl)amino)acetamide

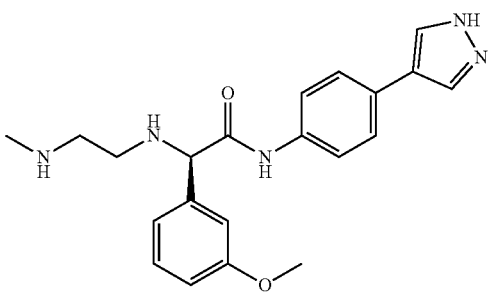 [SMILES: CNCCN[C@@H](C(=O)Nc1ccc(-c2cn[nH]c2)cc1)c1cccc(OC)c1]

Step 1: Compound tert-butyl (2-((tert-butoxycarbonyl)(methyl)amino)ethyl)-(1-(3-methoxyphenyl)-2-oxo-2-((4-(1-(tetrahydro-2H-pyran-2-yl)-1H-pyrazol-4-yl)phenyl)amino)ethyl)carbamate was dissolved in EtOH (0.15 M) and para-toluene sulfonic acid (2 equiv) added. Solution stirred for 20 hours at 15° C. The reaction mixture was quenched with NaHCO$_3$ and extracted with EtOAc. Combined organic fractions were washed with brine, dried with Na$_2$SO$_4$, filtered and concentrated under reduced pressure to afford tert-butyl (2-((4-(1H-pyrazol-4-yl)phenyl)amino)-1-(3-methoxyphenyl)-2-oxoethyl)(2-((tert-butoxycarbonyl)(methyl)amino)ethyl)carbamate as yellow solid in 92% yield. Enantiomers were separated by SFC (DAICEL CHIRALPAK OD column). Mobile phase: 45% EtOH with 0.1% NH$_4$OH in CO$_2$, flow rate 70 g/min to afford tert-butyl (R)-(2-((2-((4-(1H-pyrazol-4-yl)phenyl)amino)-1-(3-methoxyphenyl)-2-oxoethyl)(tert-butoxycarbonyl)amino)ethyl)-(methyl)carbamate with 99% enantiomeric purity. $^1$H NMR (400 MHz, DMOS-d$_6$) δ δ 12.84 (s, 1H), 10.19 (s, 1H), 8.04 (s, 2H), 7.71-7.49 (m, 4H), 7.37-7.33 (m, 1H), 7.03-6.89 (m, 3H), 6.02-5.33 (m, 1H), 3.76 (s, 3H), 3.42-2.70 (m, 7H), 1.55-1.25 (m, 18H).

Step 2: Compound tert-butyl (R)-(2-((4-(1H-pyrazol-4-yl)phenyl)amino)-1-(3-methoxyphenyl)-2-oxoethyl)(2-((tert-butoxycarbonyl)(methyl)amino)ethyl)carbamate was dissolved in dichloromethane and 4N HCl in dioxane was added. Reaction mixture stirred at room temperature for 4 hours and concentrated under reduced pressure. The final residue was purified by reverse phase preparative HPLC to afford (R)—N-(4-(1H-pyrazol-4-yl)phenyl)-2-(3-methoxyphenyl)-2-((2-(methylamino)ethyl)amino)acetamide as a white solid (12%). $^1$H NMR (400 MHz, CD$_3$OD) δ δ 8.51 (s, 1H), 7.91 (s, 2H), 7.58-7.51 (m, 4H), 7.31 (t, J=7.6 Hz, 1H), 7.09-7.08 (m, 2H), 6.91-6.89 (m, 1H), 4.42 (s, 1H), 3.81 (s, 3H), 3.14-3.04 (m, 2H), 2.92-2.82 (m, 2H), 2.72 (s, 3H). MS (ES+) m/e 380.4 (M+H)$^+$. [α]$^{25°\ C}_D$=−86.02 (0.5 in MeOH).

Example 63

(S)—N-(4-(1H-pyrazol-4-yl)phenyl)-2-(3-methoxyphenyl)-2-((2-(methylamino)ethyl)amino)acetamide

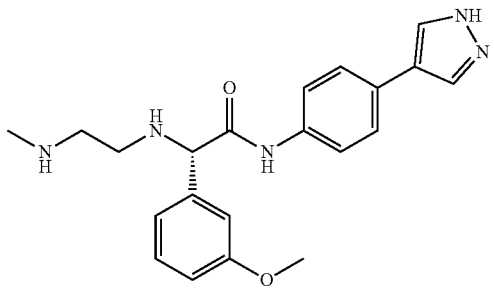 [SMILES: CNCCN[C@H](C(=O)Nc1ccc(-c2cn[nH]c2)cc1)c1cccc(OC)c1]

Step 1: Compound tert-butyl (2-((tert-butoxycarbonyl)(methyl)amino)ethyl)(1-(3-methoxyphenyl)-2-oxo-2-((4-(1-(tetrahydro-2H-pyran-2-yl)-1H-pyrazol-4-yl)phenyl)amino)ethyl)carbamate was dissolved in EtOH (0.15 M) and para-toluene sulfonic acid (2 equiv) added. Solution stirred for 20 hours at 15° C. The reaction mixture was quenched with NaHCO$_3$ and extracted with EtOAc. Combined organic fractions were washed with brine, dried with Na$_2$SO$_4$, filtered and concentrated under reduced pressure to afford tert-butyl (2-((4-(1H-pyrazol-4-yl)phenyl)amino)-1-(3-methoxyphenyl)-2-oxoethyl)(2-((tert-butoxycarbonyl)(methyl)amino)ethyl)carbamate as yellow solid in 92% yield. Enantiomers were separated by SFC (DAICEL CHIRALPAK OD column). Mobile phase: 45% EtOH with 0.1% NH$_4$OH in CO$_2$, flow rate 70 g/min to afford tert-butyl (S)-(2-((2-((4-(1H-pyrazol-4-yl)phenyl)amino)-1-(3-methoxyphenyl)-2-oxoethyl)(tert-butoxycarbonyl)amino)ethyl)(methyl)carbamate with 99% enantiomeric purity. $^1$H NMR (400 MHz, DMOS-d$_6$) δ δ 12.84 (s, 1H), 10.19 (s, 1H), 8.04 (s, 2H), 7.71-7.49 (m, 4H), 7.37-7.33 (m, 1H), 7.03-6.89 (m, 3H), 6.02-5.33 (m, 1H), 3.76 (s, 3H), 3.42-2.70 (m, 7H), 1.55-1.25 (m, 18H). [α]$^{25°\ C}_D$=−92.8 (c=0.2 in MeOH)

Step 2: Compound tert-butyl (S)-(2-((2-((4-(1H-pyrazol-4-yl)phenyl)amino)-1-(3-methoxyphenyl)-2-oxoethyl)(tert-butoxycarbonyl)amino)ethyl)(methyl)carbamate was dissolved in dichloromethane and 4N HCl in dioxane was added. Reaction mixture stirred at room temperature for 4 hours and concentrated under reduced pressure. The final residue was purified by reverse phase preparative HPLC to afford (S)—N-(4-(1H-pyrazol-4-yl)phenyl)-2-(3-methoxyphenyl)-2-((2-(methylamino)ethyl)amino)acetamide a white solid (12%). $^1$H NMR (400 MHz, CD$_3$OD) δ 8.51 (s, 1H), 7.91 (s, 2H), 7.58-7.51 (m, 4H), 7.31 (t, J=7.6 Hz, 1H), 7.09-7.08 (m, 2H), 6.91-6.89 (m, 1H), 4.42 (s, 1H), 3.81 (s, 3H), 3.14-3.04 (m, 2H), 2.92-2.82 (m, 2H), 2.72 (s, 3H). MS (ES+) m/e 380.4 (M+H)+. [α]$^{25°\ C}_D$=+82.43 (0.7 in MeOH).

Example 64

(S)—N-(4-(1H-pyrazol-4-yl)phenyl)-2-(4-chlorophenyl)-2-(methylamino)acetamide

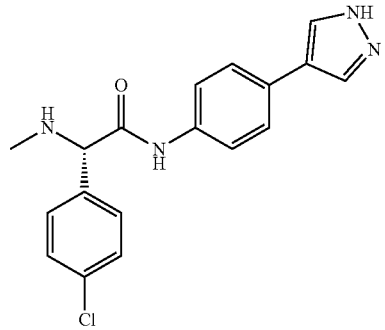 [SMILES: CN[C@H](C(=O)Nc1ccc(-c2cn[nH]c2)cc1)c1ccc(Cl)cc1]

Step 1: CbzNH$_2$ (3 equiv) was dissolved in n-propyl alcohol. 0.4 N NaOH (3 equiv) was added to the solution followed by tert-butyl-hypochlorite (1.05 equiv) in one portion. After 5 min, a solution of (DHQ)$_2$PHAL (0.05 equiv) in n-propyl alcohol was added into the reaction mixture in one portion. A solution of compound p-chloro styrene (1 equiv) in n-propyl alcohol was added in one portion, followed by K$_2$OsO$_2$(OH)$_4$ (0.03 equiv). The light green solution was stirred at 20° C. for an hour. Saturated solution of Na$_2$SO$_3$ was added into the reaction mixture and the mixture was stirred at 20° C. for 10 min. The organic layer was separated and water phase was extracted with EtOAc The combined organic layer was washed with brine dried with anhydrous Na$_2$SO$_4$, filtered and concentrated in vacuum. The residue was purified by prep-HPLC (TFA conditions) and freeze-dried to give compound benzyl (S)-(1-(4-chlorophenyl)-2-hydroxyethyl)carbamate (62%, 94.9% ee) as a white solid. $^1$H NMR (400 MHz, CDCl$_3$) δ 7.34-7.31 (m, 7H), 7.28-7.22 (m, 2H), 5.64 (s, 1H), 5.13-5.05 (m, 2H), 4.80 (s, 1H), 3.86-3.78 (m, 2H), 2.24 (m, 1H).

Step 2: To a mixture of compound (S)-1-(4-chlorophenyl)-2-hydroxyethyl)carbamate (1 equiv) and imidazole (2 equiv) in DMF was added TBSCl (1.5 equiv) in one portion at 30° C. under nitrogen. The mixture was stirred at 30° C. for 1 h. The mixture was poured into water and extracted with EtOAc. The combined organic layers was washed with brine, dried over with Na$_2$SO$_4$, filtered and concentrated under reduced pressure. The residue was purified by silica gel chromatography (SiO$_2$, petroleum ether/EtOAc=15/1) to afford benzyl (S)-(2-((tert-butyldimethylsilyl)oxy)-1-(4-chlorophenyl)ethyl)carbamate (95%, 89.3% ee) as a colorless oil. $^1$H NMR (400 MHz, CDCl$_3$) δ 7.38-7.25 (m, 9H), 5.59 (s, 1H), 5.16-5.07 (m, 2H), 4.77 (s, 1H), 3.95 (dd, J=10.0, 4.0 Hz, 1H), 3.75 (m, 1H), 0.89 (s, 9H), −0.03 (s, 3H), −0.06 (s, 3H).

Step 3: To a solution of compound (S)-(2-((tert-butyldimethylsilyl)oxy)-1-(4-chlorophenyl)ethyl)carbamate (1 equiv) in DMF was added NaH (2 equiv) portion-wise at 0° C. under nitrogen. The mixture was stirred at 0° C. for 10 min, and then a solution of MeI (1.5 equiv) in DMF was added dropwise into the mixture. The mixture was warmed to 20° C. and stirred for 50 min. The mixture was poured into saturated solution of NH$_4$Cl and extracted with EtOAc. The combined organic phase was washed with brine, dried with over Na$_2$SO$_4$, filtered and concentrated in vacuum. The mixture was purified by silica gel chromatography (SiO$_2$, petroleum ether/EtOAc=20/1) to afford benzyl (S)-(2-((tert-butyl dim ethyl silyl)oxy)-1-(4-chlorophenyl)ethyl)(methyl)carbamate (93%, 94.4% ee) as colorless oil. $^1$H NMR (400 MHz, CDCl$_3$) δ 7.36-7.19 (m, 9H), 5.37-5.22 (m, 1H), 5.19-5.04 (m, 2H), 4.05 (m, 2H), 2.80 (s, 3H), 0.88 (s, 9H), 0.07 (s, 6H).

Step 4: To a mixture of compound (S)-(2-((tert-butyldimethylsilyl)oxy)-1-(4-chlorophenyl)ethyl)(methyl)carbamate (1 equiv) in MeOH/H$_2$O (7:3) was added KHSO$_4$ (4 equiv) in one portion at 20° C. under N$_2$. Water was added into the reaction mixture and extracted with EtOAc. The organic layer was washed with brine, dried over Na$_2$SO$_4$, filtered and concentrated in vacuum. The residue was purified by silica gel chromatography (SiO$_2$, petroleum ether/EtOAc=2/1) to give compound benzyl (S)-(1-(4-chlorophenyl)-2-hydroxyethyl)(methyl)carbamate (99%, 94% ee) as colorless oil. $^1$H NMR (400 MHz, CDCl$_3$) δ 7.36-7.20 (m, 9H), 5.33 (dd, J=8.0, 6.4 Hz, 1H), 5.20 (m, 2H), 4.17-4.07 (m, 2H), 2.78 (s, 3H).

Step 5: A solution of compound (S)-(1-(4-chlorophenyl)-2-hydroxyethyl)(methyl)carbamate (1 equiv) in dissolved in sat. KH$_2$PO$_4$ and MeCN at 0° C. NaClO$_2$ (2 equiv) and TEMPO (0.2 equiv) was added into the reaction mixture at 0-5° C., followed by NaClO (2 equiv) dropwise at 0-5° C. under N$_2$. The mixture was turned into the deep-purple, and the reaction mixture was stirred at 10-15° C. for 2 h. The reaction mixture was diluted with H$_2$O (100 mL) and the mixture was extracted with DCM (100 mL×3). The combined organic phase was washed with brine (100 mL), dried with anhydrous Na$_2$SO$_4$, filtered and concentrated in vacuum. The residue was purified by silica gel chromatography (SiO$_2$, petroleum ether/EtOAc=1/1, 0/1) to give compound (S)-2-(((benzyloxy)carbonyl)(methyl)amino)-2-(4-chlorophenyl)acetic acid (95% 94% ee) as yellow oil.

Step 6: To a mixture of compound (S)-2-(((benzyloxy)carbonyl)-(methyl)amino)-2-(4-chlorophenyl)acetic acid (1 equiv) and compound 4-(1-(tetrahydro-2H-pyran-2-yl)-1H-pyrazol-4-yl)aniline (1.1 equiv) in THF was added DMT-MM (1.05) in one portion at 10° C. under N$_2$. The mixture was stirred at 20° C. for 3 hours. Water was added and the mixture was extracted with EtOAc. The combined organic phase was washed with brine, dried over Na$_2$SO$_4$, filtered and concentrated in vacuum. The residue was purified by prep-TLC (petroleum ether/EtOAc=2:1) to give compound benzyl ((1S)-1-(4-chlorophenyl)-2-oxo-2-((4-(1-(tetrahydro-2H-pyran-2-yl)-1H-pyrazol-4-yl)phenyl)amino) ethyl)-(methyl)carbamate (59%, 86% ee) as a yellow solid. $^1$H NMR (400 MHz, CDCl$_3$) δ 7.75 (s, 1H), 7.71 (s, 1H), 7.40-7.31 (m, 4H), 7.28-7.18 (m, 9H), 5.88 (s, 1H), 5.41 (dd, J=8.8, 2.8 Hz, 1H), 5.16-5.09 (m, 2H), 4.05-4.00 (m, 1H), 3.68-3.41 (m, 1H), 2.80 (s, 3H), 2.09-2.04 (m, 2H), 1.66-1.53 (m, 4H).

Step 7: To a solution of compound ((1S)-1-(4-chlorophenyl)-2-oxo-2-((4-(1-(tetrahydro-2H-pyran-2-yl)-1H-pyrazol-4-yl)phenyl)amino)ethyl)(methyl)carbamate (1 equiv) in MeCN was added TMSI (8 equiv) at 0° C. under N$_2$. H$_2$O was added and the mixture was extracted with petroleum ether. The aqueous phase was purification by prep-HPLC (FA conditions) to give (S)—N-(4-(1H-pyrazol-4-yl)phenyl)-2-(4-chlorophenyl)-2-(methylamino)acetamide (9%, 87.5% ee) as a white powder. $^1$H NMR (400 MHz, DMSO-d$_6$) δ 10.08 (s, 1H), 8.20 (s, 1H), 7.98 (s, 2H), 7.61-7.42 (m, 8H), 4.24 (s, 1H), 2.27 (s, 3H). MS (ES+) m/e 341.0 (M+H)$^+$.

Example 65

(R)—N-(4-(1H-pyrazol-4-yl)phenyl)-2-(4-chlorophenyl)-2-(methylamino)acetamide

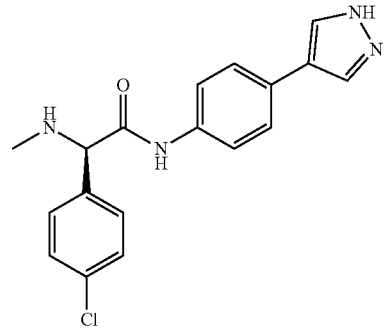 [SMILES: CN[C@@H](C(=O)Nc1ccc(-c2cn[nH]c2)cc1)c1ccc(Cl)cc1]

Step 1: CbzNH$_2$ (3 equiv) was dissolved in n-propyl alcohol. 0.4 N NaOH (3 equiv) was added to the solution followed by tert-butyl-hypochlorite (1.05 equiv) in one portion. After 5 min, a solution of (DHQD)$_2$PHAL (0.05 equiv) in n-propyl alcohol was added into the reaction mixture in one portion. A solution of compound p-chloro styrene (1 equiv) in n-propyl alcohol was added in one portion, followed by K$_2$OsO$_2$(OH)4 (0.03 equiv). The light green solution was stirred at 20° C. for an hour. Saturated solution of Na$_2$SO$_3$ was added into the reaction mixture and the mixture was stirred at 20° C. for 10 min. The organic layer was separated and water phase was extracted with EtOAc The combined organic layer was washed with brine dried with anhydrous Na$_2$SO$_4$, filtered and concentrated in vacuum. The residue was purified by prep-HPLC (TFA conditions) and freeze-dried to give compound benzyl (R)-(1-(4-chlorophenyl)-2-hydroxyethyl)carbamate (71%, 94.5% ee) as a white solid. $^1$H NMR (400 MHz, DMSO-d$_6$) δ 7.76 (d, J=8.4 Hz, 1H), 7.39-7.10 (m, 9H), 5.05-4.97 (m, 2H), 4.87 (t, J=5.6 Hz, 1H), 4.62-4.56 (m, 1H), 3.58-3.48 (m, 2H).

Step 2: To a mixture of compound (R)-(1-(4-chlorophenyl)-2-hydroxyethyl)carbamate (1 equiv) and imidazole (2 equiv) in DMF was added TBSCl (1.5 equiv) in one portion at 30° C. under nitrogen. The mixture was stirred at 30° C. for 1 h. The mixture was poured into water and extracted with EtOAc. The combined organic layers was washed with brine, dried over with Na$_2$SO$_4$, filtered and concentrated under reduced pressure. The residue was purified by silica gel chromatography (SiO$_2$, petroleum ether/EtOAc=15/1) to afford benzyl (R)-(2-((tert-butyl dim ethyl silyl)oxy)-1-(4-chlorophenyl)ethyl)carbamate (71%, 90% ee) as a colorless oil.

Step 3: To a solution of compound (R)-(2-((tert-butyldimethylsilyl)oxy)-1-(4-chlorophenyl)ethyl)carbamate (1 equiv) in DMF was added NaH (2 equiv) portion-wise at 0° C. under nitrogen. The mixture was stirred at 0° C. for 10 min, and then a solution of MeI (1.5 equiv) in DMF was added dropwise into the mixture. The mixture was warmed to 20° C. and stirred for 50 min. The mixture was poured into saturated solution of NH$_4$Cl and extracted with EtOAc. The combined organic phase was washed with brine, dried with over Na$_2$SO$_4$, filtered and concentrated in vacuum. The mixture was purified by silica gel chromatography (SiO$_2$, petroleum ether/EtOAc=20/1) to afford benzyl (R)-(2-((tert-butyldimethylsilyl)oxy)-1-(4-chlorophenyl)ethyl)(methyl)carbamate (75%, 93% ee) as colorless oil.

Step 4: To a mixture of compound (R)-(2-((tert-butyldimethylsilyl)oxy)-1-(4-chlorophenyl)ethyl)(methyl)carbamate (1 equiv) in MeOH/H$_2$O (7:3) was added KHSO$_4$ (4 equiv) in one portion at 20° C. under N$_2$. Water was added into the reaction mixture and extracted with EtOAc. The organic layer was washed with brine, dried over Na$_2$SO$_4$, filtered and concentrated in vacuum. The residue was purified by silica gel chromatography (SiO$_2$, petroleum ether/EtOAc=2/1) to give compound benzyl (R)-(1-(4-chlorophenyl)-2-hydroxyethyl)(methyl)carbamate (91%, 92% ee) as colorless oil.

Step 5: A solution of compound (R)-(1-(4-chlorophenyl)-2-hydroxyethyl)(methyl)carbamate (1 equiv) in dissolved in sat. KH$_2$PO$_4$ and MeCN at 0° C. NaClO$_2$ (2 equiv) and TEMPO (0.2 equiv) was added into the reaction mixture at 0-5° C., followed by NaClO (2 equiv) dropwise at 0-5° C. under N$_2$. The mixture was turned into the deep-purple, and the reaction mixture was stirred at 10-15° C. for 2 h. The reaction mixture was diluted with H$_2$O (100 mL) and the mixture was extracted with DCM (100 mL×3). The combined organic phase was washed with brine (100 mL), dried with anhydrous Na$_2$SO$_4$, filtered and concentrated in vacuum. The residue was purified by silica gel chromatography (SiO$_2$, petroleum ether/EtOAc=1/1, 0/1) to give compound (R)-2-(((benzyloxy)carbonyl)-(methyl)amino)-2-(4-chlorophenyl)acetic acid (94% ee) as yellow oil.

Step 6: To a mixture of compound (R)-2-(((benzyloxy)carbonyl)(methyl)amino)-2-(4-chlorophenyl)acetic acid (1 equiv) and compound 4-(1-(tetrahydro-2H-pyran-2-yl)-1H-pyrazol-4-yl)aniline (1.1 equiv) in THF was added DMT-MM (1.05) in one portion at 10° C. under N$_2$. The mixture was stirred at 20° C. for 3 hours. Water was added and the mixture was extracted with EtOAc. The combined organic phase was washed with brine, dried over Na$_2$SO$_4$, filtered and concentrated in vacuum. The residue was purified by prep-TLC (petroleum ether/EtOAc=2:1) to give compound benzyl ((1R)-1-(4-chlorophenyl)-2-oxo-2-((4-(1-(tetrahydro-2H-pyran-2-yl)-1H-pyrazol-4-yl)phenyl)amino)ethyl)(methyl)carbamate (83%, 87% ee) as a yellow solid. $^1$H NMR (400 MHz, CDCl$_3$) δ 7.75 (s, 1H), 7.71 (s, 1H), 7.40-7.31 (m, 4H), 7.28-7.18 (m, 9H), 5.88 (s, 1H), 5.41 (dd, J=8.8, 2.8 Hz, 1H), 5.16-5.09 (m, 2H), 4.05-4.00 (m, 1H), 3.68-3.41 (m, 1H), 2.80 (s, 3H), 2.09-2.04 (m, 2H), 1.66-1.53 (m, 4H).

Step 7: To a solution of compound ((1R)-1-(4-chlorophenyl)-2-oxo-2-((4-(1-(tetrahydro-2H-pyran-2-yl)-1H-pyrazol-4-yl)phenyl)amino)ethyl)(methyl)carbamate (1 equiv) in MeCN was added TMSI (8 equiv) at 0° C. under N$_2$. H$_2$O was added and the mixture was extracted with petroleum ether. The aqueous phase was purification by prep-HPLC (FA conditions) to give (R)—N-(4-(1H-pyrazol-4-yl)phenyl)-2-(4-chlorophenyl)-2-(methylamino)acetamide (28%, 87% ee) as a white powder. $^1$H NMR (400 MHz, DMSO-d$_6$) δ 10.15 (s, 1H), 8.14 (s, 1H), 7.98 (s, 2H), 7.59 (d, J=8.8 Hz, 4H), 7.54-7.49 (m, 4H), 7.44-7.42 (m, 2H), 4.32 (s, 1H), 2.30 (s, 3H). MS (ES+) m/e 341.3 (M+H)$^+$.

Example 66

N-(2-fluoro-5-methoxy-4-(1H-pyrazol-4-yl)phenyl)-2-(3-methoxyphenyl)-2-(methylamino)acetamide

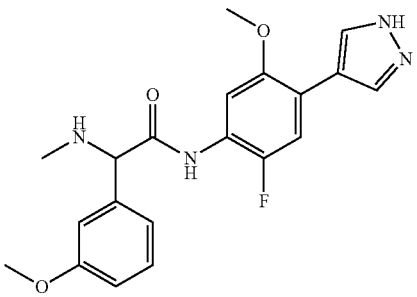 [SMILES: CNC(C(=O)Nc1cc(OC)c(-c2cn[nH]c2)cc1F)c1cccc(OC)c1]

The reaction was conducted following general procedure A. The final residue was purified by reverse phase preparative HPLC to afford N-(2-fluoro-5-methoxy-4-(1H-pyrazol-4-yl)phenyl)-2-(3-methoxyphenyl)-2-(methylamino)acetamide as a yellow oil (1%). $^1$H NMR (400 MHz, DMSO-d$_6$) δ 12.91 (s, 1H), 9.91 (brs, 1H), 8.07 (s, 2H), 7.74 (d, J=7.2 Hz, 1H), 7.58 (d, J=12.4 Hz, 1H), 7.27 (t, J=8.0 Hz, 1H), 7.04-7.01 (m, 2H), 6.86 (dd, J=7.2, 1.6 Hz, 1H), 4.28 (s, 1H), 3.80 (s, 3H), 3.75 (s, 3H), 2.31 (s, 3H). MS (ES+) m/e 385.2 (M+H)$^+$.

Example 67

3-(2-((4-(1H-pyrazol-4-yl)phenyl)amino)-1-(methylamino)-2-oxoethyl)-N-methylbenzamide

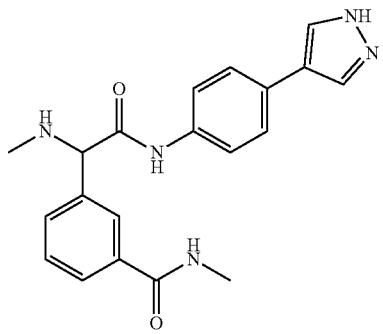 [SMILES: CNC(=O)c1cccc(C(NC)C(=O)Nc2ccc(-c3cn[nH]c3)cc2)c1]

Step 1: To a solution of compound methyl 3-(1-((4-methoxybenzyl)(methyl)amino)-2-oxo-2-((4-(1-(tetrahydro-2H-pyran-2-yl)-1H-pyrazol-4-yl)phenyl)amino)ethyl)benzoate (1 equiv) in MeOH and water was added NaOH (2 equiv). The mixture was concentrated under vacuum. The residue was purified by prep-HPLC (FA conditions) to afford compound 3-(1-((4-methoxybenzyl)

(methyl)amino)-2-oxo-2-((4-(1-(tetrahydro-2H-pyran-2-yl)-1H-pyrazol-4-yl)phenyl)amino)ethyl)benzoic acid (58%) as an off-white solid. $^1$H NMR (400 MHz, DMSO-d$_6$) δ 10.21 (s, 1H), 8.27 (s, 1H), 8.15 (s, 1H), 7.95-7.90 (m, 2H), 7.88 (d, J=8.0 Hz, 1H), 7.63-7.55 (m, 5H), 7.27 (d, J=8.8 Hz, 2H), 6.89 (d, J=8.8 Hz, 2H), 5.38 (dd, J=10.4, 2.4 Hz, 1H), 4.33 (s, 1H), 3.92 (d, J=11.6 Hz, 1H), 3.73 (s, 3H), 3.66-3.63 (m, 1H), 3.51-3.42 (m, 2H), 2.16-2.09 (m, 4H), 1.94 (s, 2H), 1.69-1.65 (m, 1H), 1.58-1.54 (m, 2H).

Step 2: To a solution of compound 3-(1-((4-methoxybenzyl)(methyl)amino)-2-oxo-2-((4-(1-(tetrahydro-2H-pyran-2-yl)-1H-pyrazol-4-yl)phenyl)amino)ethyl)benzoic acid (1 equiv), methylamine (1 equiv)) in CH$_3$CN were added T$_3$P (1.5 equiv), DIPEA (1.5 equiv) at 20° C. The mixture was heated to 80° C. and stirred for 15 hr. The reaction mixture was diluted with H$_2$O and extracted with EtOAc. The combined organic layers were washed with brine, dried over Na$_2$SO$_4$, filtered and concentrated under reduced pressure to give a compound 3-(1-((4-methoxybenzyl)(methyl)amino)-2-oxo-2-((4-(1-(tetrahydro-2H-pyran-2-yl)-1H-pyrazol-4-yl)phenyl)amino)ethyl)-N-methylbenzamide as a white solid.

Step 3: A mixture of compound 3-(1-((4-methoxybenzyl)(methyl)amino)-2-oxo-2-((4-(1-(tetrahydro-2H-pyran-2-yl)-1H-pyrazol-4-yl)phenyl)amino)ethyl)-N-methylbenzamide in TFA was stirred at 75° C. for 16 hr. The mixture was concentrated under vacuum to give a residue. The residue was purified by prep-HPLC (TFA conditions) to afford 3-(2-((4-(1H-pyrazol-4-yl)phenyl)amino)-1-(methylamino)-2-oxoethyl)-N-methylbenzamide as a white solid (43%). $^1$H NMR (400 MHz, DMSO-d$_6$) δ 10.69 (s, 1H), 9.61-9.47 (m, 2H), 8.56 (d, J=4.8 Hz, 1H), 8.12 (s, 1H), 8.01 (s, 2H), 7.93 (d, J=7.6 Hz, 1H), 7.73 (d, J=8.0 Hz, 1H), 7.63-7.54 (m, 5H), 5.09 (s, 1H), 2.81 (s, 3H), 2.53 (s, 3H). MS (ES+) m/e 364.4 (M+H)$^+$.

Example 68

4-(2-((4-(1H-pyrazol-4-yl)phenyl)amino)-1-(methylamino)-2-oxoethyl)benzoic acid

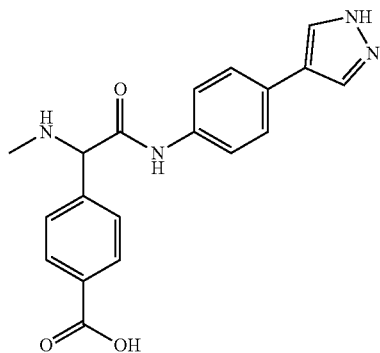 [SMILES: CNC(C(=O)Nc1ccc(-c2cn[nH]c2)cc1)c1ccc(C(=O)O)cc1]

Step 1: The mixture of compound methyl 4-(1-(4-methoxybenzyl)-(methyl)amino)-2-oxo-2-((4-(1-(tetrahydro-2H-pyran-2-yl)-1H-pyrazol-4-yl)phenyl)amino)ethyl)benzoate (1 equiv) in TFA was stirred at 70° C. for 112 hr. The reaction mixture was diluted with MeOH and concentrated under reduced pressure to give a residue. The residue was purified by prep-HPLC (TFA conditions) to afford compound methyl 4-(2-((4-(1H-pyrazol-4-yl)phenyl)amino)-1-(methylamino)-2-oxoethyl)benzoate (19%) as an off-white solid. $^1$H NMR (400 MHz, CD$_3$OD) δ 8.17 (dd, J=6.8, 2.0 Hz, 2H), 7.92 (s, 2H), 7.74 (d, J=8.4 Hz, 2H), 7.58-7.53 (m, 4H), 5.07 (s, 1H), 3.92 (s, 3H), 2.70 (s, 3H).

Step 2: To a solution of compound methyl 4-(2-((4-(1H-pyrazol-4-yl)phenyl)amino)-1-(methylamino)-2-oxoethyl)benzoate (1 equiv) in MeOH and H$_2$O was added NaOH (3 equiv). The mixture was stirred at 30° C. for 16 hr. The mixture was acidified to pH=5 with 1N HCl The resulting mixture was purified by prep-HPLC (FA conditions) to afford 4-(2-((4-(1H-pyrazol-4-yl)phenyl)amino)-1-(methylamino)-2-oxoethyl)benzoic acid (, 18%) as a white solid. $^1$H NMR (400 MHz, DMSO-d$_6$) δ 10.13 (s, 1H), 8.27 (s, 1H), 7.98 (s, 2H), 7.90 (d, J=8.4 Hz, 2H), 7.65-7.50 (m, 6H), 4.30 (s, 1H), 2.28 (s, 3H). MS (ES+) m/e 351.1 (M+H)$^+$.

Example 69

4-(2-((4-(1H-pyrazol-4-yl)phenyl)amino)-1-(methylamino)-2-oxoethyl)-N-methylbenzamide

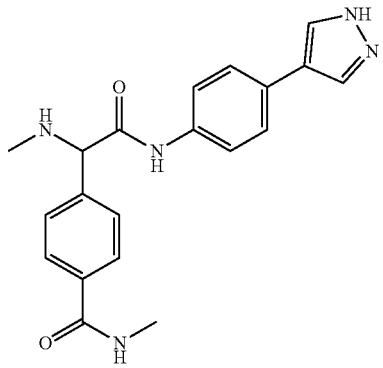 [SMILES: CNC(=O)c1ccc(C(NC)C(=O)Nc2ccc(-c3cn[nH]c3)cc2)cc1]

Step 1: To a solution of compound methyl 4-(1-((4-methoxybenzyl)-(methyl)amino)-2-oxo-2-((4-(1-(tetrahydro-2H-pyran-2-yl)-1H-pyrazol-4-yl)phenyl)amino)ethyl)benzoate (1 equiv) in MeOH and H$_2$O was added NaOH (2 equiv). The mixture was stirred at 35° C. for 36 hours. The reaction mixture was diluted with H$_2$O. The resulting solution was purified by prep-HPLC (FA conditions) to give compound 4-(1-((4-methoxybenzyl)(methyl)amino)-2-oxo-2-((4-(1-(tetrahydro-2H-pyran-2-yl)-1H-pyrazol-4-yl)phenyl)amino)ethyl)benzoic acid (70%, 98% purity) as a white solid. $^1$H NMR (400 MHz, DMSO-d$_6$) δ 12.92 (s, 1H), 10.19 (s, 1H), 7.97 (d, J=8.4 Hz, 2H), 7.88 (s, 1H), 7.69 (d, J=8.4 Hz, 2H), 7.65-7.60 (m, 2H), 7.59-7.52 (m, 2H), 7.28 (d, J=8.8 Hz, 2H), 6.90 (d, J=8.4 Hz, 2H), 5.38 (dd, J=10.0, 2.4 Hz, 1H), 4.33 (s, 1H), 3.94-3.92 (m, 1H), 3.74 (s, 3H), 3.68-3.58 (m, 1H), 3.54-3.40 (m, 2H), 2.18-2.03 (m, 4H), 2.00-1.87 (m, 2H), 1.75-1.61 (m, 1H), 1.59-1.48 (m, 2H).

Step 2: To a solution of compound 4-(1-((4-methoxybenzyl)(methyl)amino)-2-oxo-2-((4-(1-(tetrahydro-2H-pyran- 2-yl)-1H-pyrazol-4-yl)phenyl)amino)ethyl)benzoic acid (1 equiv) in MeCN was added T₃P (1.5 equiv), MeNH₂ (2.5 equiv) and DIPEA (4 equiv). The mixture was stirred at 30° C. for 36 hr. The reaction mixture was cooled down to room temperature and quenched by addition H₂O at 15° C. The resulting mixture was diluted with EtOAc and extracted with EtOAc. The combined organic layers were washed with brine, dried over Na₂SO₄, filtered and concentrated under reduced pressure to give compound 4-(1-((4-methoxybenzyl)(methyl)amino)-2-oxo-2-((4-(1-(tetrahydro-2H-pyran-2-yl)-1H-pyrazol-4-yl)phenyl)amino)ethyl)-N-methylbenzamide (98%, 87% purity) as a white solid.

Step 3: To a solution of compound 4-(1-((4-methoxybenzyl)(methyl)amino)-2-oxo-2-((4-(1-(tetrahydro-2H-pyran-2-yl)-1H-pyrazol-4-yl)phenyl)amino)ethyl)-N-methylbenzamide (1 equiv) in THF and MeOH was added dry Pd/C (0.1 equiv) and HCl (2 equiv). The mixture was stirred at 50° C. for 2 hr under an atmosphere of H₂ (1 atm). The mixture was cooled to room temperature and filtered. The filtrate was concentrated under reduced pressure to give a residue. The residue was purified by prep-HPLC (FA conditions) to afford 4-(2-((4-(1H-pyrazol-4-yl)phenyl)amino)-1-(methylamino)-2-oxoethyl)-N-methylbenzamide (98% purity) as a white solid. $^1$H NMR (400 MHz, DMSO-d₆) δ 10.13 (s, 1H), 8.44-8.36 (m, 1H), 8.16 (s, 1H), 7.98 (s, 2H), 7.80 (d, J=8.4 Hz, 2H), 7.63-7.58 (m, 2H), 7.57-7.51 (m, 4H), 4.30 (s, 1H), 2.76 (d, J=4.4 Hz, 3H), 2.29 (s, 3H). MS (ES+) m/e 364.3 (M+H)⁺.

Example 70

N-(2-(3-(dimethylamino)propoxy)-5-fluoro-4-(1H-pyrazol-4-yl)phenyl)-2-(3-methoxyphenyl)-2-(methylamino)acetamide

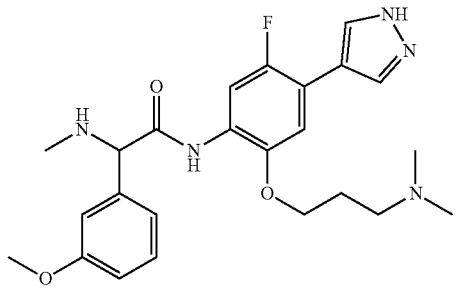

The reaction was conducted following general procedure A. The final residue was purified by reverse phase preparative HPLC to afford N-(2-(3-(dimethylamino)propoxy)-5-fluoro-4-(1H-pyrazol-4-yl)phenyl)-2-(3-methoxyphenyl)-2-(methylamino)acetamide as a white solid (13%). $^1$H NMR (400 MHz, CD₃OD) δ 8.04 (d, J=12.8 Hz, 1H), 8.00 (s, 2H), 7.30-7.23 (m, 2H), 7.03-7.02 (m, 2H), 6.88 (dd, J=8.4, 0.8 Hz, 1H), 4.20 (s, 1H), 4.16 (t, J=6.0 Hz, 2H), 3.79 (s, 3H), 2.62-2.58 (m, 2H), 2.45 (s, 3H), 2.30 (s, 6H), 2.07-2.00 (m, 2H). MS (ES+) m/e 456.4 (M+H)⁺.

Example 71

N-(2-(2-(dimethylamino)ethoxy)-5-fluoro-4-(1H-pyrazol-4-yl)phenyl)-2-(3-methoxyphenyl)-2-(methylamino)acetamide

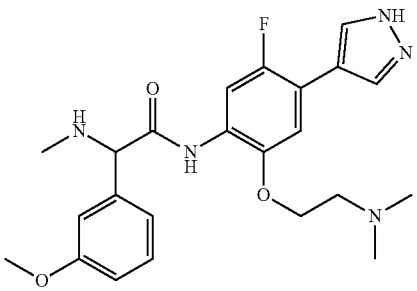

The reaction was conducted following general procedure A. The final residue was purified by reverse phase preparative HPLC to afford N-(2-(2-(dimethylamino)ethoxy)-5-fluoro-4-(1H-pyrazol-4-yl)phenyl)-2-(3-methoxyphenyl)-2-(methylamino)acetamide as a white solid (37%). $^1$H NMR (400 MHz, CD₃OD) δ 8.52 (s, 2H), 8.04-8.0 (m, 3H), 7.42 (t, J=8.0 Hz, 1H), 7.28 (d, J=6.8 Hz, 1H), 7.24-7.19 (m, 2H), 7.05 (dd, J=8.8, 2.4 Hz, 1H), 5.43 (s, 1H), 4.44-4.41 (m, 1H), 4.27-4.25 (m, 1H), 3.84 (s, 3H), 3.41-3.36 (m, 2H), 2.81 (s, 6H), 2.65 (s, 3H). MS (ES+) m/e 442.4 (M+H)⁺.

Example 72

(R)—N-(2-(2-(dimethylamino)ethoxy)-5-fluoro-4-(1H-pyrazol-4-yl)phenyl)-2-(3-methoxyphenyl)-2-(methylamino)acetamide

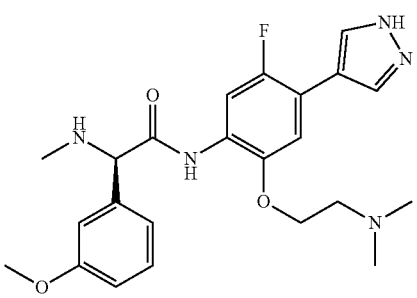

The reaction was conducted following general procedure A. The final residue was purified by reverse phase preparative HPLC to afford N-(2-(2-(dimethylamino)ethoxy)-5-fluoro-4-(1H-pyrazol-4-yl)phenyl)-2-(3-methoxyphenyl)-2-(methylamino)acetamide as a white solid (37%). Enantiomers were separated by SFC (DAICEL CHIRALPAK AD column). Mobile phase: 55% EtOH with 0.1% NH₄OH in CO₂, flow rate 70 g/min to afford (R)—N-(2-(2-(dimethylamino)ethoxy)-5-fluoro-4-(1H-pyrazol-4-yl)phenyl)-2-(3-methoxyphenyl)-2-(methylamino)acetamide with 99% enantiomeric purity. $^1$H NMR (400 MHz, DMSO-d₆) δ 11.05 (s, 1H), 10.59 (s, 1H), 9.98-9.96 (m, 1H), 9.72-9.69 (m, 1H), 8.08 (m, 2H), 7.94 (d, J=12.4 Hz, 1H), 7.47 (s, 1H), 7.43-7.34 (m, 3H), 7.04-7.01 (m, 1H), 6.05 (t, J=6.4 Hz, 1H), 4.47-4.34 (m, 2H), 3.79 (s, 3H), 3.58-3.49 (m, 2H), 2.83 (dd, J=7.2, 5.2 Hz, 6H), 2.48 (s, 3H). MS (ES+) m/e 442.3 (M+H)⁺.

Example 73

(S)—N-(2-(2-(dimethylamino)ethoxy)-5-fluoro-4-(1H-pyrazol-4-yl)phenyl)-2-(3-methoxyphenyl)-2-(methylamino)acetamide

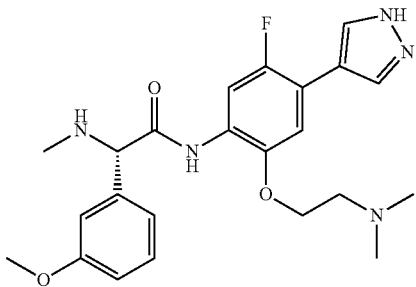

The reaction was conducted following general procedure A. The final residue was purified by reverse phase preparative HPLC to afford N-(2-(2-(dimethylamino)ethoxy)-5-fluoro-4-(1H-pyrazol-4-yl)phenyl)-2-(3-methoxyphenyl)-2-(methylamino)acetamide as a white solid (37%). Enantiomers were separated by SFC (DAICEL CHIRALPAK AD column). Mobile phase: 55% EtOH with 0.1% NH₄OH in CO₂, flow rate 70 g/min to afford (S)—N-(2-(2-(dimethylamino)ethoxy)-5-fluoro-4-(1H-pyrazol-4-yl)phenyl)-2-(3-methoxyphenyl)-2-(methylamino)acetamide with 99% enantiomeric purity. ¹H NMR (400 MHz, DMSO-d₆) δ 11.05 (s, 1H), 10.59 (s, 1H), 9.97-9.94 (m, 1H), 9.71-9.68 (m, 1H), 8.08 (m, 2H), 7.94 (d, J=12.4 Hz, 1H), 7.47 (s, 1H), 7.43-7.36 (m, 3H), 7.04-7.02 (m, 1H), 6.05 (t, J=6.4 Hz, 1H), 4.48-4.34 (m, 2H), 3.79 (s, 3H), 3.58-3.47 (m, 2H), 2.83 (dd, J=7.2, 5.2 Hz, 6H), 2.48 (s, 3H). MS (ES+) m/e 442.3 (M+H)⁺.

Example 74

1-(4-(1H-pyrazol-4-yl)phenyl)-4-(cyclopropylmethyl)-3-(3-methoxyphenyl)-1,4-diazepan-2-one

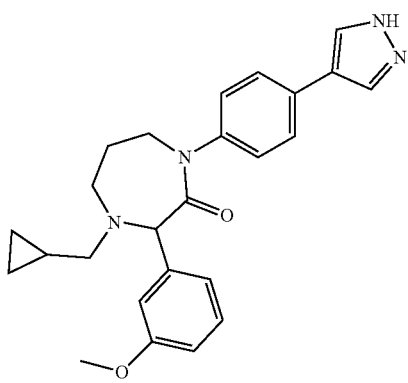 [SMILES: COc1cccc(C2C(=O)N(c3ccc(-c4cn[nH]c4)cc3)CCCN2CC2CC2)c1]

Step 1: To a mixture of compound benzyl 2-(3-methoxyphenyl)-3-oxo-1,4-diazepane-1-carboxylate (1 equiv) and compound 4-(4-iodophenyl)-1-(tetrahydro-2H-pyran-2-yl)-1H-pyrazole (1 equiv) in dioxane were added Cs₂CO₃ (4 equiv) and Xantphos-Pd-G3 (0.05 equiv) at 20° C. under N₂. The mixture was stirred at 100° C. for 16 h. The mixture was extracted with EtOAc (100 mL×4). The combined organic phase was washed with brine (100 mL), dried with anhydrous Na₂SO₄, filtered and concentrated in vacuum. The residue was purified by silica gel chromatography (SiO₂, petroleum ether/EtOAc=2/1, 1/1) to give compound benzyl 2-(3-methoxyphenyl)-3-oxo-4-(4-(1-(tetrahydro-2H-pyran-2-yl)-1H-pyrazol-4-yl)phenyl)-1,4-diazepane-1-carboxylate (25%) as a yellow oil.

Step 2: To a solution of compound benzyl 2-(3-methoxyphenyl)-3-oxo-4-(4-(1-(tetrahydro-2H-pyran-2-yl)-1H-pyrazol-4-yl)phenyl)-1,4-diazepane-1-carboxylate (1 equiv) in MeOH was added dry Pd/C (0.1 equiv) under N₂. The suspension was degassed under vacuum and purged with H₂ several times. The mixture was stirred under H₂ (15 psi) at 20° C. for 4 h. The reaction mixture was filtered and the filtrate was concentrated to give residue. The residue was purified by prep-HPLC (FA conditions) to give compound 3-(3-methoxyphenyl)-1-(4-(1-(tetrahydro-2H-pyran-2-yl)-1H-pyrazol-4-yl)phenyl)-1,4-diazepan-2-one (67%) as a white solid.

Step 3: To a mixture of compound 3-(3-methoxyphenyl)-1-(4-(1-(tetrahydro-2H-pyran-2-yl)-1H-pyrazol-4-yl)phenyl)-1,4-diazepan-2-one (1 equiv) and aldehyde (2 equiv) in MeOH was added TEA (3) in one portion at 25° C. under N₂. The mixture was stirred at 25° C. for 30 min. NaBH(OAc)₃ (4 equiv) was added into the reaction, and the reaction mixture was stirred at 25° C. for 4 h. The mixture was poured into water and extracted with EtAOc. The combined organic layer was dried with anhydrous Na₂SO₄, filtered and concentrated in vacuum. The residue was purified by silica gel chromatography (SiO₂, petroleum ether/EtOAc=2/1, 1/1) to give compound 4-(cyclopropylmethyl)-3-(3-methoxyphenyl)-1-(4-(1-(tetrahydro-2H-pyran-2-yl)-1H-pyrazol-4-yl)phenyl)-1,4-diazepan-2-one (32%) as colorless oil.

Step 4: To a mixture of compound 4-(cyclopropylmethyl)-3-(3-methoxyphenyl)-1-(4-(1-(tetrahydro-2H-pyran-2-yl)-1H-pyrazol-4-yl)phenyl)-1,4-diazepan-2-one (1 equiv) in DCM was added TFA at 0° C. under N₂. The mixture was stirred at 0° C. for 10 min, and the reaction mixture was warmed to 25° C. The reaction mixture was stirred at 25° C. for 0.5 hour. The reaction mixture was concentrated in reduced pressure at 45° C. and the residue was purified by prep-HPLC to give 1-(4-(1H-pyrazol-4-yl)phenyl)-4-(cyclopropylmethyl)-3-(3-methoxyphenyl)-1,4-diazepan-2-one (7%) as an off-white solid. ¹H NMR (400 MHz, CD₃OD) δ 7.99 (s, 2H), 7.69-7.65 (m, 2H), 7.45 (t, J=8.0 Hz, 1H), 7.34-7.30 (m, 2H), 7.26-7.24 (m, 2H), 7.09 (dd, J=8.8, 1.6 Hz, 1H), 5.73 (s, 1H), 4.40 (m, 1H), 3.99-3.83 (m, 6H), 3.38-3.32 (m, 1H), 3.31-3.20 (m, 1H), 2.38 (m, 2H), 1.15-1.10 (m, 1H), 0.78-0.73 (m, 2H), 0.38-0.34 (m, 2H). MS (ES+) m/e 417.3 (M+H)⁺.

Example 75

1-(4-(1H-pyrazol-4-yl)phenyl)-4-(2-(dimethylamino)ethyl)-3-(3-methoxyphenyl)-1,4-diazepan-2-one

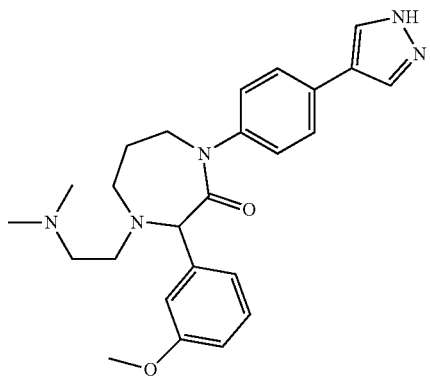 [SMILES: COc1cccc(C2C(=O)N(c3ccc(-c4cn[nH]c4)cc3)CCCN2CCN(C)C)c1]

Step 1: To a mixture of compound 3-(3-methoxyphenyl)-1-(4-(1-(tetrahydro-2H-pyran-2-yl)-1H-pyrazol-4-yl)phenyl)-1,4-diazepan-2-one (1 equiv) and aldehyde (2 equiv) in MeOH was added TEA (3) in one portion at 25° C. under $N_2$. The mixture was stirred at 25° C. for 30 min. NaBH(OAc)$_3$ (4 equiv) was added into the reaction, and the reaction mixture was stirred at 25° C. for 4 h. The mixture was poured into water and extracted with EtAOc. The combined organic layer was dried with anhydrous $Na_2SO_4$, filtered and concentrated in vacuum. The residue was purified by silica gel chromatography ($SiO_2$, petroleum ether/EtOAc=2/1, 1/1) to give compound 4-(2-(dimethylamino)ethyl)-3-(3-methoxyphenyl)-1-(4-(1-(tetrahydro-2H-pyran-2-yl)-1H-pyrazol-4-yl)phenyl)-1,4-diazepan-2-one (13%) as colorless oil.

Step 2: To a mixture of compound 4-(2-(dimethylamino)ethyl)-3-(3-methoxyphenyl)-1-(4-(1-(tetrahydro-2H-pyran-2-yl)-1H-pyrazol-4-yl)phenyl)-1,4-diazepan-2-one (1 equiv) in DCM was added TFA at 0° C. under $N_2$. The mixture was stirred at 0° C. for 10 min, and the reaction mixture was warmed to 25° C. The reaction mixture was stirred at 25° C. for 0.5 hour. The reaction mixture was concentrated in reduced pressure at 45° C. and the residue was purified by prep-HPLC to give 1-(4-(1H-pyrazol-4-yl)phenyl)-4-(2-(dimethylamino)ethyl)-3-(3-methoxyphenyl)-1,4-diazepan-2-one (40%) as a yellow solid. $^1$H NMR (400 MHz, CD$_3$OD) δ 8.00 (s, 2H), 7.68 (d, J=8.8 Hz, 2H), 7.42 (t, J=8.0 Hz, 1H), 7.30 (d, J=8.4 Hz, 2H), 7.19-7.15 (m, 2H), 6.98 (dd, J=8.0, 2.4 Hz, 1H), 5.06 (s, 1H), 3.93-3.86 (m, 4H), 3.77-3.73 (m, 1H), 3.48-3.35 (m, 4H), 3.22-3.14 (m, 2H), 2.94 (s, 3H), 2.87 (s, 3H), 2.19-2.17 (m, 1H), 1.77 (m, 1H). MS (ES+) m/e 434.3 (M+H)$^+$.

Example 76

1-(4-(1H-pyrazol-4-yl)phenyl)-3-(3-methoxyphenyl)-4-(2-(methylamino)ethyl)-1,4-diazepan-2-one

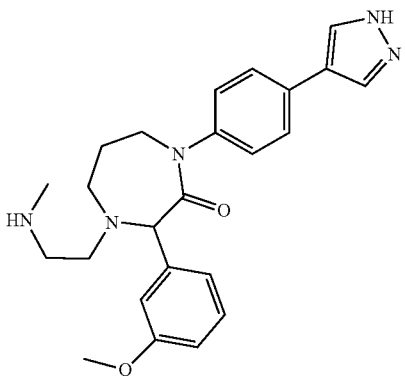 [SMILES: CNCCN1CCCN(c2ccc(-c3cn[nH]c3)cc2)C(=O)C1c1cccc(OC)c1]

Step 1: To a mixture of compound 3-(3-methoxyphenyl)-1-(4-(1-(tetrahydro-2H-pyran-2-yl)-1H-pyrazol-4-yl)phenyl)-1,4-diazepan-2-one (1 equiv) and aldehyde (2 equiv) in MeOH was added TEA (3) in one portion at 25° C. under $N_2$. The mixture was stirred at 25° C. for 30 min. NaBH(OAc)$_3$ (4 equiv) was added into the reaction, and the reaction mixture was stirred at 25° C. for 4 h. The mixture was poured into water and extracted with EtAOc. The combined organic layer was dried with anhydrous $Na_2SO_4$, filtered and concentrated in vacuum. The residue was purified by silica gel chromatography ($SiO_2$, petroleum ether/EtOAc=2/1, 1/1) to give compound tert-butyl (2-(2-(3-methoxyphenyl)-3-oxo-4-(4-(1-(tetrahydro-2H-pyran-2-yl)-1H-pyrazol-4-yl)phenyl)-1,4-diazepan-1-yl)ethyl)(methyl)carbamate (77%) as an off-white oil.

Step 2: To a mixture of compound tert-butyl (2-(2-(3-methoxyphenyl)-3-oxo-4-(4-(1-(tetrahydro-2H-pyran-2-yl)-1H-pyrazol-4-yl)phenyl)-1,4-diazepan-1-yl)ethyl)(methyl)carbamate (1 equiv) in DCM was added TFA at 0° C. under $N_2$. The mixture was stirred at 0° C. for 10 min, and the reaction mixture was warmed to 25° C. The reaction mixture was stirred at 25° C. for 0.5 hour. The reaction mixture was concentrated in reduced pressure at 45° C. and the residue was purified by prep-HPLC to give 11-(4-(1H-pyrazol-4-yl)phenyl)-3-(3-methoxyphenyl)-4-(2-(methylamino)ethyl)-1,4-diazepan-2-one (66%) as a white solid. $^1$H NMR (400 MHz, CD$_3$OD) δ 8.00 (s, 2H), 7.67 (d, J=8.4 Hz, 2H), 7.40 (t, J=8.0 Hz, 1H), 7.28 (d, J=8.8 Hz, 2H), 7.16-7.13 (m, 2H), 7.67 (dd, J=8.4, 2.4 Hz, 1H), 5.03 (s, 1H), 3.90-3.87 (m, 1H), 3.84 (s, 3H), 3.73-3.66 (m, 1H), 3.39-3.34 (m, 1H), 3.23-3.08 (m, 5H), 2.73 (s, 3H), 2.17-2.14 (m, 1H), 1.71-1.68 (m, 1H). MS (ES+) m/e 420.3 (M+H)$^+$.

Example 77

Determination of compounds ROCK inhibitory activity in vitro (Z'lyte assay): recombinant ROCK1 (amino acids 1-535) and ROCK2 (amino acids 1-552) proteins were purchased from ThermoFisher Scientific. Compounds activities were measured by Z'-lyte kinase kit (ThermoFisher Scientific) and IC50s were calculated.

Example 78

Determination of compounds ROCK inhibitory activity in A7R5 cells: rat aortic smooth muscle cell line A7R5 cells were maintained and treated in DMEM medium with 10% of fetal bovine serum. Cells were seeded with density of 5,000 cells/well in 96-well plates for 24 hours and subsequently treated 90 min with testing compounds. Cells were then fixed and processed according to the In-Cell ELISA Colorimetric Detection Kit manual (Thermo Scientific).

Example 79

NIH3T3 cells Acta2-promoter driven-luciferase assay: A NIH3T3 cell line stably expressing a luciferase reporter driven by the human ACTA2 gene promoter (−1000-1 bp) was established (NIH3T3-Acta2-luciferase). The cells were plated to confluence and treated with the test compounds plus TGFβ1 for 24 hr. Cells were then lysed and luciferase activity was measured using the LightSwitch luciferase kit from Active Motif.

Example 80

Thawing and proliferation of human oligodendrocyte/neuron progenitor cells (OPCs). Cryopreserved human oligodendrocyte/neuron progenitors (Millipore Cat. No. CS204496) were recovered and cultured on maltrigel (BD Cat. No. 356324) coated T-25 flask in expansion media containing OPC/neuron basal medium, N21 medium supplement, recombinant human bFGF, PDGF-AA and NT-3. When cells reached 80% confluent, 3 ml of Accutase was applied (Millipore SCR005) to passage cells at 1:4 ratio. Sub-cultured cells were maintained in expansion media for proliferation.

Example 81

Spontaneous differentiation of human oligodendrocyte/neuron progenitors in 24-well and 96-well plates. Coat plate with 10 µg/ml poly-L-ornithine (Sigma Cat. No. P4957) overnight at room temperature. Remove the poly-L-ornithine solution and rinse the plate with 1×PBS, add 10 µg/ml laminin (Millipore Cat. No. CC095) and incubate at 37° C. for at least 2 hours. Seed cells on the coated plates in expansion media and allowed to attach overnight. The next day expansion media was removed and replaced with freshly prepared spontaneous differentiation media only containing OPC/neuron basal media and N21 media supplement. For 14 day culture, differentiation media was replaced every 3-4 days. Cells were imaged and neurite length was analyzed by IncuCyte S3 Live Cell Analysis System every 4 hours. After 14 days of differentiation, cells were fixed by 4% paraformaldehyde and stained with DAPI and Neuron-specific ß-III tubulin antibody (R&D systems, NL1195R).

Example 82

Chondroitin Sulfate Proteoglycan (CSPG) assay on human oligodendrocyte/neuron progenitors in 96-well plate. After an overnight incubation with 10 µg/ml poly-L-ornithine, 96-well plates were coated with well mixed solution of 10 µg/ml laminin in combination with 0.3 µg/ml CSPG (Millipore CC117) for at least 2 hours at room temperature. Cells were seeded on the coated plates at a density of 6,000 cells per well in expansion media. The following day the expansion media was replaced with fresh spontaneous differentiation media containing testing compounds. Cells were imaged and neurite length was analyzed by IncuCyte S3 Live Cell Analysis System every 4 hours.

Example 83

Aβ 1-42 induced cell death assay on human oligodendrocyte/neuron progenitors in 96-well plate. Cells were seeded on poly-L-ornithine and laminin coated plates at a density of 8,000 cells per well and maintained in expansion media until Day 3, then media was replaced with fresh spontaneous differentiation media containing testing compounds and IncuCyte Annexin V Red Reagent (1:200 dilution) (Essen BioScience Cat. No. 4641). After the pre-incubation period of 30 minutes at 37° C., 10.5 µM Aβ 1-42 (Bachem Product No. H-8146) was added directly in the pretreatment solution. Neurite length and total Annexin V positive area were analyzed by IncuCyte S3 Live Cell Analysis System every 2 hours.

Example 84

Bleomycin induced lung fibrosis in mice (therapeutic administration): Male C57B/L6 mice were housed for acclimation for no less than 7 days. After acclimation period, animals were randomly assigned to treatment groups. On day 0, mice were anesthetized with 5% isoflurane by inhalation for 10-15 mins and then suspended by their front teeth on a wire attached to a fixed animal operating plate. 50 µL of saline or bleomycin solution was administered via intratracheal instillation. Mice in treatment groups were intratracheally instilled with bleomycin hydrochloride (BLM) 2.0 U/kg (mg/kg) in sterile saline. On day 7 following bleomycin administration, half of the animals in vehicle group were sacrificed to establish a baseline for the level of fibrosis at the treatment initiation. Mice in normal control group received saline by p.o. once daily from Day 7 to Day 20. Treatment group mice received the compound dosed orally once daily from Day 7 to Day 20. On Day 20, 2-3 hours posted the last dose, all mice were sacrificed. Lungs were gently lavaged via the tracheal cannula with 0.8 mL of PBS containing 1% BSA and 0.6 mM EDTA. After the lavage, lung tissues were collected from each animal. The lung tissues were divided into 3 parts: the large lobe of right part was fixed with 10% neutral formalin for paraffin embedding and histopathology. The remained lobes of right parts were snap-frozen and protein lysates were prepared for target engagement analysis.

Example 85

Bleomycin induced lung fibrosis in mice (Phrophylactic administration): Male C57B/L6 mice were ear tagged and weighed prior to the start of the study. Treatment group animals were treated with the compound on day −1 pre-bleomycin and all subsequent days post-bleomycin administration. On day 0, animals in disease groups received 1.5 U/kg dose of bleomycin via oropharyngeal route. The non-bleomycin control group received sterile saline. Animals were closely monitored daily till the end of the study. On day 21 following bleomycin administration, all animals were euthanized and blood, lung, and bronchoalveolar lavage (BAL) fluid were collected. Blood samples were used for plasma preparation; total leukocytes were counted in BAL fluid; and lungs were fixed in 10% neutral buffered formalin for histopathological analysis.

Example 86

Histamine-induced vascular permeability model in mice: 7-8 weeks old Balb/c female mice were acclimated at least 3 days, and randomly assigned to groups. Animals were injected i.v. with 1% Evans Blue at a dose 100 µl/mouse. 10 minutes later animals in disease groups were given 1 µg of histamine in 20 µl PBS intradermally on the back and sacrificed 20 minutes after administration. 20 µL PBS were injected intradermal into the animal back in sham control. Vehicle and test articles were dosed via oral gavage accordingly. Positive control salbutamol was administered 15 minutes before Evans blue. 20 minutes post challenge with histamine, animals were euthanized. The skin was then inverted, the lesion diameters were measured. The area of the lesion was calculated and expressed in square millimeters. Following diameter measurements, Evan's Blue dye was extracted from the skin tissue and the optical density was measured. Data are calculated against a spiked in Evan's Blue standard curve.

Example 87

ROCK inhibitors potently inhibited ROCK kinase activity in vitro and in cells. Compounds of the invention inhibited ROCKs in cells as measured by A7R5 in-cell Elisa assay. A7R5 cells were treated with 9 points 2 fold serial dilution of compounds and ppMlc (T18/S19) levels were determined in order to calculate the cellular IC50s of the compounds. Results are provided in Table 1, below.

TABLE 1

| Compound | ppMlc IC50 (nM) |
| --- | --- |
| Example 2 | 86 |
| Example 8 | 517 |

Table 2, below, provides the in vitro and cellular ROCK inhibition for compounds of the invention. Compounds activities were measured by Z'-lyte kinase kit (ThermoFisher Scientific). The percent inhibition rate was calculated by normalizing the kinase activity value obtained with 1 µM compound treatment against DMSO control value. IC50s were calculated using the GraphPad Prism software with kinase activities data that were collected from 9 points serial dilution of compounds treatment. The ROCK inhibition in A7R5 cells and NIH3T3 (Acta2-Luc) cells was performed as described above.

TABLE 2

| Ex. # | ROCK2 % inh (0.5 µM) | ROCK2 IC50 (nM) | ROCK1 % inh (0.5 µM) | ROCK1 IC50 (nM) | pMLC IC50 (nM) A7R5 | NIH3T3, Acta2-luc, IC50 (nM) |
| --- | --- | --- | --- | --- | --- | --- |
| 8 | | 3 | | 12 | 517 | |
| 4 | | 3 | | | 108 | 110 |
| 2 | | 4 | | 17 | 120 | 352 |
| 3 | | 12 | | | 222 | 157 |
| 9 | | 15.4 | | | 355 | |
| 10 | | 21 | | | 255 | 1277 |
| 11 | | 4 | | | 69 | 106 |
| 12 | | 30 | | | 458 | 735 |
| 13 | | 6.3 | | | 425 | 1568 |
| 14 | | 6.8 | | | 353 | 496 |
| 15 | | 24 | | | 655 | 1049 |
| 16 | | 3.5 | | | 292 | 376 |
| 17 | 98% @ 0.5 µM | 6.3 | 99% @ 0.5 µM | | 60 | 108 |
| 18 | 89% @ 0.5 µM | 10 | 92% @ 0.5 µM | | 504 | 464 |
| 19 | 90% @ 0.5 µM | 4.8 | 96% @ 0.5 µM | | 355 | 190 |
| 20 | 94% @ 0.5 µM | 1.7 | 98% @ 0.5 µM | | 263 | 157 |
| 21 | | 3.1 | | | 47 | 66 |
| 22 | | 8.9 | | | 169 | 155 |
| 23 | 91% @ 0.5 µM | 21 | | | 435 | 252 |
| 24 | 97% @ 0.5 µM | 22 | | 88 | 334 | 1711 |
| 25 | | 94 | | | 692 | 663 |
| 26 | | 5.3 | | | 152 | 251 |
| 57 | | 10 | | | 74 | 175 |
| 59 | | 239 | | 759 | 4173; 5553 | >5,000 |
| 58 | | 12 | | 57 | 484 | 74 |
| 60 | | 98 | | 258 | 695 | 1413 |
| 61 | | 2.9 | | 7.7 | 35 | 48 |
| 27 | | 65 | | | 1676 | 699 |
| 28 | | 82 | | | 947 | 335 |
| 62 | | 1.8 | | 3 | 58 | 108 |
| 63 | | 22 | | 81 | 548 | 633 |
| 29 | | 14 | | | 647 | 146 |
| 30 | | 18 | | | 247 | >5000 |
| 31 | | 55 | | | 667 | 1229 |
| 32 | | 31 | | | >5000 | >5000 |
| 33 | | 29 | | 85 | 913 | 1476 |
| 64 | | 24 | | | 379 | 227 |
| 65 | | 1.2 | | | 65 | 51 |
| 66 | | 18 | | 56 | 332 | 396 |
| 34 | | 310 | | | >5000 | >5000 |
| 67 | | 1.9 | | | 269 | 296 |
| 68 | | 451 | | | >5000 | >5000 |
| 69 | | 400 | | | >5000 | >5000 |
| 35 | | 486 | | | >5000 | >5000 |
| 70 | | 7.7 | | | 134 | |
| 71 | | 3 | | | 57 | 301 |
| 36 | | 16 | | | 1,577 | 1546 |
| 37 | | 37 | | | 977 | 2314 |
| 38 | | 8.7 | | | 338 | 1622 |
| 39 | | 16 | | | 1,668 | >5,000 |
| 40 | | 45 | | | 632 | 826 |
| 41 | | 12 | | | 1,248 | >5,000 |
| 42 | | 6.5 | | | 359 | |
| 43 | | 47 | | | 1,491 | |
| 44 | | 42 | | | 2,021 | 2229 |
| 45 | | 53 | | | 1,358 | 1463 |
| 46 | | 107 | | | 1,877 | 1200 |
| 47 | | 30 | | | 321 | 465 |
| 48 | | 67 | | | 314 | 1013 |
| 49 | | >1000 | | | | |
| 74 | | >1000 | | | | |
| 50 | | 2.4 | | | 97 | 92 |
| 51 | | 8.1 | | | 54 | 101 |
| 52 | | 17 | | | 106 | 675 |
| 54 | | 68 | | | 1,516 | 2666 |
| 53 | | 31 | | | 759 | 1260 |
| 55 | | 17 | | | 506 | 601 |
| 56 | | 5.3 | | | 115 | 78 |
| 75 | | >1000 | | | | |
| 72 | | 46 | | | 382 | 984 |
| 73 | | 1.6 | | | 15 | 122 |
| 76 | | 950 | | | | |

Compounds of the present invention have an alkyl substituent (optionally substituted) on the 2-amino group (i.e., $R^1$ is alkyl, etc), which is associated with enhanced cellular ROCK activity relative to compounds having a primary amino group at this position, and particularly for lower alkyl amines at the 2-position (i.e., $R^1$ is lower alkyl).

Example 88

ROCK Inhibitors Penetrated Blood-Brain Barrier.
Brain and plasma concentrations of select ROCK inhibitors were evaluated in mouse by HPLC/MS/MS at 15 min and 2 hrs following 2.5 mg/kg IV drug administration. The results are provided in Table 3, below.

TABLE 3

| Compound | Dose Level | Route | Site | Mean Conc. at 0.25 hr (ng/mL) or (ng/g) | Mean Conc. at 2 hr (ng/mL) or (ng/g) | Mean Brain/Plasma Ratio at 0.25 hr | Mean Brain/Plasma Ratio at 2 hr |
|---|---|---|---|---|---|---|---|
| Example 2 | 2.5 | IV | Plasma | 268 | 25.7 | 2.01 | 2.99 |
|  |  |  | Brain | 541 | 76.6 |  |  |

ROCK inhibitors of the invention potently inhibited ROCK kinase activity in vitro and in cells.

As shown in FIG. 1a, compounds of the invention at lower than 20 nanomolar concentrations potently inhibited the activity of both isoforms of ROCK in vitro as measured by the Z'-Lyte kit (ThermoFisher Scientific). The percent inhibition rate was calculated by normalizing the kinase activity value obtained with compound treatment against DMSO control value and then applied to the equation, [DMSO−(compound/DMSO)]×100%. $IC_{50}$'s were calculated using the nonlinear regression curve fit function of the GraphPad Prism software with kinase activities data measured with 9 points 2-fold serial dilution of compounds treatment.

Figure 1B:
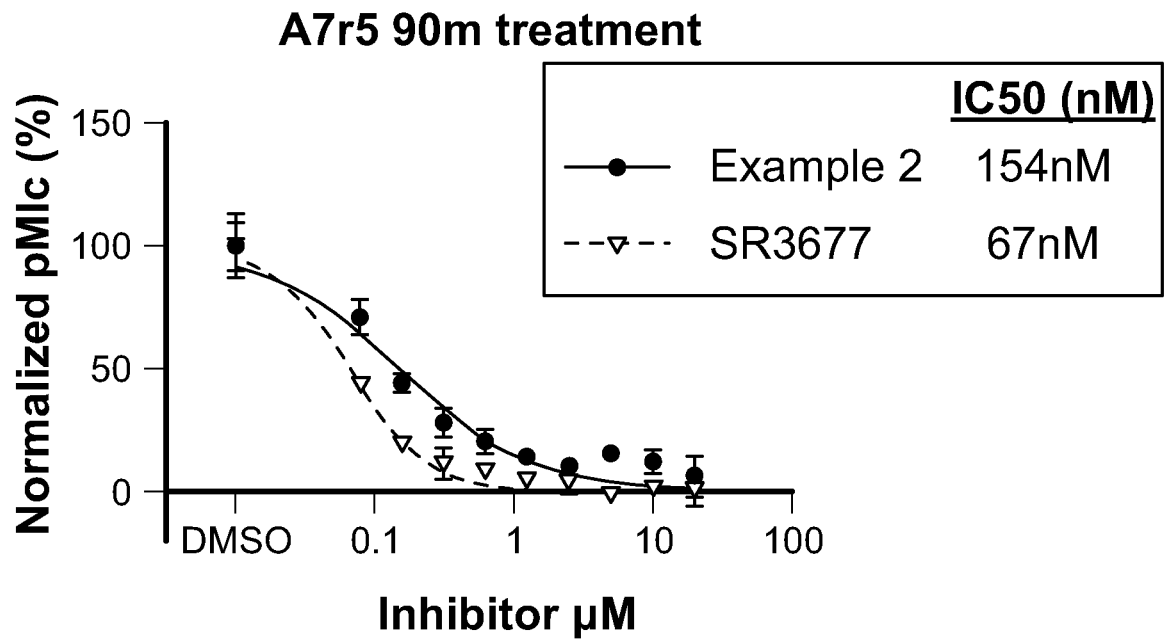
FIG. 1b. A7R5 in-cell ELISA assay. A7R5 cells were treated with 9 points 2 fold serial dilution of compounds and ppMlc (T18/S19) levels were determined to calculate cellular $IC_{50}$ values of the compounds. Representative compounds of the invention gave in cell $IC_{50}$'s under 200 nM.

An A7R5 in-cell ELISA assay was performed to determine ROCK inhibition of test articles. A7R5 cells were treated with 9 points 2-fold serial dilution of compounds and ppMlc (T18/S19) levels were determined to calculate cellular $IC_{50}$ values of the compounds. Compounds of the invention showed activities of $IC_{50}$'s under 200 nM. See FIG. 1b. A7R5 cells were treated with 9 points 2-fold serial dilution of compounds and ppMlc (T18/S19) levels were determined to calculate cellular $IC_{50}$ values of the compounds using the nonlinear regression curve fit function of the GraphPad Prism software.

Figure 1C:
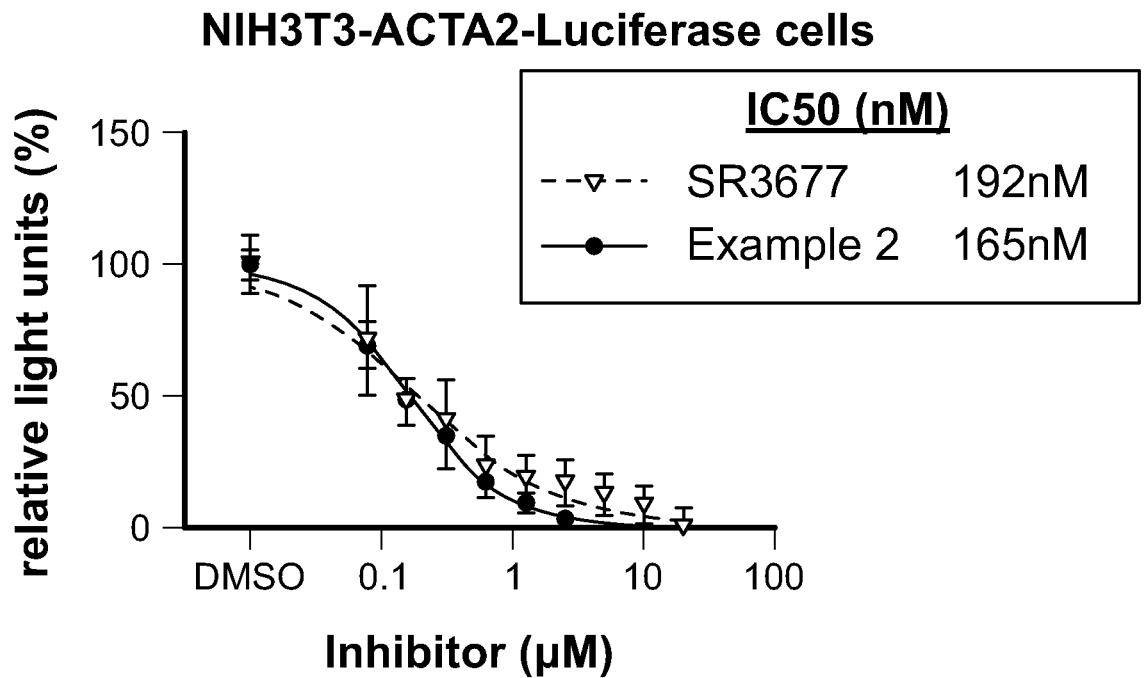
FIG. 1c. ROCK inhibitors can be effectively rank ordered by ACTA2-promoter-driven-luciferase reporter cell assay. NIH3T3 cells stably expressing ACTA2-promoter-drivenluciferase were plated in 96 well plates to confluence and treated with 9 points serial dilution of compounds in combination with TGFβ1 for 24 hr. Luciferase activities were measured and compound's $IC_{50}$s were calculated. Representative compounds of the invention showed $IC_{50}$s under 200 nM.

ROCK inhibitors can be effectively rank ordered by ACTA2-promoter-driven-luciferase reporter cell assay. NIH3T3 cells stably expressing ACTA2-promoter-driven-luciferase were applied to measure ROCK compounds functional $IC_{50}$'s in cells. Cells were plated in 96 well plates to confluence and treated with 9 points serial dilution of compounds in combination with TGFβ1 for 24 hr. Luciferase activities were measured and compound's $IC_{50}$'s were calculated using the nonlinear regression curve fit function of the GraphPad Prism software. Compounds of the invention gave in cell $IC_{50}$'s under 200 nM, see FIG. 1c.

Figure 1D:
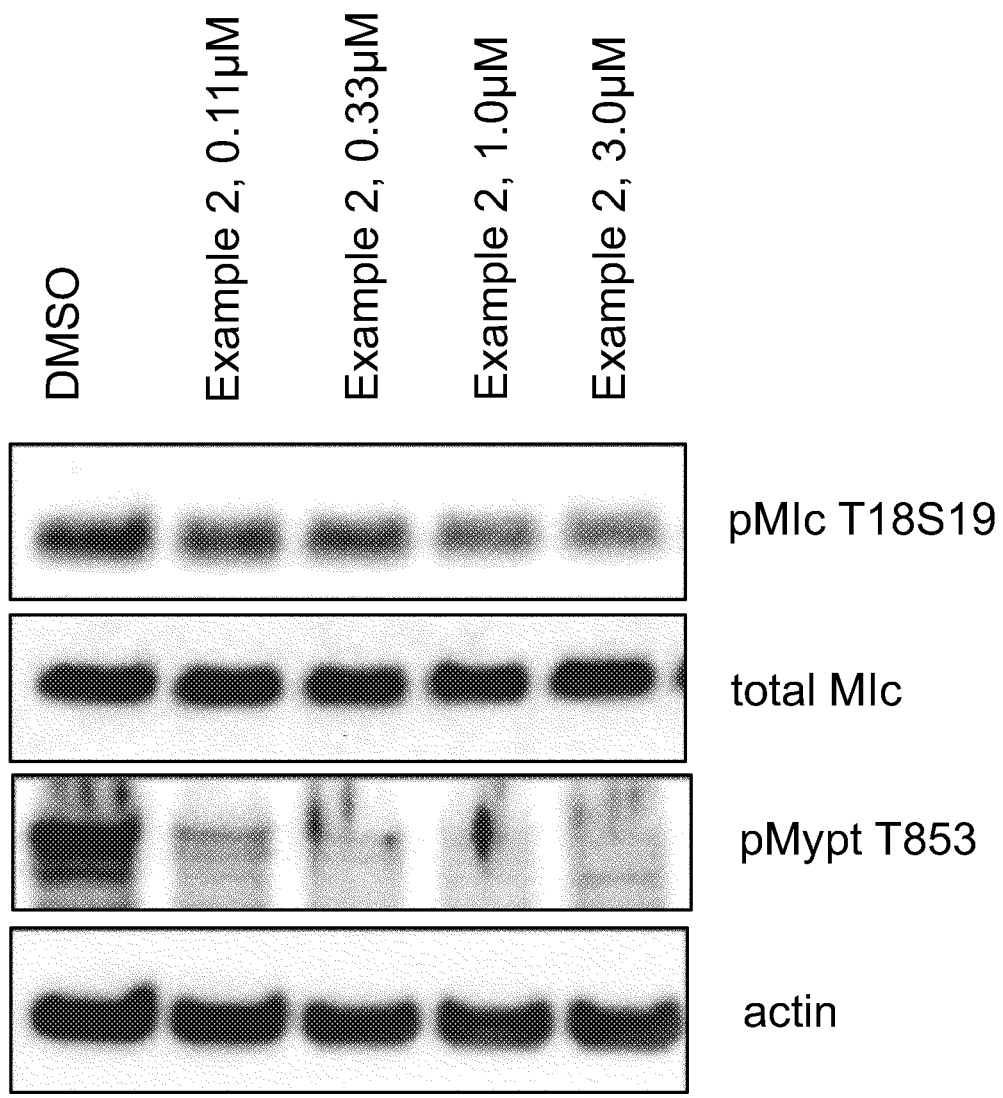
FIG. 1d. Western blot of SVEC4-10 cell lysates to visualize ppMlc (T18/S19) & pMYPT (T853) levels following treatment with the compound of Example 2 for 120 min. SVEC4-10 cells were treated with the compound and phosphorylated proteins were visualized by western blotting. Representative compounds efficiently blocked ROCK targets MLC and MYPT1 phosphorylation at 110 nM.

Compounds ROCK activities were tested in additional cell types. Svec 4-10 mouse endothelial cells were treated with the compound of Example 2 for 120 min and ppMlc (T18/S19) and pMypt (T853) levels were visualized by western blotting. Example 2 at 110 nM efficiently blocked phosphorylation of ROCK targets MLC and MYPT1, see FIG. 1d.

Example 89

ROCK Inhibitors Promote Neurite Outgrowth and Neuronal Differentiation

Neuronal development requires highly coordinated regulation of the cytoskeleton. The activation of RhoA/ROCK pathway causes cytoskeleton changes such as increasing retrograde actin flow and decreasing actin depolymerization and eventually leads to growth cone collapse which in turn suppress neurite growth and extension. Here we show that ROCK inhibitors facility neurons sprouting and neurite outgrowth in a dose dependent manner. FIG. 2 a,b demonstrates that compounds of example 2 and example 17 significantly increase neurite length at various concentrations in human oligodendrocyte/neuron progenitors culture. Example 2 and Example 17 also facility neuronal differentiation and maturation, see FIG. 2 c,d.

Figure 2A:
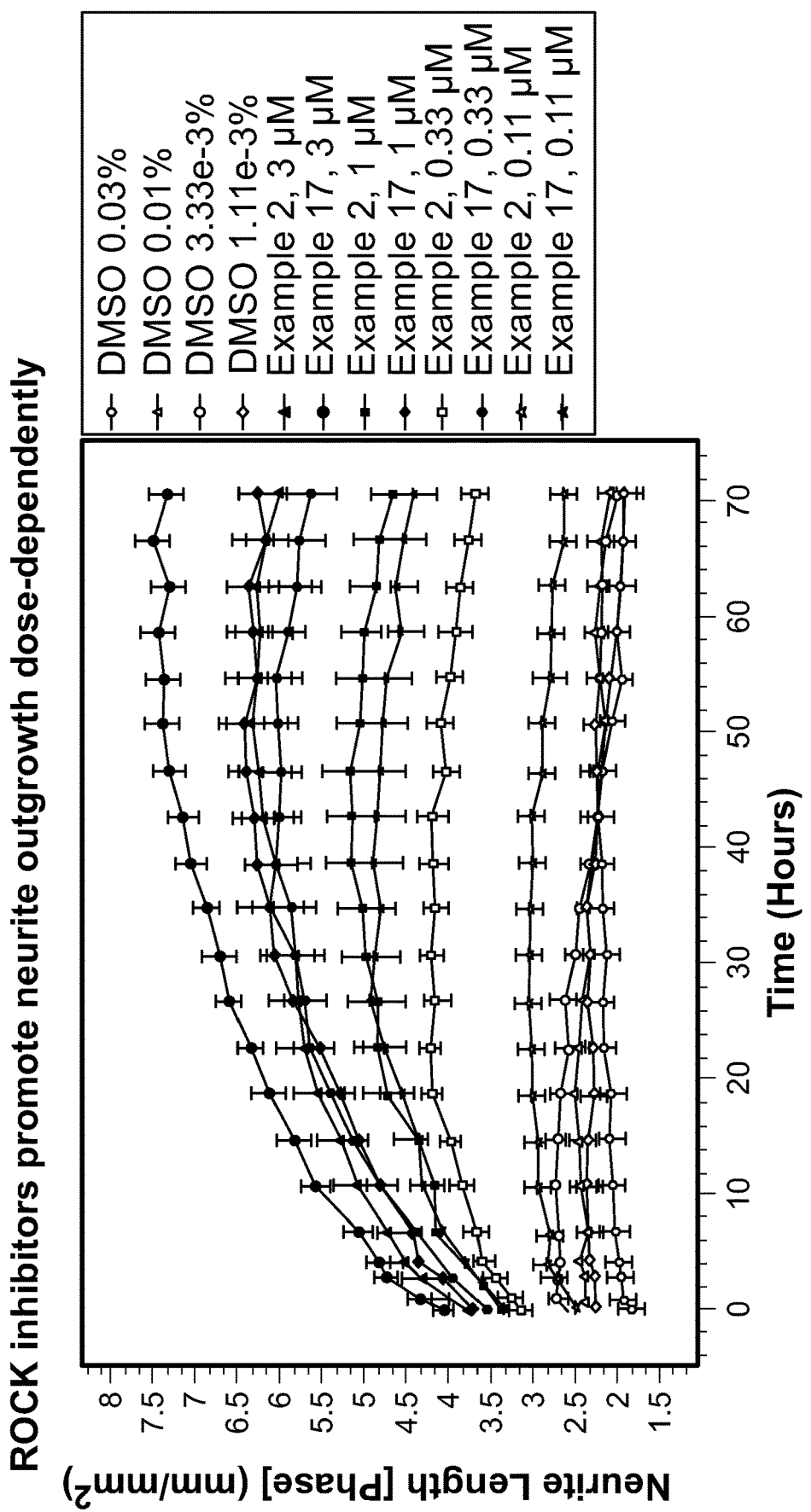
FIGS. 2a and b, ROCK inhibitors promote neurite outgrowth in a dose-dependent manner in human oligodendrocyte/neuron progenitor cells in culture. Human oligodendrocyte/neuron progenitor cells were cultured in vitro with or without ROCK inhibitor for 3 days.
Figure 2B:
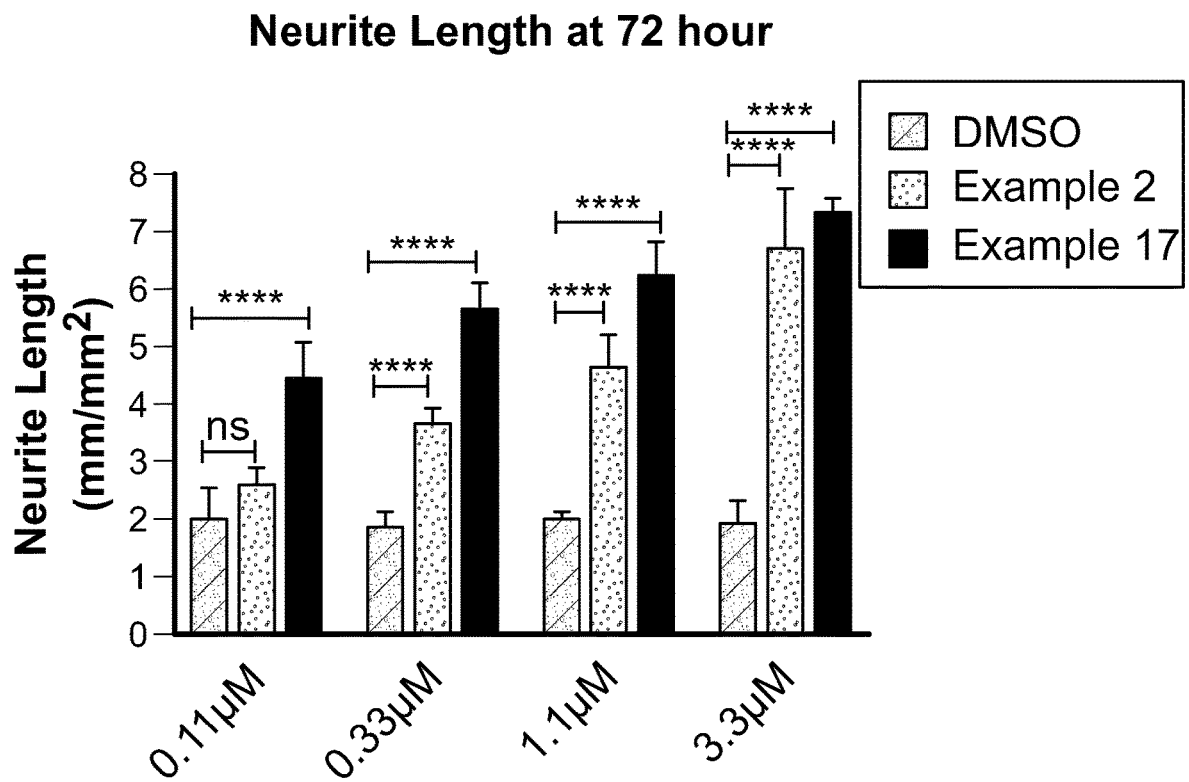
FIGS. 2c and d. ROCK inhibitors enhance neuronal cells differentiation and maturation. Human oligodendrocyte/neuron progenitor cells were cultured for 14 days. ROCK inhibitors significantly facilitated mature neuronal cell marker Beta III tubulin expression and improved neurite outgrowth.
FIG. 2d, quantifications of neurite length.
FIGS. 2e, f and g. ROCK inhibitors block the inhibitory effect of Chondroitin Sulfate Proteoglycan (CSPG) on neurite outgrowth. Human oligodendrocyte/neuron progenitor cells were cultured on 0.3 mg/ml CSPG coated plates for 3 days. Neurite length were quantified by IncuCyte NeuroTrack Software Module. The statistical analysis for 72 hour time point was done by ANOVA.
FIG. 2f, neurite length time course.
FIG. 2g, quantifications of neurite length at 72 hrs treatment.
Figure 2C:
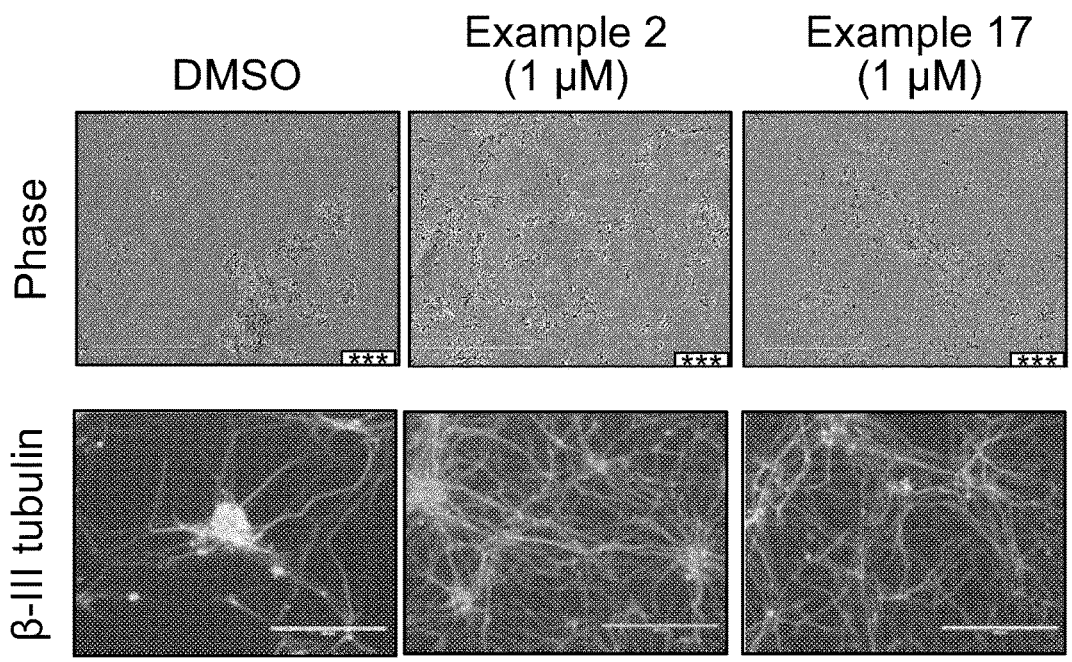
Figure 2D:
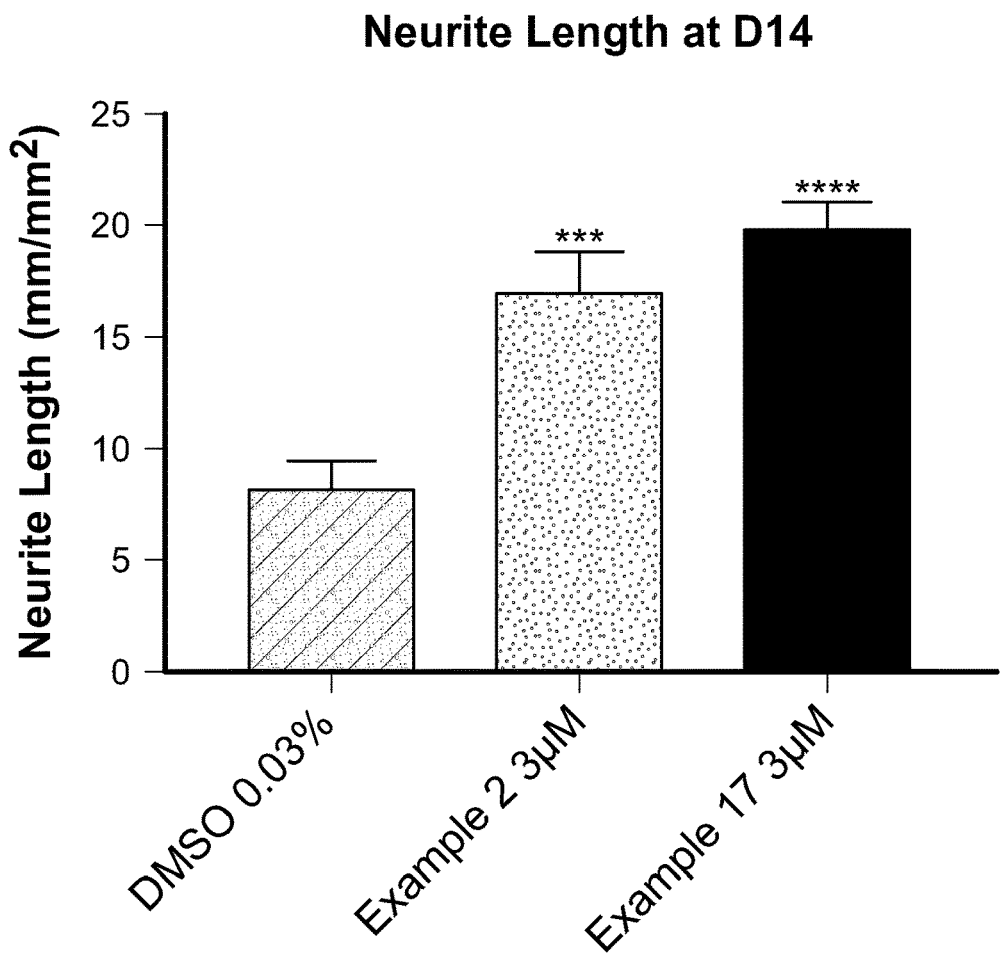
Figure 2E:
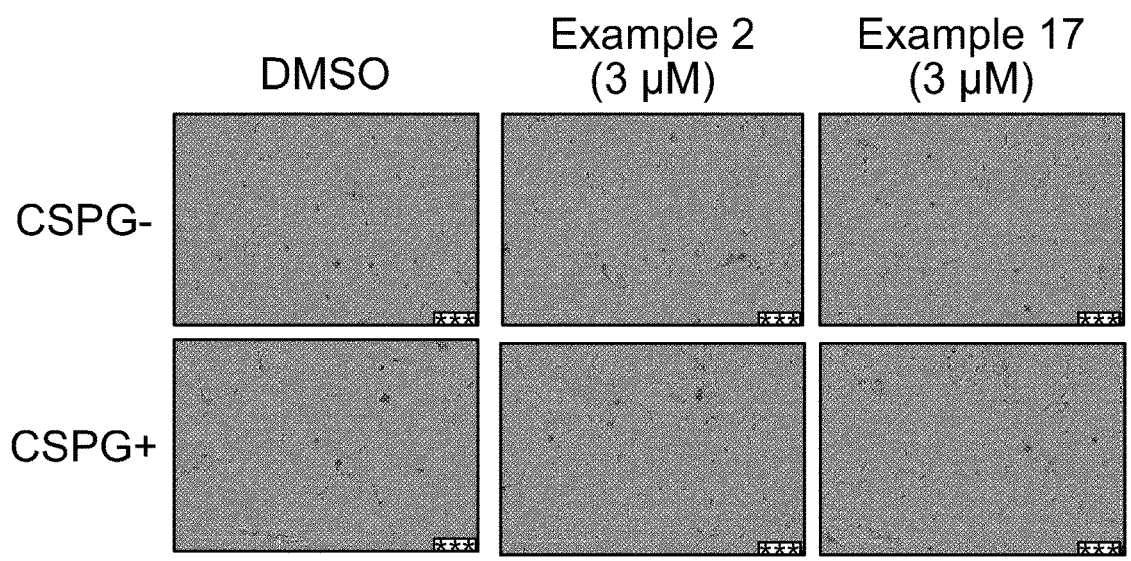
Figure 2F:
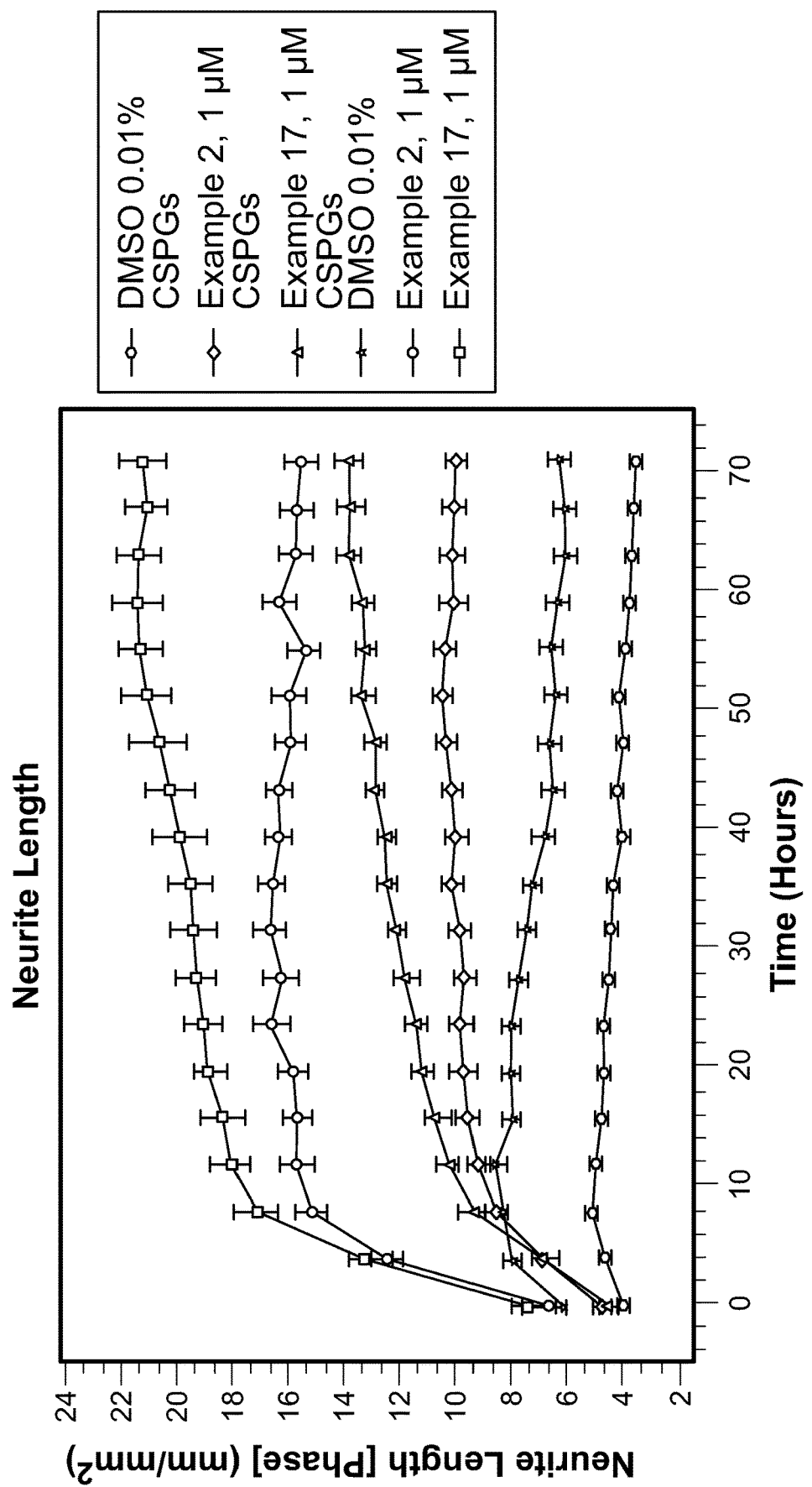
Figure 2G:
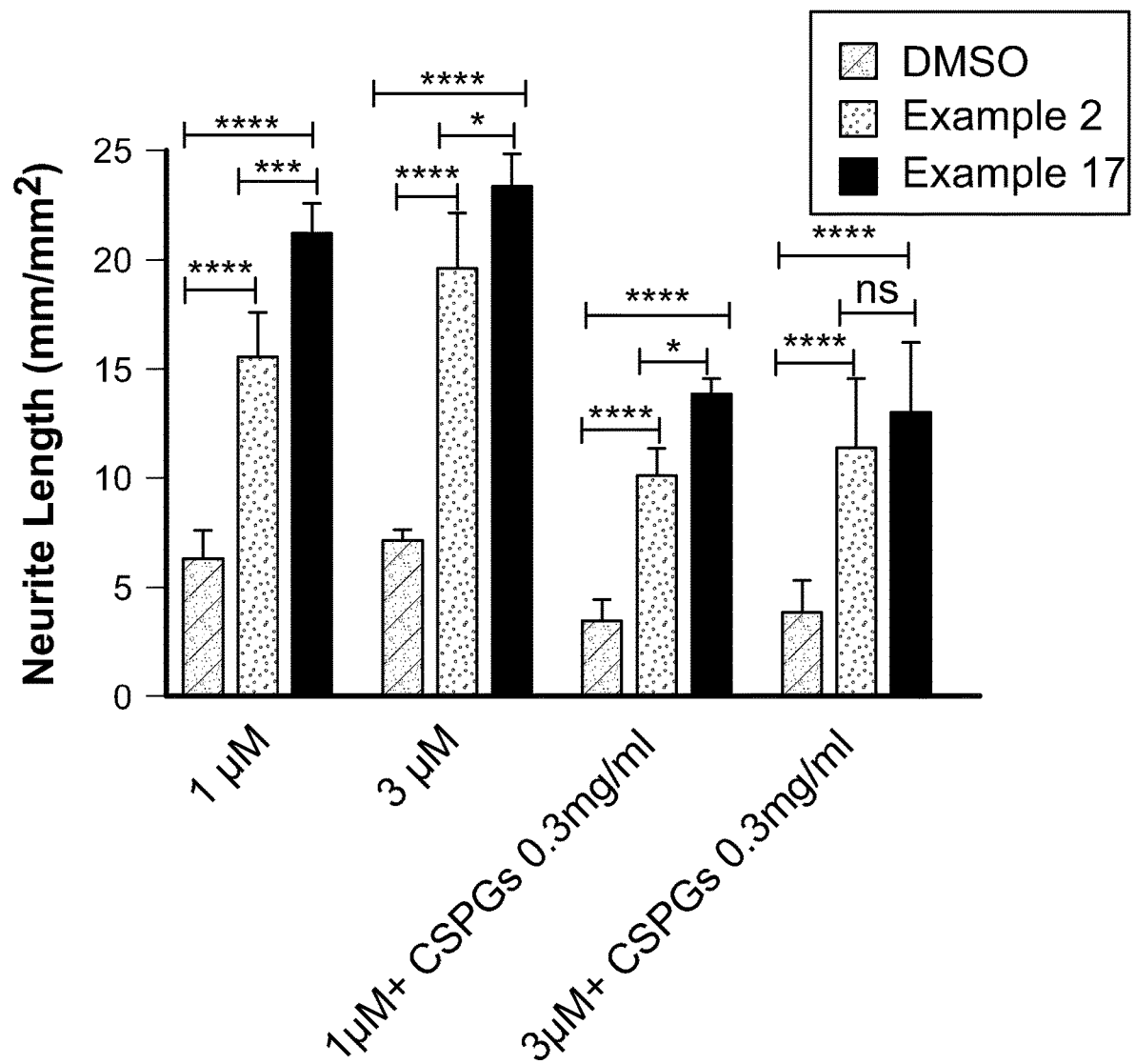

ROCK inhibitors block the inhibitory effect of Chondroitin Sulfate Proteoglycan (CSPG) on neurite outgrowth. The adult mammalian CNS neurons don't spontaneously regenerate after traumatic injury or neurodegeneration. This lack of regeneration has been attributed to both low intrinsic regeneration capacity of adult neurons and inhibitory tissue environment. Main obstacles in the hospitable environment are chondroitin sulfate proteoglycans (CSPGs) secreted by reactive astrocytes and myelin associated inhibitors produced by oligodendrocytes. These glia cell derived growth inhibiting molecules are upregulated after neuronal injury, converge downstream on the RhoA/ROCK signaling pathway and block neuroregeneration. Promoting regeneration needs the inactivation of growth inhibitory factors from tissue environment. Here we show that by blocking the Rho/ROCK pathway that the glia growth inhibiting factor signal through, the inhibitory effect of CSPG on neurite extension was reversed. FIG. 2e shows representative pictures at day 3. As shown in FIGS. 2f and 2g, both 1 μM and 3 μM example 2 and example 17 significantly counteract 0.3 mg/ml CSPG mediated neurite outgrowth arrest in human oligodendrocyte/neuron progenitors. The statistical analysis for 72 hour time point was done by ANOVA.

Example 90

ROCK Inhibitors Protect Neuronal Cells from Aβ1-42 Induced Cell Death.

Figure 3A:
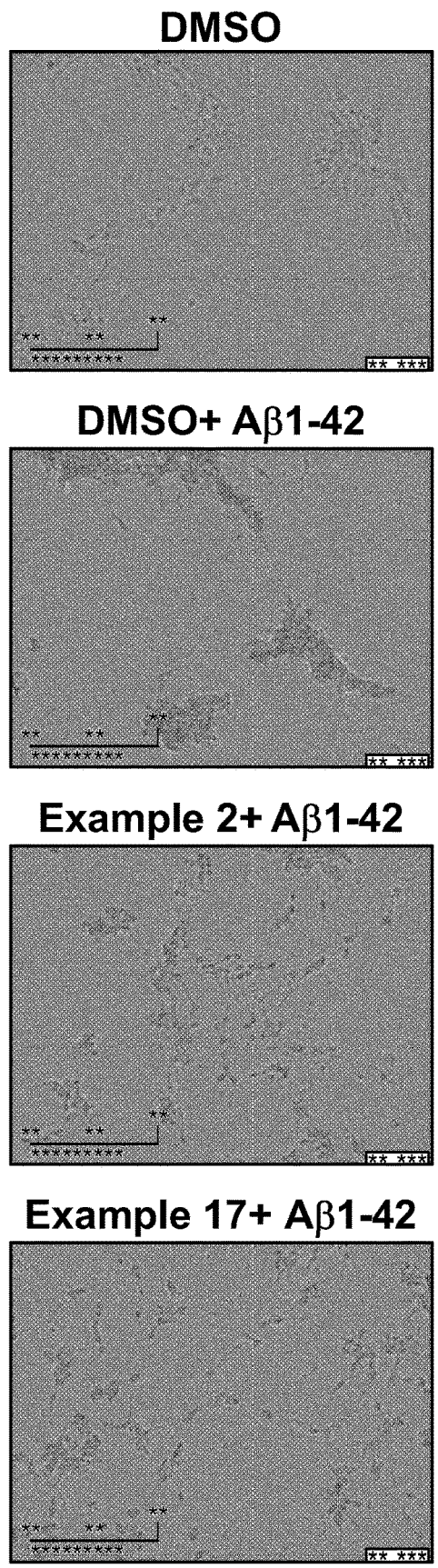
FIGS. 3a, b, c, d and e. ROCK inhibitors protect neuronal cells from Aβ1-42 induced cell death. Human oligodendrocyte/neuron progenitor cells were pre-incubated with ROCK inhibitors for 30 minutes before exposing to 10.5 μM Aβ1-42. IncuCyte Annexin V Red Reagent was added to culture media to label cell apoptosis. Neurite length and total Annexin V positive area was analyzed by IncuCyte S3 Software.
Figure 3B:
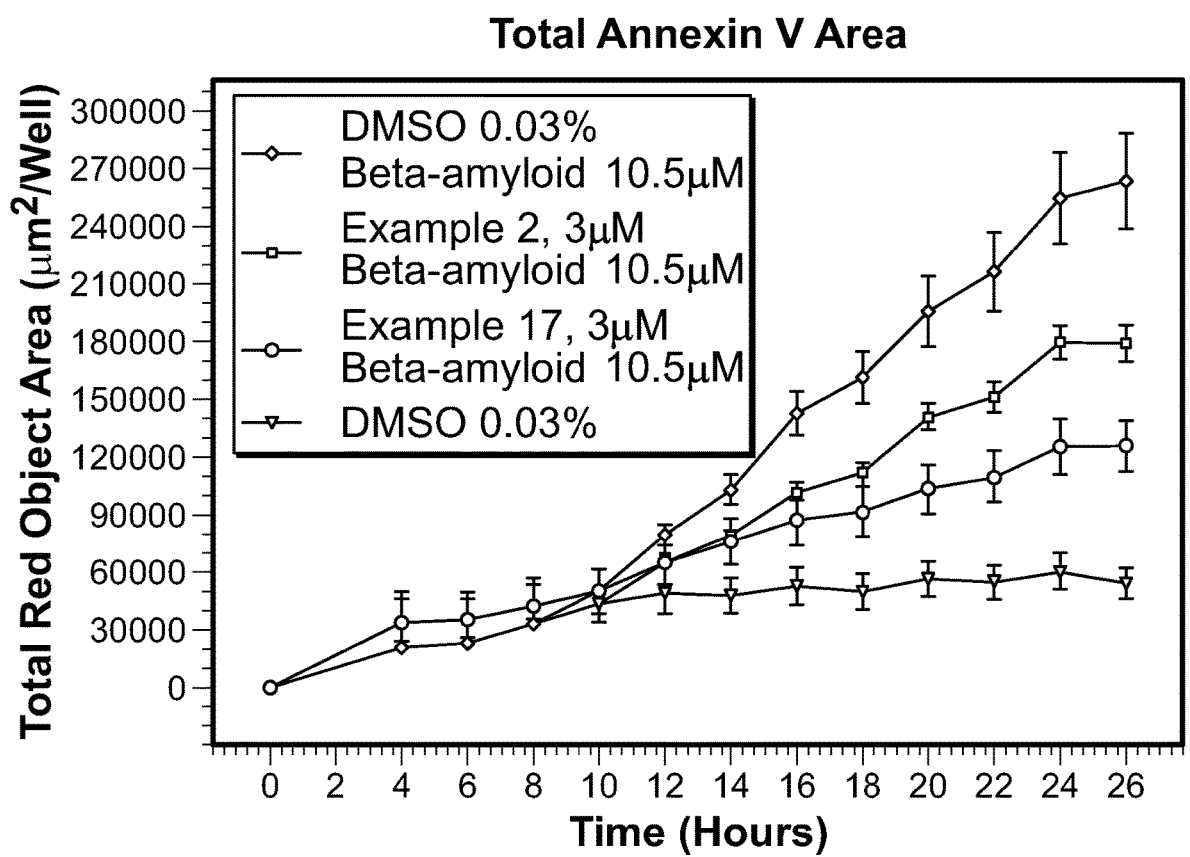
FIG. 3b. total annexin v positive area time course.
Figure 3C:
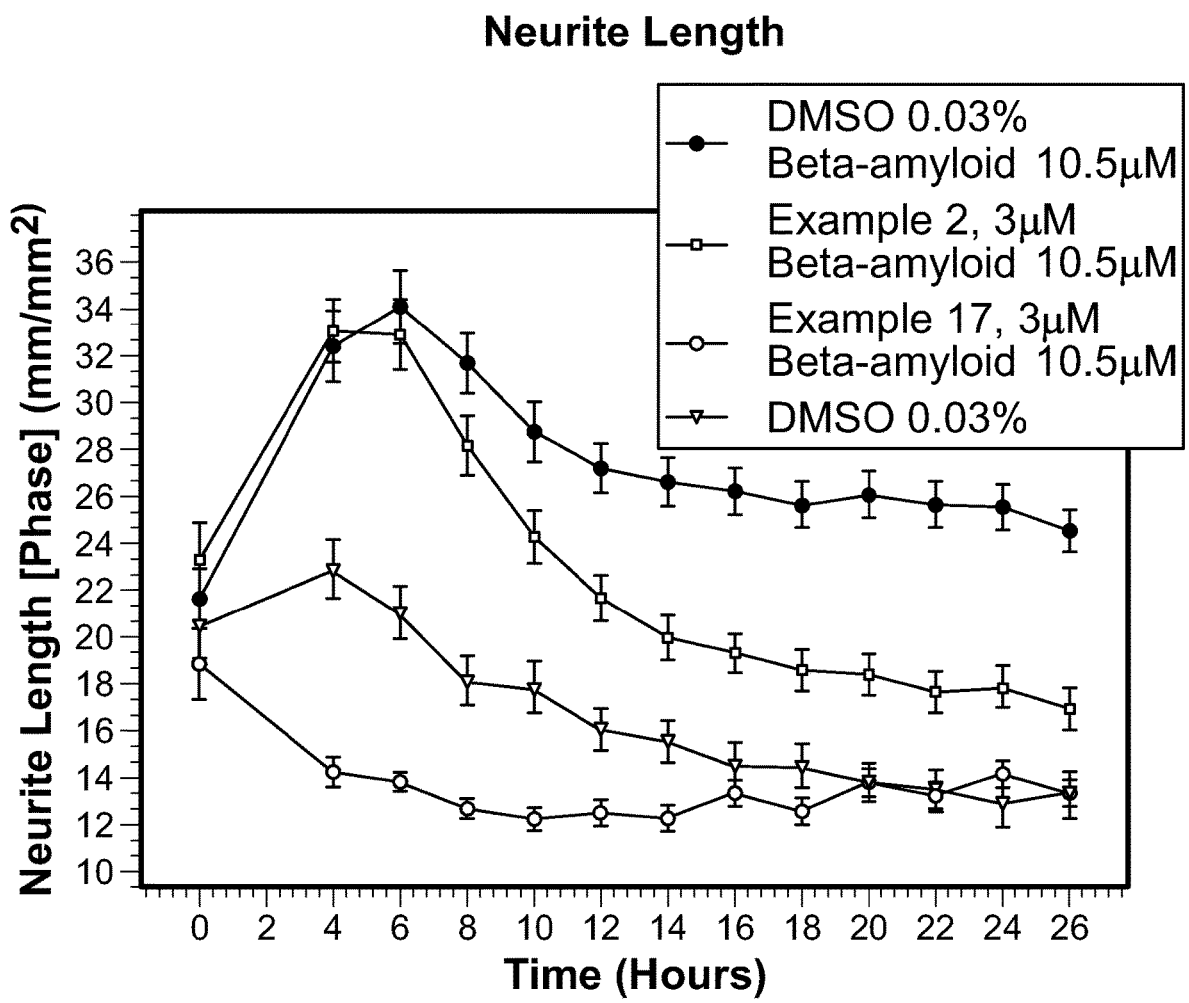
FIG. 3c, neurite length time course.
Figure 3D:
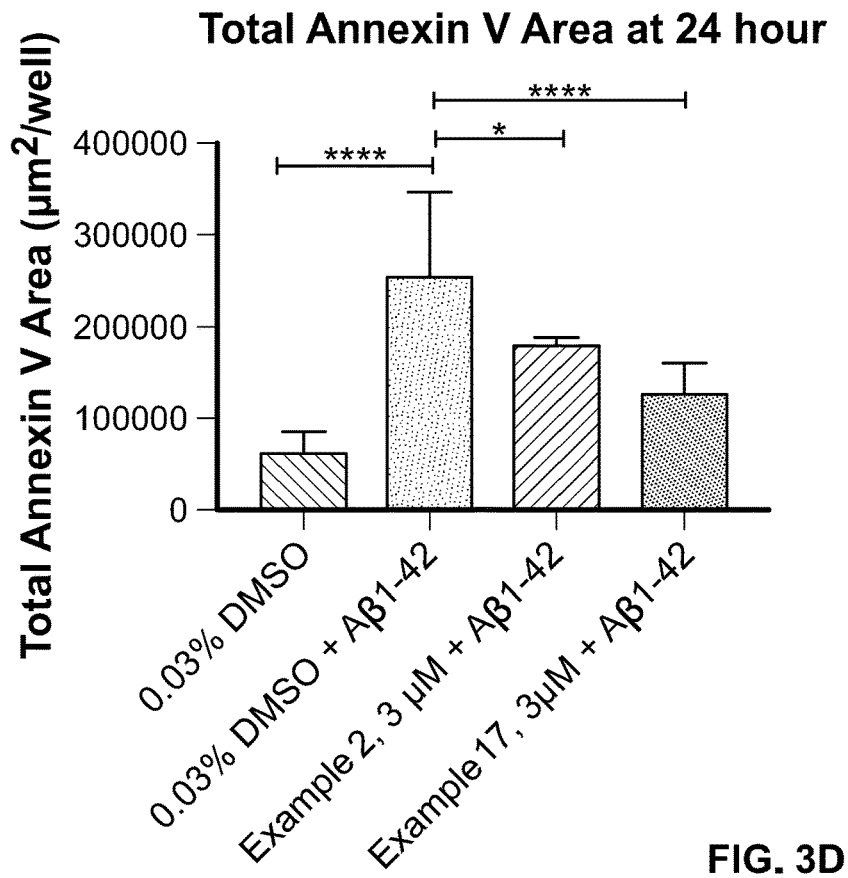
FIG. 3d, total annexin v positive area dose response.
Figure 3E:
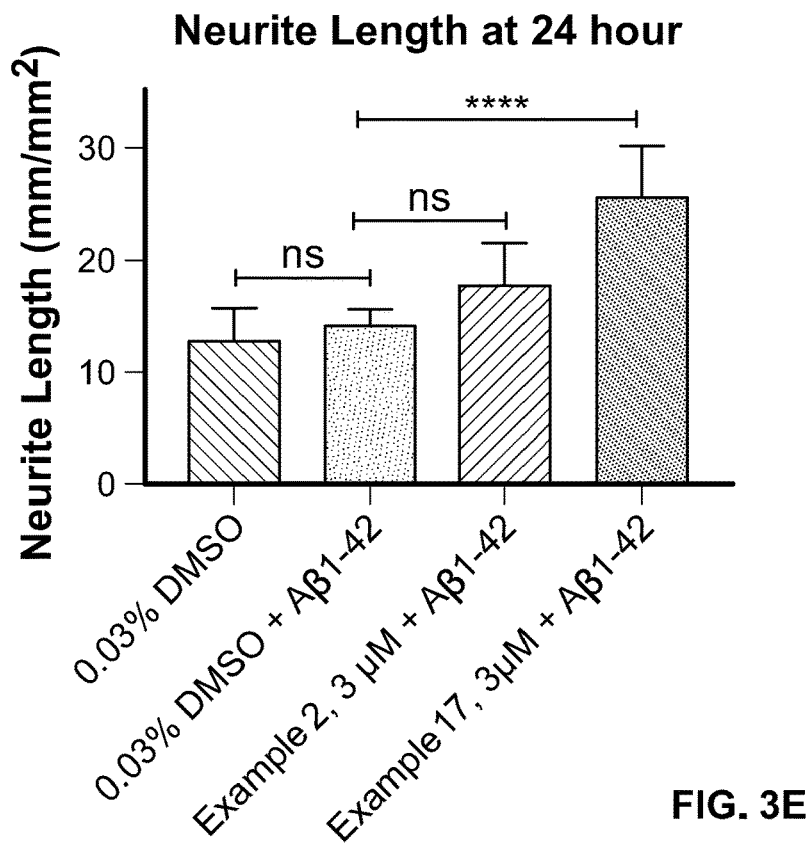
FIG. 3e, neurite length dose response quantifications.

In addition to promoting neuroregeneration, ROCK inhibitors have been reported to exert neuroprotective effects and prolong neuronal survival. Here we test the neuroprotective effect of ROCK inhibitors against Aβ1-42. Human oligodendrocyte/neuron progenitor cells were pre-incubated with ROCK inhibitors for 30 minutes before exposing to 10.5 μM Aβ1-42. IncuCyte Annexin V Red Reagent was added to culture media to label cell apoptosis. Pictures were taken by IncuCyte S3 and total Annexin V positive area was analyzed by IncuCyte S3 base software. Representative pictures were shown in FIG. 3a. Neurite length was quantified by IncuCyte NeuroTrack Software Module, see FIGS. 3b and 3c. FIGS. 3e and 3f show the statistical analysis for 24 hour time point of Annexin V area and neurite length, which shows that 3 μM example 2 and example 17 significantly protect Aβ1-42 induced cell death, and 3 μM Example 17 promoted neurite outgrowth in the presence of Aβ1-42.

Example 91

ROCK Inhibitors of the Invention Dampened Pro-Fibrotic Gene Expressions

Figure 4A:
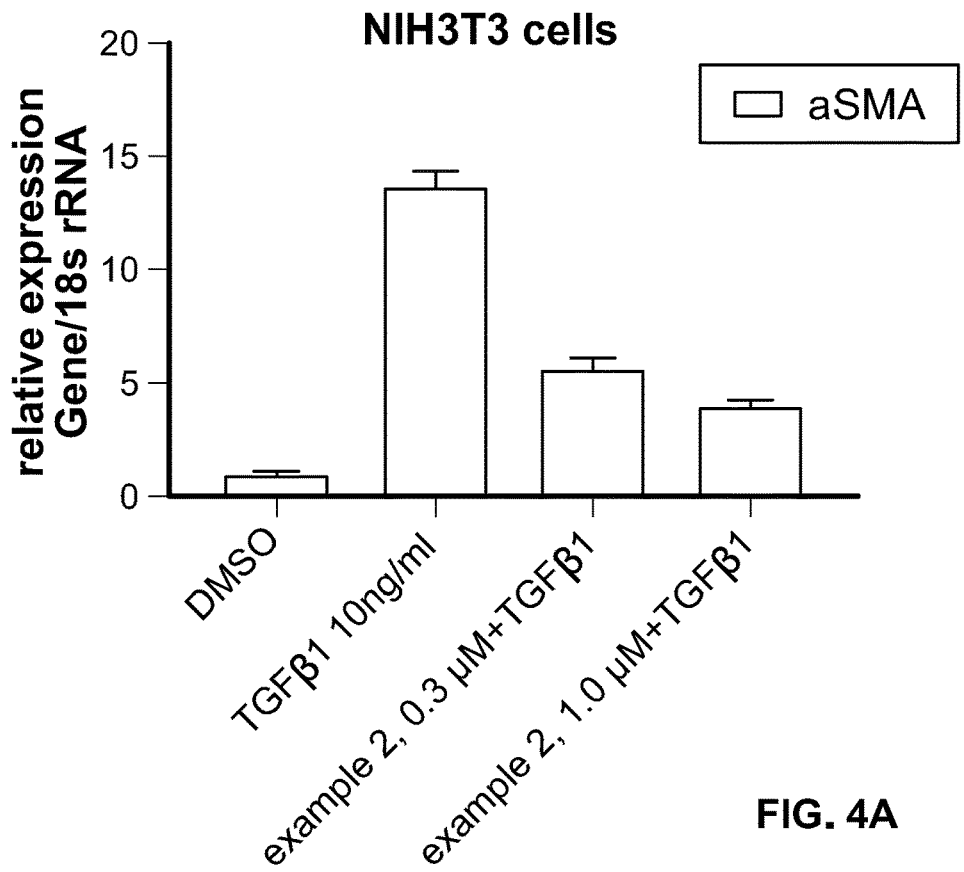
FIG. 4a, αSMA.

Expression of α-smooth-muscle-actin (αSMA, or Acta2) by fibroblasts is a key marker indicating the transdifferentiation of fibroblasts to more pro-fibrotic myofibroblasts exemplified by increased expression of fibrogenic factors. Such pro-fibrotic factors, including TGFβ signaling, lead to expression of αSMA and contribute to myofibroblast differentiation, proliferation and sustained survival. As shown in FIG. 4a, TGFβ1 induced αSMA expression was decreased significantly by ROCK inhibitor. NIH3T3 cells were treated with TGFβ1 in combination with ROCK inhibitors for 24 hours and mRNA expressions were quantified by Taqman qPCR.

Figure 4B:
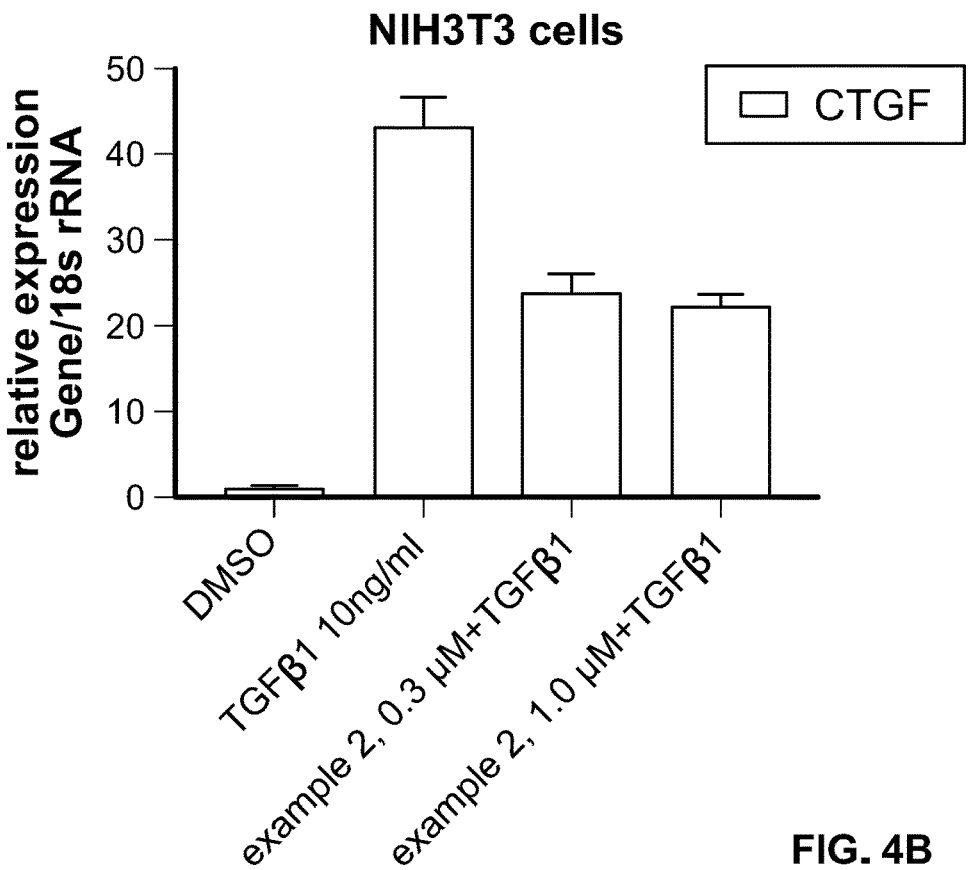
FIG. 4b, CTGF, FIG. 4c, CCN1 mRNA.
Figure 4C:
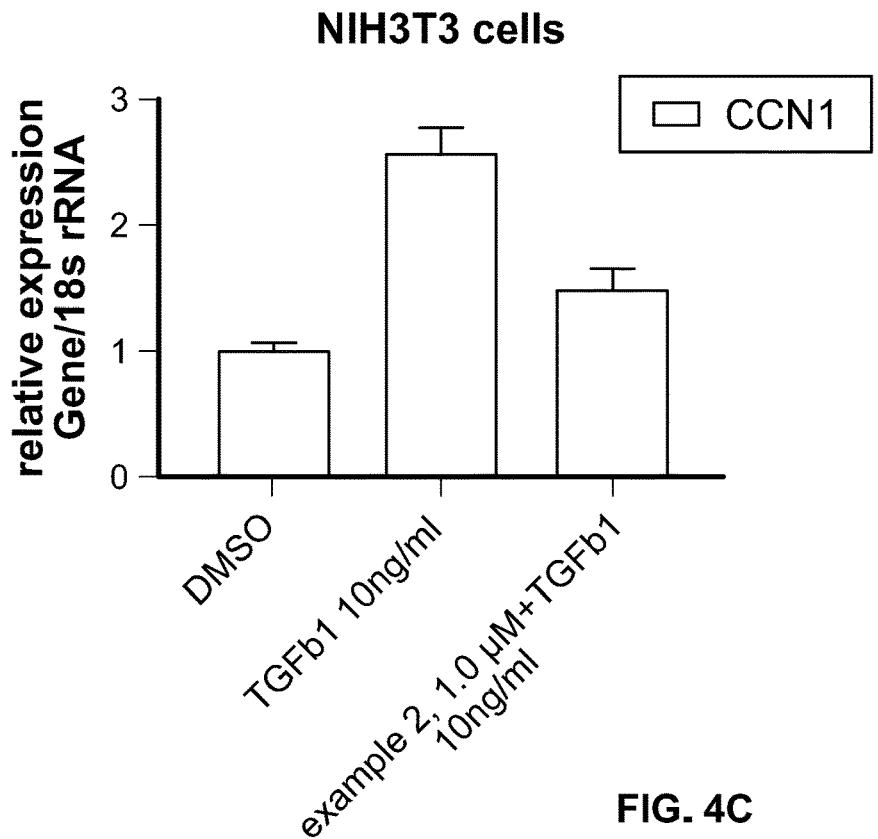
FIG. 4. ROCK inhibitor decreased TGFβ1 induced fibrotic gene expressions in NIH3T3 mouse fibroblast cell line. NIH3T3 cells were treated for 24 hours with TGFβ1 with or without the presence of TOCK inhibitor and mRNA expressions were quantified by Taqman qPCR.
FIG. 4d., ROCK inhibitor inhibited TGFβ1 induced CCN1 secretion. CCD18Lu human lung fibroblasts were treated with ROCK inhibitor and stimulated with TGFβ1 for 40 hours before secreted CCN1 level was measured with ELISA method.
Figure 4D:
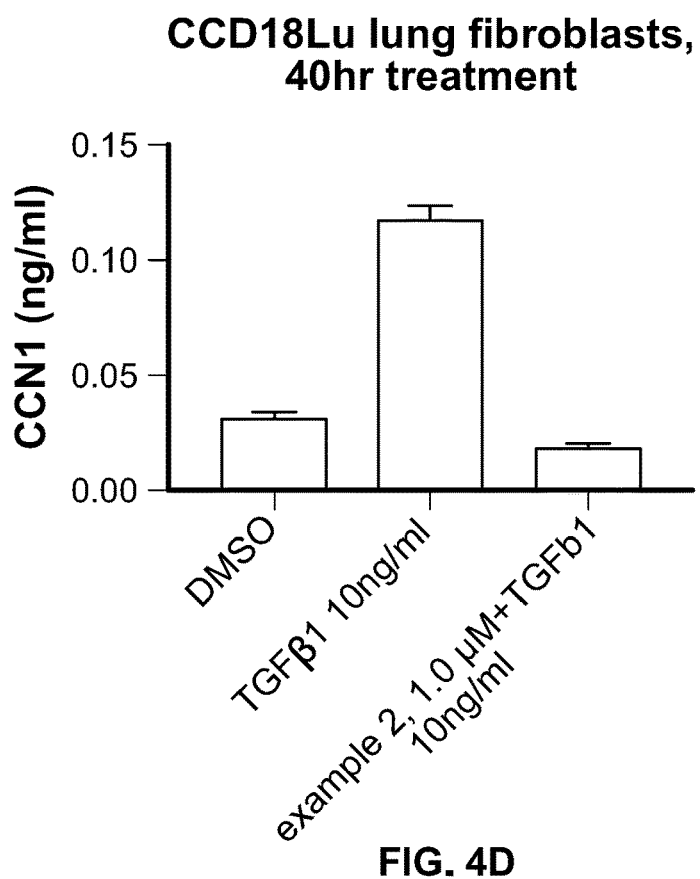

In addition to expression of αSMA, myofibroblasts isolated from IPF patients' lung show senescence characteristics. They are resistant to apoptosis and are highly active in metabolism, persistently produce large amounts of ECM proteins to drive fibrosis development. CCN1 (or CYR61) and CTGF belong to these classes of proteins. Treatment of human lung fibroblast with ROCK inhibitor under TGFβ induction, strongly inhibited expression of CTGF and CCN1, see FIGS. 4b & C. Secreted CCN1 proteins, demonstrated by cell culture medium ELISA assay as shown in FIG. 4d. was also decreased by ROCK inhibition. CCD18Lu fibroblasts cells were treated with ROCK inhibitor in combination with TGFβ for 40 hrs. CCN1 contents were measured using human CCN1 ELISA kit from R&D Systems. These results suggest that ROCK inhibitors could dampen pro-survival, pro-senescent signals of myofibroblasts under fibrotic conditions.

Example 92

Figure 5A:
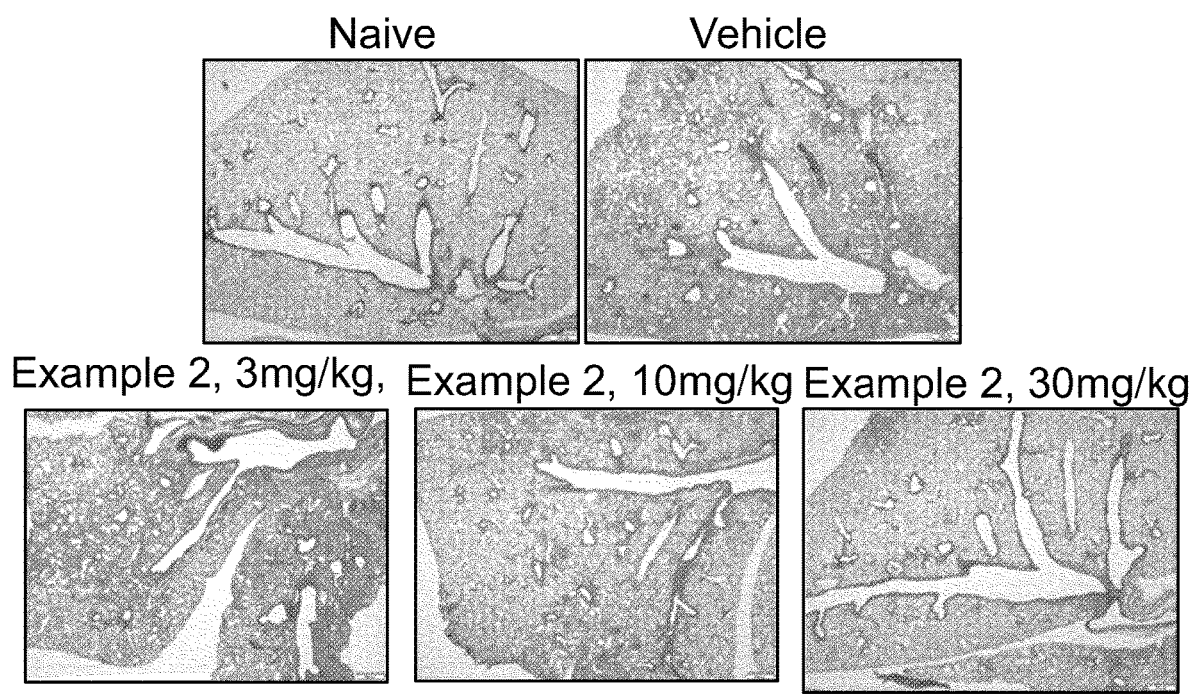
FIG. 5a. ROCK inhibitor is active in a mouse model of pulmonary fibrosis. Representative images of lung sections stained with Masson's trichrome to visualized fibrosis in the lungs of mice following 21-day treatment with ROCK inhibitor in the bleomycin-induced lung injury model.

ROCK Inhibitor is Effective in Lowering Multiple Fibrotic Indices in the Bleomycin Induced Pulmonary Fibrosis Model in Mice Based on the strong anti-fibrotic cellular activity of ROCK inhibitors of this invention, the ability of such inhibitors to attenuate fibrosis in the in vivo setting was assessed in several mouse models of fibrotic diseases including the bleomycin induced pulmonary fibrosis. Following the intratracheal installation of bleomycin mice were orally administered ROCK inhibitor at dose of either 3 mg/kg, 10 mg/kg or 30 mg/kg. Control animal received vehicle only in the same once daily administration schedule. Following 20 days of treatment the animals were sacrificed and lungs were removed, weighted and fixed for histopathological evaluation. FIG. 5a shows representative images of Masson's Trichrome stained lung sections at 10× objective from each treatment group. While in the treatment groups fibrotic mass formation (arrowhead), thickened alveolar septae and knot-like formation (arrow) was still present all were less severe compared to bleomycin induced controls. (B=bronchiole). Overall ROCK inhibitor improved lung architecture and collagen deposition in a dose dependent manner in this model. With mice receiving doses ≥10 mg/kg showing clear and statistically significant improvements.

Figure 5B:
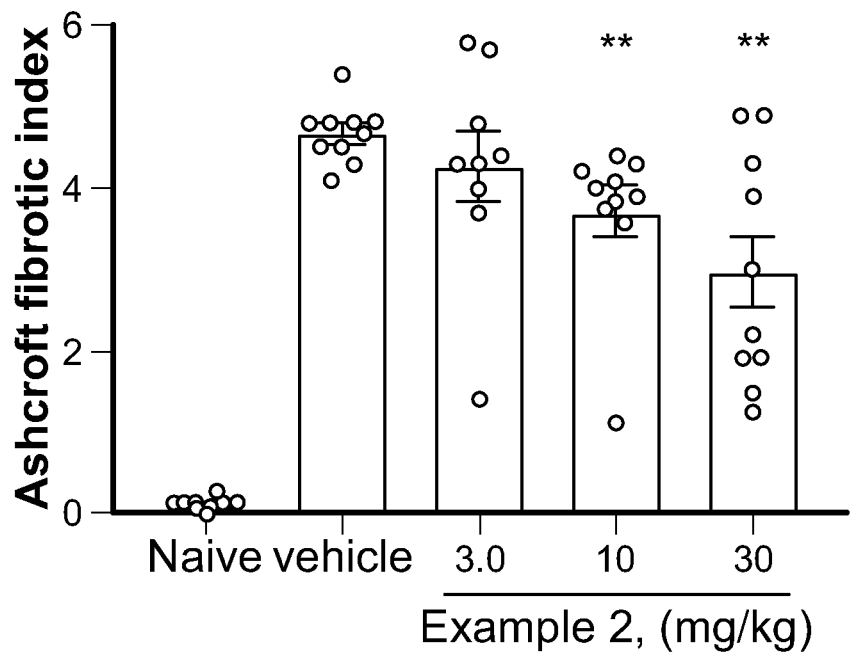
FIG. 5b. Quantitation of the positive activity of ROCK inhibitor in an in vivo model of pulmonary fibrosis. Ashcroft fibrotic indices, α-smooth muscle actin (αSMA) percentage positive area and total leukocytes count in bronchoalveolar lavage fluid obtained from lungs of mice in the bleomycin lung fibrosis model treated with compound of Example 2.
Figure 5B:
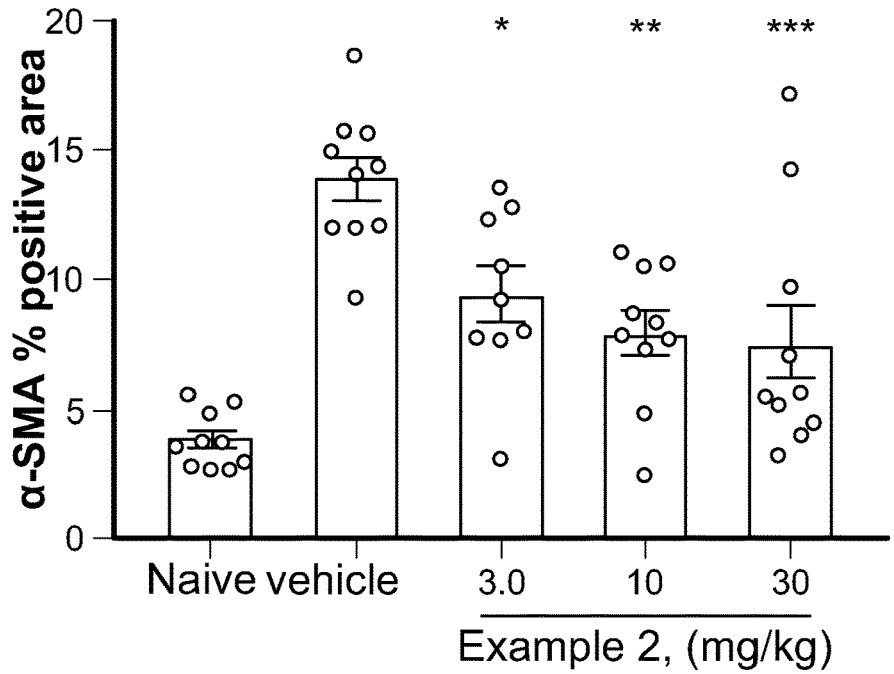
Figure 5B:
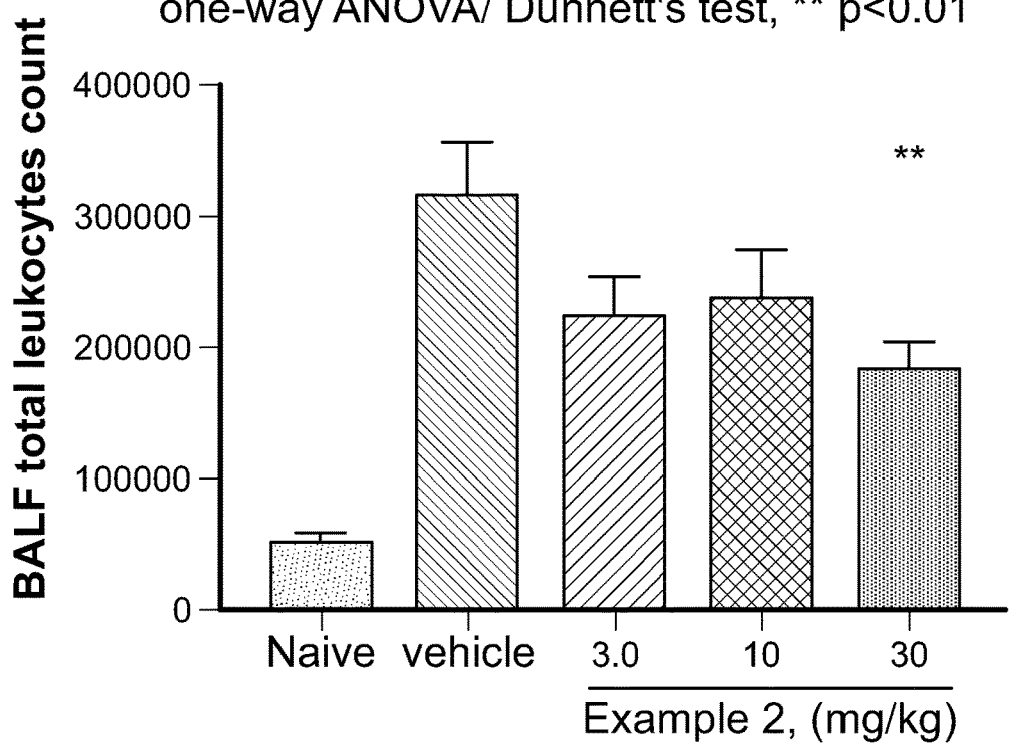

The improvement in the overall lung fibrosis, α-smooth muscle actin (αSMA) percentage positive area and total leukocytes count in bronchoalveolar lavage fluid was quantitated by applying the Ashcoft score criteria to the histopathology images, IHC quantitation and flowcytometry respectively. Administration of ≥10 mg/kg ROCK inhibitor resulted in substantially less fibrosis and lower inflammatory leukocytes infiltration compared to vehicle treated controls, as indicated by lower group mean fibrotic indices, αSMA positive area and total leukocytes count in bronchoalveolar lavage fluid. See FIG. 5b.

Example 93

Figure 6A:
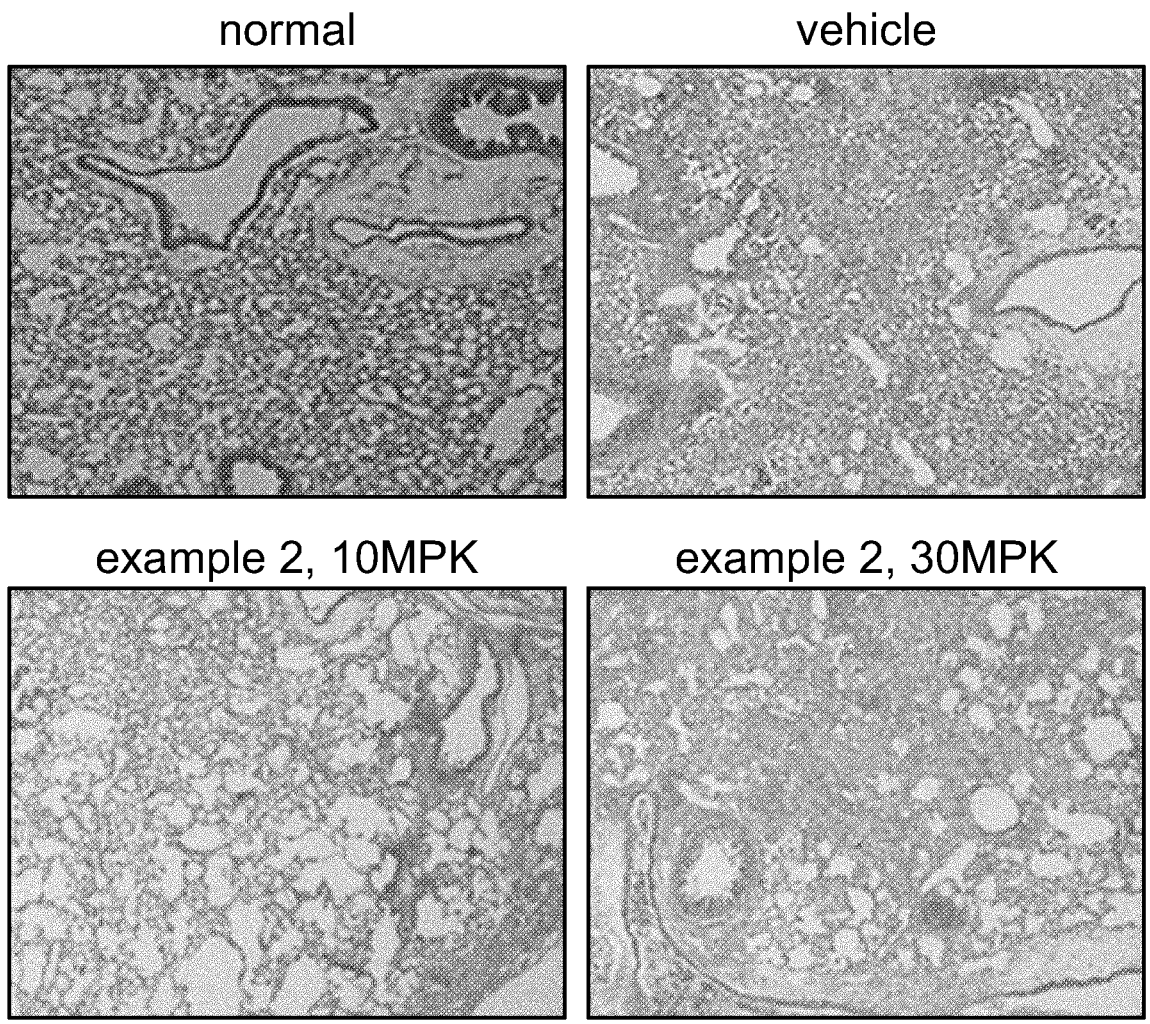
FIG. 6a. ROCK inhibitor is therapeutically active in a mouse model of pulmonary fibrosis. Representative images of lung sections stained with Masson's trichrome to visualized fibrosis in the lungs of mice following therapeutic treatment with ROCK inhibitor in the bleomycin-induced lung injury model.

ROCK Inhibition is Effective at Lowering Fibrosis Scores when Administered Therapeutically in the Bleomycin Induced Pulmonary Fibrosis Model in Mice The activity of ROCK inhibitors in attenuating pulmonary fibrosis in a therapeutic dosing setting was assessed in a bleomycin-induced model, following intratracheal bleomycin installation to induce lung tissue damage and consequent fibrosis of the lung. 7 days after bleomycin instillation, which allowed for the fibrosis to be established prior to the treatment initiation, mice were treated with the compound or vehicle control. All mice were sacrificed on day 20 and lungs were collected. The large lobe of the right lung was fixed with 10% neutral formalin, sectioned and stained with Masson's Trichrome. Clear anti-fibrotic effects were observed in 10 mg/kg and 30 mg/kg ROCK inhibitor treatment groups, as evidenced by the lower collagen contents and the decreased Masson's trichrome staining scores. See FIG. 6a.

Figure 6B:
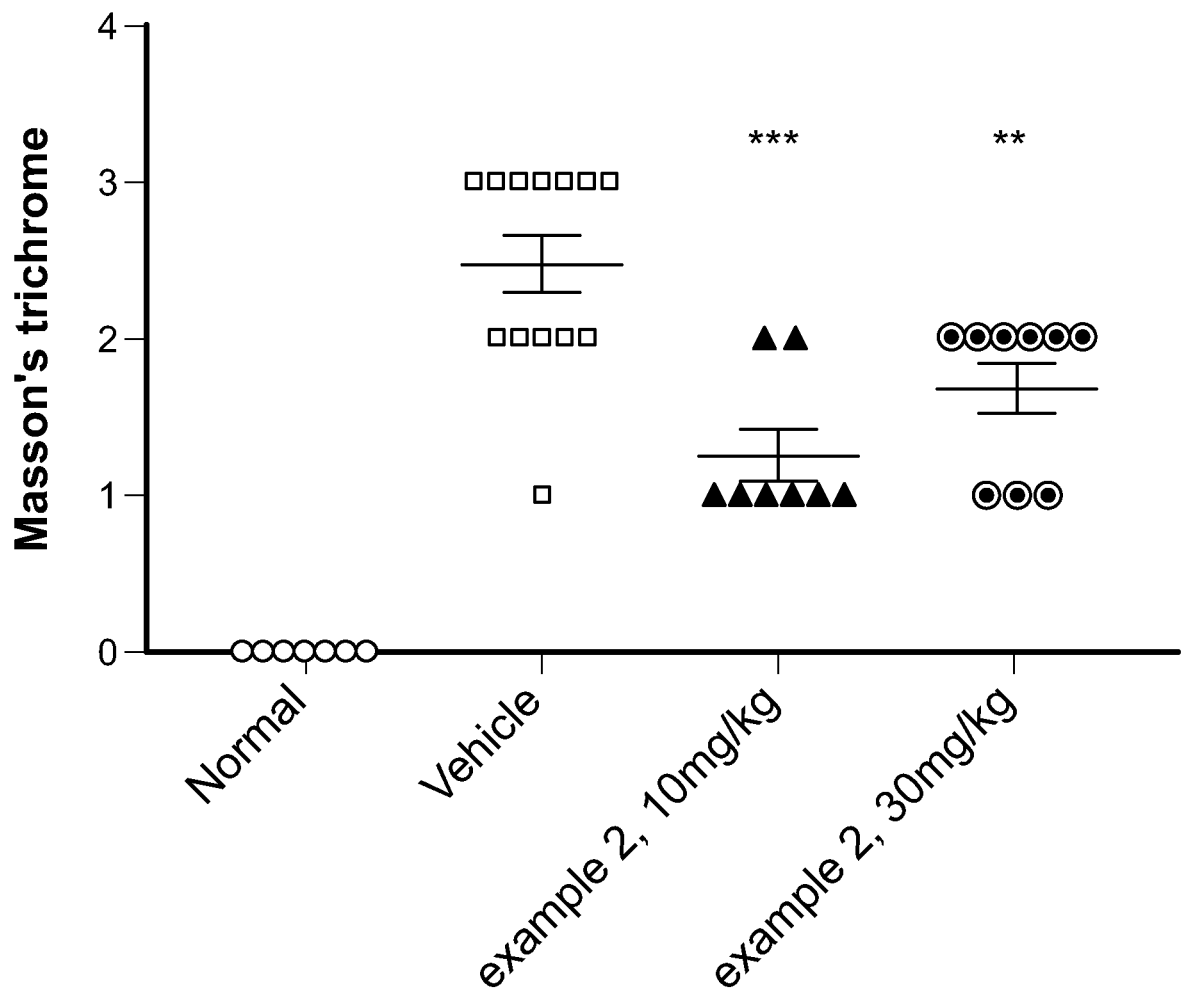
FIG. 6b. Quantitation of the decrease in the fibrosis index in the histopathological analysis of the images from ROCK inhibitor and vehicle treated mice in the bleomycin-induced lung injury model.

The improvement in the overall lung fibrosis was quantitated for each animal in the control and treatment groups. See FIG. 6b. Masson's trichrome-stained sections of the lungs from individual mice with group means, and standard errors of the means (SEM) are shown. The scores of normal control mice were 0. The collagen amounts in the lungs of compound example 2 treated mice were significantly lower.

Example 94

Figure 7A:
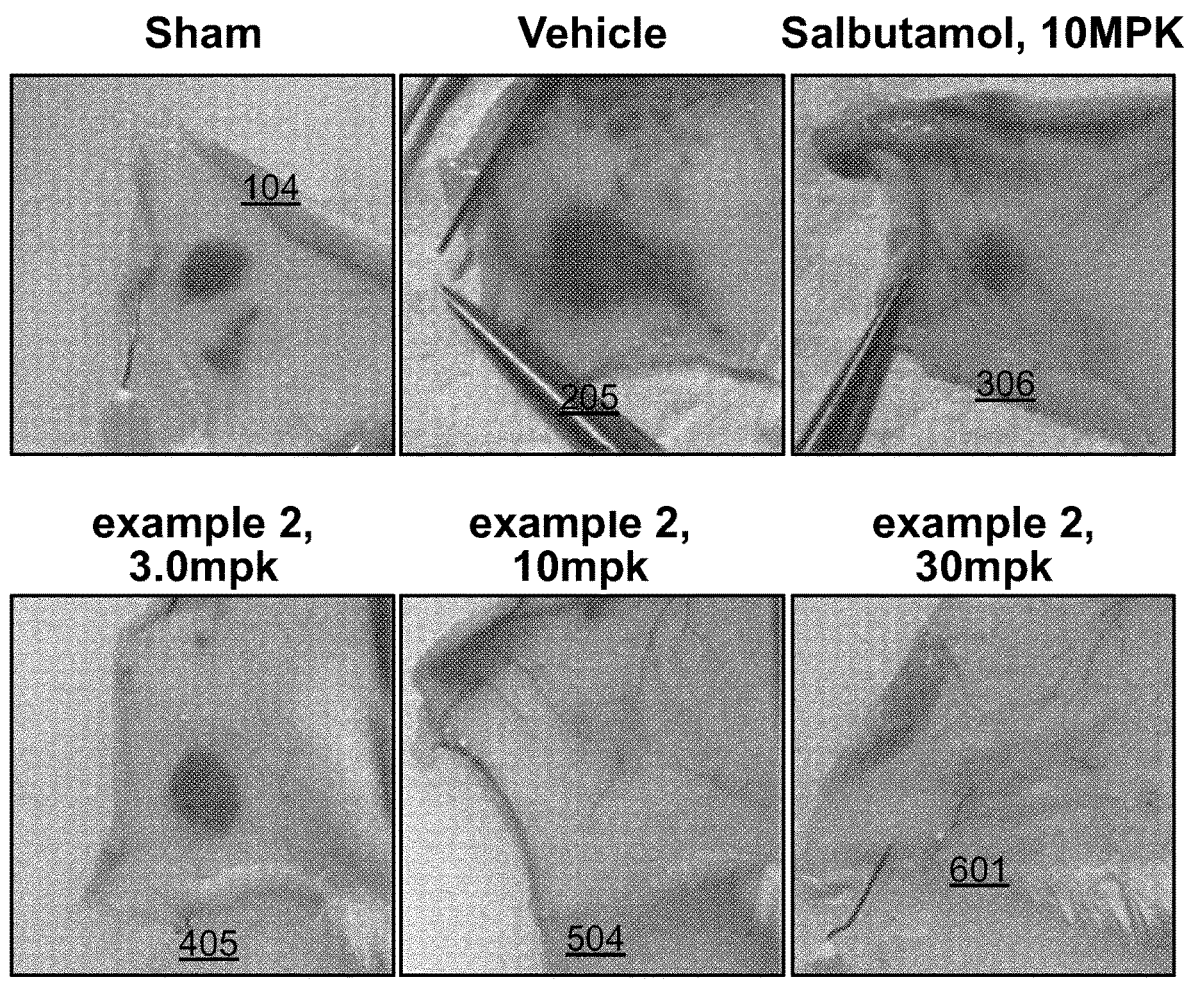
FIG. 7a. ROCK inhibition stabilizes the endothelial barrier function in a histamine-induced vascular permeability model in mice. Representative images of Evan's Blue dye extravasation induced by histamine in the skin of ROCK inhibitor and vehicle treated mice, relative to the control compound (salbutamol). ROCK inhibitor induces vascular barrier stabilization following single dose of compound administered 1 hr. prior to histamine injection.

ROCK Inhibition Stabilizes the Endothelial Barrier Function in a Histamine-Induced Vascular Permeability Model in Mice In addition to the damage sustained by the organ epithelium, in fibrotic disease, damage also occurs to the endothelial cells, causing destabilization of the endothelial barrier and capillary leakage, both hallmarks of fibrotic tissues. ROCK signaling pathway is upregulated in the injured endothelial cells and lead to further barrier destabilization and vascular leakage. The involvement of ROCK in the induction of vascular leakage allowed us to hypothesize that the administration of ROCK inhibitor could stabilize such vascular barrier function in vivo. We tested the efficacy of blocking ROCK inhibitor activity following single dose administration in a model of histamine-induced dermal vascular leakage in mice. In this model intradermal injection of histamine rapidly induced extravasation of Evan's Blue dye at the site of histamine administration. Administration of ROCK inhibitor of Example 2 1 hr. prior to histamine injection blocked the vascular permeability induced by histamine in a dose dependent manner, suggesting that in addition to the anti-fibrotic activity, ROCK inhibitions of this invention could also be utilized in disease associated with induced vascular permeability. FIG. 7a shows representative images of Evan's Blue dye extravasation induced by histamine.

Figure 7B:
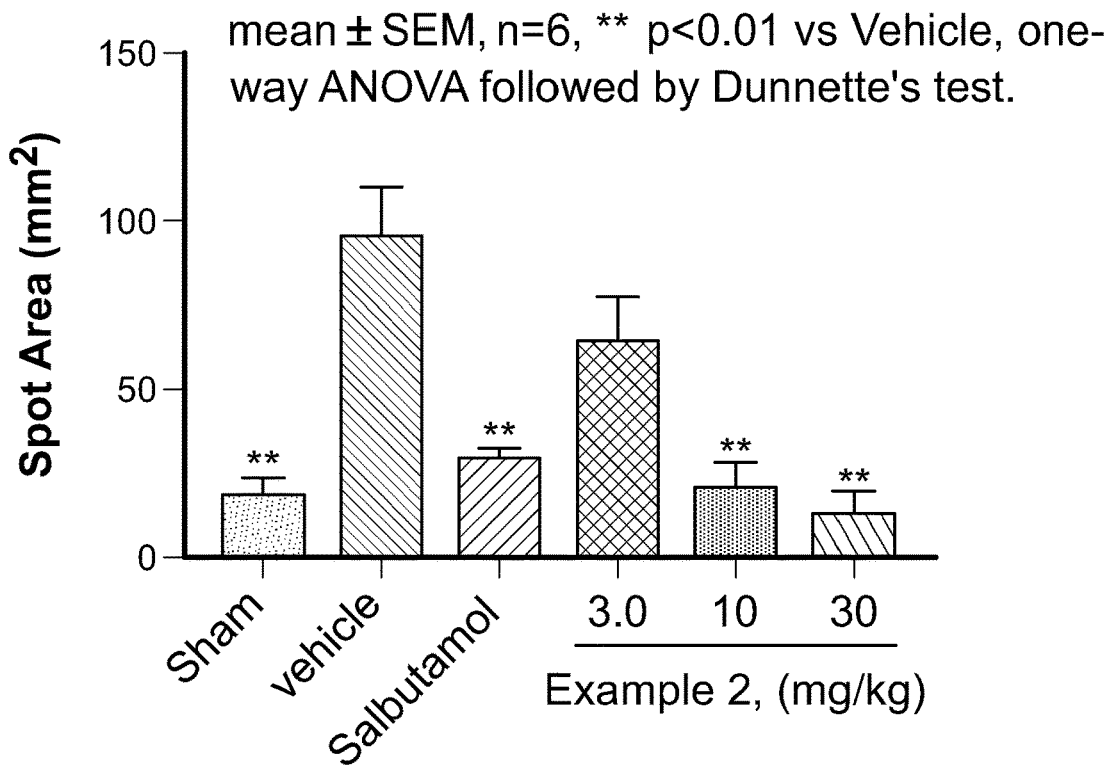
FIG. 7b. Quantitation of the decrease in spot area size and Evan's Blue dye amount in the skin of ROCK inhibitor treated mice following the induction of capillary leakage by histamine injection.
Figure 7B:
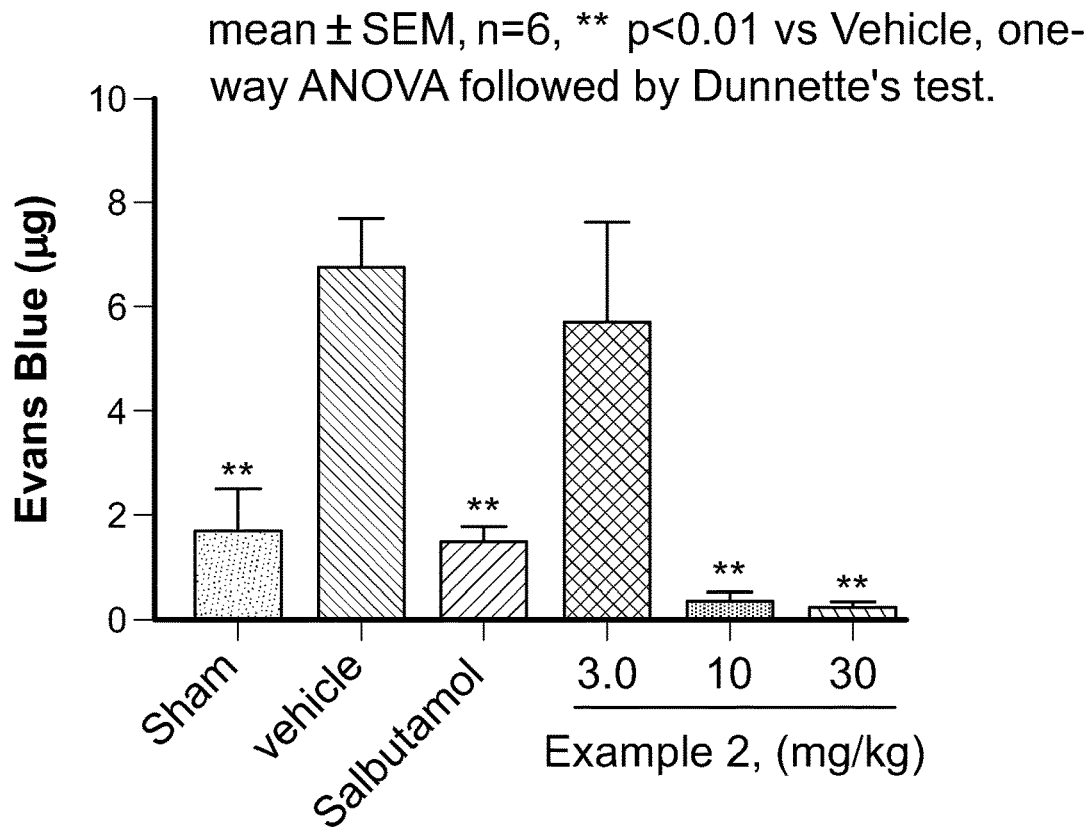

The extent of compound efficacy was quantitated by calculating both the overall skin spot area and the amount of Evans Blue dye permeating the skin. 20 Minutes post challenge with histamine, animals were euthanized, the lesion diameters were measured. The area of the lesion was calculated and expressed in square millimeters. Following diameter measurements, Evan's Blue dye was extracted from the skin tissue and the optical density was measured. Data are calculated against a spiked in Evan's Blue standard curve. ** $p<0.01$ vs Vehicle group using one-way ANOVA followed by Dunnette post-test. See FIG. 7b.

BIBLIOGRAPHY

Deyts, C., Galan-Rodriguez, B., Martin, E., Bouveyron, N., Roze, E., Charvin, D., Caboche, J., and Betuing, S.

(2009). Dopamine D2 receptor stimulation potentiates PolyQ-Huntingtin-induced mouse striatal neuron dysfunctions via Rho/ROCK-II activation. PLoS One 4, e8287.

Govek, E. E., Newey, S. E., and Van Aelst, L. (2005). The role of the Rho GTPases in neuronal development. Genes Dev 19, 1-49.

Li, M., Huang, Y., Ma, A. A., Lin, E., and Diamond, M. I. (2009). Y-27632 improves rotarod performance and reduces huntingtin levels in R6/2 mice. Neurobiol Dis 36, 413-420.

Linseman, D. A., and Loucks, F. A. (2008). Diverse roles of Rho family GTPases in neuronal development, survival, and death. Front Biosci 13, 657-676.

Petratos, S., Li, Q. X., George, A. J., Hou, X., Kerr, M. L., Unabia, S. E., Hatzinisiriou, I., Maksel, D., Aguilar, M. I., and Small, D. H. (2008). The beta-amyloid protein of Alzheimer's disease increases neuronal CRMP-2 phosphorylation by a Rho-GTP mechanism. Brain 131, 90-108.

Selkoe, D. J. (2001). Alzheimer's disease: genes, proteins, and therapy. Physiol Rev 81, 741-766.

Shao, J., and Diamond, M. I. (2007). Polyglutamine diseases: emerging concepts in pathogenesis and therapy. Hum Mol Genet 16 Spec No. 2, R115-123.

Shao, J., Welch, W. J., and Diamond, M. I. (2008a). ROCK and PRK-2 mediate the inhibitory effect of Y-27632 on polyglutamine aggregation. FEBS Lett 582, 1637-1642.

Shao, J., Welch, W. J., Diprospero, N. A., and Diamond, M. I. (2008b). Phosphorylation of profilin by ROCK1 regulates polyglutamine aggregation. Mol Cell Biol 28, 5196-5208.

Tanzi, R. E., and Bertram, L. (2005). Twenty years of the Alzheimer's disease amyloid hypothesis: a genetic perspective. Cell 120, 545-555.

The invention claimed is:
1. A compound having the formula I:

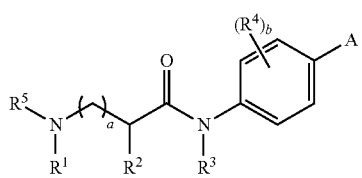

(I)

wherein:
A is selected from the group consisting of

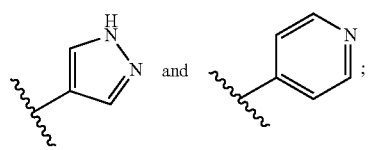 [SMILES: *c1cn[nH]c1 ; "and" ; *c1ccncc1 ; ";"]

and $R^1$ is selected from the group consisting of lower alkyl, substituted lower alkyl, $C_3$-$C_6$ cycloalkyl, substituted $C_3$-$C_6$ cycloalkyl, $R^{10}R^{11}N(CR^{12}R^{13})_c$—, $R^{10}O(CR^{12}R^{13})_c$—, $W(CR^{12}R^{13})_d$— and $R^{10}R^{11}N$—C(=O)—$(CR^{12}R^{13})_c$—;

each $R^{10}$ is independently selected from H, lower alkyl, and $C_3$-$C_6$ cycloalkyl;

each $R^{11}$ is independently selected from H, lower alkyl, and $C_3$-$C_6$ cycloalkyl;

each $R^{12}$ is independently selected from H and lower alkyl;

each $R^{13}$ is independently selected from H and lower alkyl;

additionally or alternatively, an $R^{12}$ and an $R^{13}$ attached to the same carbon atom may be taken together to form a $C_3$-$C_6$ cycloalkyl group;

W is a 3- to 7-membered heterocyclic or heteroaryl ring having 1 to 3 ring heteroatoms;

c is 2 to 4;

d is 1 to 4;

$R^2$ is selected from the group consisting of aryl, heteroaryl, and heterocyclyl, each of which may be monocyclic or bicyclic and optionally substituted with 1 to 3 substituents independently selected from the group consisting of halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, $RO_2C$—, aryl-O— and heteroaryl-O—;

$R^3$ is selected from H, lower alkyl, substituted lower alkyl, and RR'N—($C_{2-4}$ alkyl)-;

$R^4$ is selected from the group consisting of H, halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, RR'N—($C_{2-4}$ alkyl)-, and RR'N—($C_{2-4}$ alkyl)-O—;

$R^5$ is selected from H, lower alkyl and $C_3$-$C_6$ cycloalkyl;

alternatively, $R^3$ and $R^5$ taken together form a cyclic group having 5 to 7 ring atoms, including 2-3 ring heteroatoms, wherein the cyclic group is unsubstituted or is optionally substituted with 1 to 3 substituents independently selected from the group consisting of halo, hydroxy, lower alkyl, lower alkoxy, amino, nitro, cyano, $C_1$-$C_3$ perfluoro alkyl, $C_1$-$C_3$ perfluoro alkoxy, carboxyl, aryl and heteroaryl;

a is 0 or 1;

b is 0 to 2;

and each R and R' is independently selected from H, lower alkyl, and $C_3$-$C_6$ cycloalkyl, or alternatively, R and R' taken together form a 5 to 6 membered heterocyclic ring; or a pharmaceutically-acceptable salt thereof.

2. The compound according to claim 1, having the formula II:

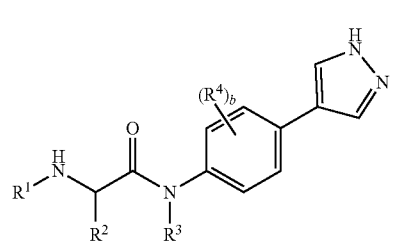

(II)

or a pharmaceutically-acceptable salt thereof.

3. The compound according to claim 1, having the formula V:

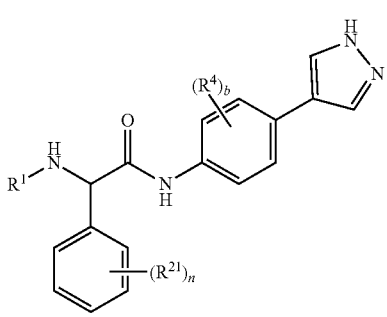
(V)

wherein:
R¹ is selected from the group consisting of lower alkyl and substituted lower alkyl;
each $R^{21}$ is independently selected from the group consisting of H, halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, $RO_2C$—, aryl-O— and heteroaryl-O—;
each R and R' is independently selected from H, lower alkyl, and $C_3$-$C_6$ cycloalkyl, or alternatively, R and R' taken together form a 5 to 6 membered heterocyclic ring; and
n is 0 to 3; or a pharmaceutically-acceptable salt thereof.

4. The compound according to claim 1, having the formula VI:

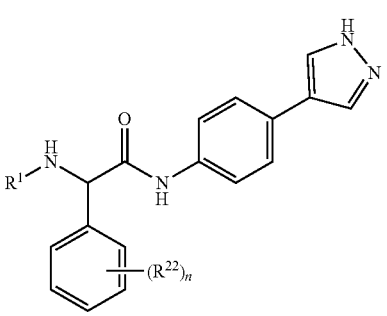
(VI)

wherein:
R¹ is selected from the group consisting of lower alkyl and substituted lower alkyl;
each $R^{22}$ is independently selected from H, halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, $RO_2C$—, aryl-O— and heteroaryl-O—;
each R and R' is independently selected from H, lower alkyl, and $C_3$-$C_6$ cycloalkyl, or alternatively, R and R' taken together form a 5 to 6 membered heterocyclic ring; and
n is 0 to 3; or a pharmaceutically-acceptable salt thereof.

5. A method of treating a fibrotic disorder in a subject comprising administering to the subject a therapeutically effective amount of a compound according to claim 1; or a pharmaceutically-acceptable salt thereof.

6. The method of claim 5, wherein the fibrotic disorder is selected from the group consisting of pulmonary fibrosis, cystic and idiopathic pulmonary fibrosis, radiation induced lung injury, liver fibrosis, liver cirrhosis, cardiac fibrosis, arterial fibrosis, endomyocardial fibrosis, old myocardial infraction, arterial stiffness, atherosclerosis, restenosis, arthrofibrosis, Crohn's disease, myelofibrosis, Peyronie's diseases, nephrogenic systemic fibrosis, progressive massive fibrosis, retroperitoneal cavity fibrosis, scheroderma/systemic sclerosis, mediastinal fibrosis, Keloids and hypertrophic scars, glial scaring, and renal fibrosis.

7. A method of treating a central nervous system disorder in a subject comprising administering to the subject a therapeutically effective amount of a compound according claim 1; or a pharmaceutically-acceptable salt thereof.

8. The method of claim 7, wherein the central nervous system disorder is selected from the group consisting of Huntington's disease, Parkinson's Disease, Alzheimer's, Amyotrophic lateral sclerosis (ALS), Batten disease, dementia, spinal muscular atrophy, motor neurone diseases, spinocerebellar ataxia, acute or chronic pain, neuronal degeneration, spinal cord injury, cerebral vasospasm and multiple sclerosis.

9. A method of treating a disease in a subject that is mediated by ROCK1 or ROCK2 comprising administering to the subject a therapeutically effective amount of a compound according to claim 1; or a pharmaceutically-acceptable salt thereof.

10. A compound having the formula:

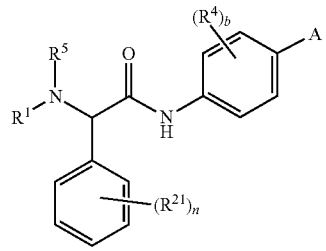

wherein:
A is selected from the group consisting of

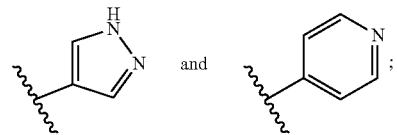 [SMILES: *c1cn[nH]c1 ; "and" ; *c1ccncc1 ; ";"]
and

R¹ is selected from the group consisting of lower alkyl and lower alkyl substituted with —NH($C_{1-4}$alkyl), —N($C_{1-4}$alkyl)₂, —O—$C_{1-4}$alkyl, —O—$C_{1-4}$alkyl-$CF_3$, —C(=O)—$NH_2$, —C(=O)—NH($C_{1-4}$alkyl), —C(=O)—N($C_{1-4}$alkyl)₂, cyclopropyl, or five to six-membered heteroaryl or heterocyclyl;
$R^4$ is selected from halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, RR'N—($C_{2-4}$ alkyl)-, and RR'N—($C_{2-4}$ alkyl)-O—;
$R^5$ is hydrogen or lower alkyl;
each $R^{21}$ is selected from halo, hydroxy, lower alkyl, lower alkoxy, nitro, cyano, $C_1$-$C_3$ perfluoro alkyl, $C_1$-$C_3$ perfluoro alkoxy, carboxyl, RR'N—, RR'NCO—, RCONH—, RCONR'—, $RO_2C$—, aryl- O— and heteroaryl-O—; or two $R^{21}$ groups taken together form a cyclic group having 5 ring atoms, including 2-3 ring heteroatoms, wherein the cyclic group is unsubstituted or is optionally substituted with 1 to 3 substituents independently selected from the group consisting of halo, hydroxy, lower alkyl, lower alkoxy, amino, nitro, cyano, $C_1$-$C_3$ perfluoro alkyl, $C_1$-$C_3$ perfluoro alkoxy, carboxyl, aryl and heteroaryl;

each R and R' is independently selected from H, lower alkyl, and $C_3$-$C_6$ cycloalkyl, or alternatively, R and R' taken together form a 5 to 6 membered heterocyclic ring;

b is 0 to 3; and n is 0 to 3; or a pharmaceutically-acceptable salt thereof.

11. A compound according to claim 10, wherein $R^1$ is lower alkyl; or a pharmaceutically-acceptable salt thereof.

12. A compound according to claim 10, wherein A is

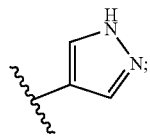 [SMILES: *c1cn[nH]c1]

or a pharmaceutically-acceptable salt thereof.

13. A compound according to claim 10, wherein A is

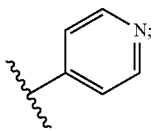 [SMILES: *c1ccncc1]

or a pharmaceutically-acceptable salt thereof.

14. A compound according to claim 10, wherein $R^1$ is lower alkyl or lower alkyl substituted with —NH($C_{1-4}$alkyl), —N($C_{1-4}$alkyl)$_2$, or —O—$C_{1-4}$alkyl; or a pharmaceutically-acceptable salt thereof.

15. A compound according to claim 14, wherein $R^{21}$ is selected from halogen, lower alkyl, lower alkoxy, —C(=O)—NH($C_{1-4}$alkyl), and n is 1 or 2; or a pharmaceutically-acceptable salt thereof.

16. A compound according to claim 15, wherein $R^1$ is methyl; or a pharmaceutically-acceptable salt thereof.

17. A compound according to claim 16, wherein b is 0; or a pharmaceutically-acceptable salt thereof.

18. A compound according to claim 10, having the formula:

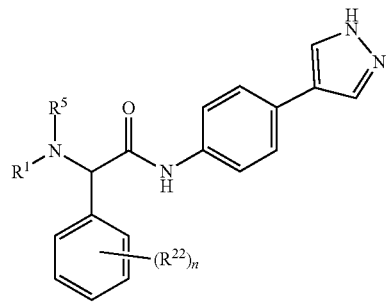

wherein:

$R^1$ is selected from the group consisting of lower alkyl and lower alkyl substituted with —NH($C_{1-4}$alkyl), —N($C_{1-4}$alkyl)$_2$, —O—$C_{1-4}$alkyl, —O—$C_{1-4}$alkyl-CF$_3$, —C(=O)—NH$_2$, —C(=O)—NH($C_{1-4}$alkyl), —C(=O)—N($C_{1-4}$alkyl)$_2$, cyclopropyl, or five to six-membered heteroaryl or heterocyclyl;

$R^{21}$ is selected from halogen, lower alkyl, lower alkoxy, and —C(=O)—NH($C_{1-4}$alkyl); and n is 1 or 2; or a pharmaceutically-acceptable salt thereof.

19. A compound according to claim 18, wherein $R^1$ is methyl and $R^5$ is hydrogen; or a pharmaceutically-acceptable salt thereof.

20. A compound according to claim 19, having the structure:

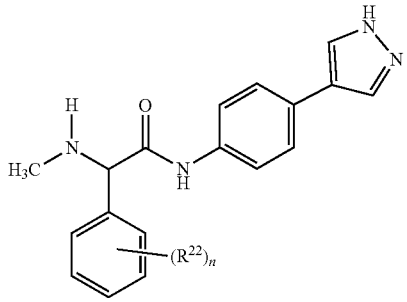

wherein:

$R^{22}$ is methoxy and n is 1; or a pharmaceutically-acceptable salt thereof.

* * * * *

UNITED STATES PATENT AND TRADEMARK OFFICE
CERTIFICATE OF CORRECTION

| | |
|---|---|
| PATENT NO. | : 11,479,533 B2 |
| APPLICATION NO. | : 16/632662 |
| DATED | : October 25, 2022 |
| INVENTOR(S) | : Eduardas Skucas et al. |

It is certified that error appears in the above-identified patent and that said Letters Patent is hereby corrected as shown below:

In the Claims

Claim 18, Column 94, Line 24, "$R^{21}$ is selected from halogen, lower alkyl, lower alkoxy," should be -- $R^{22}$ is selected from halogen, lower alkyl, lower alkoxy, --

Signed and Sealed this
Eleventh Day of April, 2023

Katherine Kelly Vidal
*Director of the United States Patent and Trademark Office*